US010774346B2

United States Patent
Kumaran et al.

(10) Patent No.: US 10,774,346 B2
(45) Date of Patent: Sep. 15, 2020

(54) METABOLIC ENGINEERING FOR MICROBIAL PRODUCTION OF TERPENOID PRODUCTS

(71) Applicant: MANUS BIO INC., Cambridge, MA (US)

(72) Inventors: Ajikumar Parayil Kumaran, Cambridge, MA (US); Ryan Lim, Cambridge, MA (US); Jason Donald, Cambridge, MA (US); Hsien-Chung Tseng, Cambridge, MA (US); Christine Nicole S. Santos, Cambridge, MA (US); Ryan Philippe, Cambridge, MA (US)

(73) Assignee: MANUS BIO INC., Cambridge, MA (US)

( * ) Notice: Subject to any disclaimer, the term of this patent is extended or adjusted under 35 U.S.C. 154(b) by 0 days.

(21) Appl. No.: 16/570,251

(22) Filed: Sep. 13, 2019

(65) Prior Publication Data
US 2020/0002733 A1    Jan. 2, 2020

Related U.S. Application Data

(63) Continuation of application No. 15/881,386, filed on Jan. 26, 2018, now Pat. No. 10,480,015.

(60) Provisional application No. 62/450,707, filed on Jan. 26, 2017.

(51) Int. Cl.
| | |
|---|---|
| *C12N 15/52* | (2006.01) |
| *C12P 5/00* | (2006.01) |
| *C12N 9/02* | (2006.01) |
| *C12P 7/04* | (2006.01) |

(52) U.S. Cl.
CPC ............ *C12P 5/007* (2013.01); *C12N 9/0008* (2013.01); *C12N 9/0093* (2013.01); *C12N 15/52* (2013.01); *C12P 7/04* (2013.01); *C12Y 102/07001* (2013.01); *C12Y 117/07001* (2013.01)

(58) Field of Classification Search
CPC .................................. C12N 15/52; C12P 5/007
See application file for complete search history.

(56) References Cited

U.S. PATENT DOCUMENTS

| | | | |
|---|---|---|---|
| 8,512,988 B2 | 8/2013 | Ajikumar et al. | |
| 8,927,241 B2 | 1/2015 | Ajikumar et al. | |
| 9,284,570 B2 | 3/2016 | Stephanopoulos et al. | |
| 9,359,624 B2 | 6/2016 | Ajikumar et al. | |
| 9,404,130 B2 | 8/2016 | Ajikumar et al. | |
| 9,796,980 B2 | 10/2017 | Ajikumar et al. | |
| 9,957,527 B2 | 5/2018 | Ajikumar et al. | |
| 10,480,015 B2 * | 11/2019 | Kumaran | C12P 5/007 |
| 2014/0162337 A1 | 6/2014 | Chotani et al. | |
| 2015/0044747 A1 | 2/2015 | Chou et al. | |
| 2015/0152446 A1 | 6/2015 | Ajikumar et al. | |
| 2015/0225754 A1 | 8/2015 | Tange et al. | |

FOREIGN PATENT DOCUMENTS

| | | |
|---|---|---|
| EP | 1987147 B1 | 7/2010 |
| WO | 2015189428 A1 | 12/2015 |
| WO | 2016029153 A1 | 2/2016 |
| WO | 2016073740 A1 | 5/2016 |
| WO | 2017034942 | 3/2017 |
| WO | 2017142993 | 8/2017 |

OTHER PUBLICATIONS

Bentley et al. "Heterologous Expression of the Mevalonic Acid Pathway in Cyanobacteria Enhances Endogenous Carbon Partitioning to Isoprene," Molecular Plant, 2014, vol. 7, No. 1, pp. 71-86.
Chou et al. "Synthetic Pathway for Production of Five-Carbon Alcohols from Isopentenyl Diphosphate," Applied and Environmental Microbiology, 2012, vol. 78, No. 22, pp. 7849-7855.
International Search Report, for International Application No. PCT/US2018/016848, dated Apr. 23, 2018, 11 pages.
International Search Report, for International Application No. PCT/US2018/015527, dated May 2, 2018, 12 pages.
Zhou et al. "Metabolite Profiling Identified Methylerythritol Cyclodiphosphate Efflux as a Limiting Step in Microbial Isoprenoid Production," PloS One, 2012, vol. 7 No. 1, pp. 1-9.

\* cited by examiner

*Primary Examiner* — Tekchand Saidha
(74) *Attorney, Agent, or Firm* — Morgan, Lewis & Bockius LLP

(57) ABSTRACT

The invention relates to methods and bacterial strains for making terpene and terpenoid products, the bacterial strains having improved carbon pull through the MEP pathway and to a downstream recombinant synthesis pathway.

27 Claims, 25 Drawing Sheets
Specification includes a Sequence Listing.

SEQUENCE LISTING

<160> NUMBER OF SEQ ID NOS: 38

<210> SEQ ID NO 1
<211> LENGTH: 372
<212> TYPE: PRT
<213> ORGANISM: E. coli

<400> SEQUENCE: 1

Met His Asn Gln Ala Pro Ile Gln Arg Arg Lys Ser Thr Arg Ile Tyr
1               5                   10                  15

Val Gly Asn Val Pro Ile Gly Asp Gly Ala Pro Ile Ala Val Gln Ser
            20                  25                  30

Met Thr Asn Thr Arg Thr Thr Asp Val Glu Ala Thr Val Asn Gln Ile
        35                  40                  45

Lys Ala Leu Glu Arg Val Gly Ala Asp Ile Val Arg Val Ser Val Pro
    50                  55                  60

Thr Met Asp Ala Ala Glu Ala Phe Lys Leu Ile Lys Gln Gln Val Asn
65                  70                  75                  80

Val Pro Leu Val Ala Asp Ile His Phe Asp Tyr Arg Ile Ala Leu Lys
                85                  90                  95

Val Ala Glu Tyr Gly Val Asp Cys Leu Arg Ile Asn Pro Gly Asn Ile
            100                 105                 110

Gly Asn Glu Glu Arg Ile Arg Met Val Val Asp Cys Ala Arg Asp Lys
        115                 120                 125

Asn Ile Pro Ile Arg Ile Gly Val Asn Ala Gly Ser Leu Glu Lys Asp
130                 135                 140

Leu Gln Glu Lys Tyr Gly Glu Pro Thr Pro Gln Ala Leu Leu Glu Ser
145                 150                 155                 160

Ala Met Arg His Val Asp His Leu Asp Arg Leu Asn Phe Asp Gln Phe
                165                 170                 175

Lys Val Ser Val Lys Ala Ser Asp Val Phe Leu Ala Val Glu Ser Tyr
            180                 185                 190

Arg Leu Leu Ala Lys Gln Ile Asp Gln Pro Leu His Leu Gly Ile Thr
        195                 200                 205

Glu Ala Gly Gly Ala Arg Ser Gly Ala Val Lys Ser Ala Ile Gly Leu
210                 215                 220

Gly Leu Leu Leu Ser Glu Gly Ile Gly Asp Thr Leu Arg Val Ser Leu
225                 230                 235                 240

Ala Ala Asp Pro Val Glu Glu Ile Lys Val Gly Phe Asp Ile Leu Lys
                245                 250                 255

Ser Leu Arg Ile Arg Ser Arg Gly Ile Asn Phe Ile Ala Cys Pro Thr
            260                 265                 270

Cys Ser Arg Gln Glu Phe Asp Val Ile Gly Thr Val Asn Ala Leu Glu
        275                 280                 285

Gln Arg Leu Glu Asp Ile Ile Thr Pro Met Asp Val Ser Ile Ile Gly
290                 295                 300

Cys Val Val Asn Gly Pro Gly Glu Ala Leu Val Ser Thr Leu Gly Val
305                 310                 315                 320

Thr Gly Gly Asn Lys Lys Ser Gly Leu Tyr Glu Asp Gly Val Arg Lys
                325                 330                 335

Asp Arg Leu Asp Asn Asn Asp Met Ile Asp Gln Leu Glu Ala Arg Ile
            340                 345                 350

Arg Ala Lys Ala Ser Gln Leu Asp Glu Ala Arg Arg Ile Asp Val Gln
        355                 360                 365

Gln Val Glu Lys
    370

<210> SEQ ID NO 2
<211> LENGTH: 316
<212> TYPE: PRT
<213> ORGANISM: E. coli

<400> SEQUENCE: 2

Met Gln Ile Leu Leu Ala Asn Pro Arg Gly Phe Cys Ala Gly Val Asp
1               5                   10                  15

Arg Ala Ile Ser Ile Val Glu Asn Ala Leu Ala Ile Tyr Gly Ala Pro
            20                  25                  30

Ile Tyr Val Arg His Glu Val His Asn Arg Tyr Val Val Asp Ser
        35                  40                  45

Leu Arg Glu Arg Gly Ala Ile Phe Ile Glu Gln Ile Ser Glu Val Pro
    50                  55                  60

Asp Gly Ala Ile Leu Ile Phe Ser Ala His Gly Val Ser Gln Ala Val
65                  70                  75                  80

Arg Asn Glu Ala Lys Ser Arg Asp Leu Thr Val Phe Asp Ala Thr Cys
                85                  90                  95

Pro Leu Val Thr Lys Val His Met Glu Val Ala Arg Ala Ser Arg Arg
            100                 105                 110

Gly Glu Glu Ser Ile Leu Ile Gly His Ala Gly His Pro Glu Val Glu
        115                 120                 125

Gly Thr Met Gly Gln Tyr Ser Asn Pro Glu Gly Met Tyr Leu Val
            130                 135                 140

Glu Ser Pro Asp Asp Val Trp Lys Leu Thr Val Lys Asn Glu Glu Lys
145                 150                 155                 160

Leu Ser Phe Met Thr Gln Thr Leu Ser Val Asp Asp Thr Ser Asp
                165                 170                 175

Val Ile Asp Ala Leu Arg Lys Arg Phe Pro Lys Ile Val Gly Pro Arg
                180                 185                 190

Lys Asp Asp Ile Cys Tyr Ala Thr Thr Asn Arg Gln Glu Ala Val Arg
                195                 200                 205

Ala Leu Ala Glu Gln Ala Glu Val Val Leu Val Val Gly Ser Lys Asn
            210                 215                 220

Ser Ser Asn Ser Asn Arg Leu Ala Glu Leu Ala Gln Arg Met Gly Lys
225                 230                 235                 240

Arg Ala Phe Leu Ile Asp Asp Ala Lys Asp Ile Gln Glu Glu Trp Val
                245                 250                 255

Lys Glu Val Lys Cys Val Gly Val Thr Ala Gly Ala Ser Ala Pro Asp
                260                 265                 270

Ile Leu Val Gln Asn Val Val Ala Arg Leu Gln Gln Leu Gly Gly Gly
                275                 280                 285

Glu Ala Ile Pro Leu Glu Gly Arg Glu Glu Asn Ile Val Phe Glu Val
            290                 295                 300

Pro Lys Glu Leu Arg Val Asp Ile Arg Glu Val Asp
305                 310                 315

<210> SEQ ID NO 3
<211> LENGTH: 620
<212> TYPE: PRT
<213> ORGANISM: E. coli

<400> SEQUENCE: 3

Met Ser Phe Asp Ile Ala Lys Tyr Pro Thr Leu Ala Leu Val Asp Ser
1               5                   10                  15

Thr Gln Glu Leu Arg Leu Leu Pro Lys Glu Ser Leu Pro Lys Leu Cys
                20                  25                  30

Asp Glu Leu Arg Arg Tyr Leu Leu Asp Ser Val Ser Arg Ser Ser Gly
                35                  40                  45

His Phe Ala Ser Gly Leu Gly Thr Val Glu Leu Thr Val Ala Leu His
            50                  55                  60

Tyr Val Tyr Asn Thr Pro Phe Asp Gln Leu Ile Trp Asp Val Gly His
65                  70                  75                  80

Gln Ala Tyr Pro His Lys Ile Leu Thr Gly Arg Arg Asp Lys Ile Gly
                85                  90                  95

Thr Ile Arg Gln Lys Gly Gly Leu His Pro Phe Pro Trp Arg Gly Glu
                100                 105                 110

Ser Glu Tyr Asp Val Leu Ser Val Gly His Ser Ser Thr Ser Ile Ser
            115                 120                 125

Ala Gly Ile Gly Ile Ala Val Ala Ala Glu Lys Glu Gly Lys Asn Arg
            130                 135                 140

Arg Thr Val Cys Val Ile Gly Asp Gly Ala Ile Thr Ala Gly Met Ala
145                 150                 155                 160

Phe Glu Ala Met Asn His Ala Gly Asp Ile Arg Pro Asp Met Leu Val
                165                 170                 175

Ile Leu Asn Asp Asn Glu Met Ser Ile Ser Glu Asn Val Gly Ala Leu

```
                180             185                 190
Asn Asn His Leu Ala Gln Leu Leu Ser Gly Lys Leu Tyr Ser Ser Leu
        195                 200                 205

Arg Glu Gly Gly Lys Lys Val Phe Ser Gly Val Pro Pro Ile Lys Glu
    210                 215                 220

Leu Leu Lys Arg Thr Glu His Ile Lys Gly Met Val Val Pro Gly
225                 230                 235                 240

Thr Leu Phe Glu Glu Leu Gly Phe Asn Tyr Ile Gly Pro Val Asp Gly
                245                 250                 255

His Asp Val Leu Gly Leu Ile Thr Thr Leu Lys Asn Met Arg Asp Leu
                260                 265                 270

Lys Gly Pro Gln Phe Leu His Ile Met Thr Lys Lys Gly Arg Gly Tyr
                275                 280                 285

Glu Pro Ala Glu Lys Asp Pro Ile Thr Phe His Ala Val Pro Lys Phe
                290                 295                 300

Asp Pro Ser Ser Gly Cys Leu Pro Lys Ser Ser Gly Gly Leu Pro Ser
305                 310                 315                 320

Tyr Ser Lys Ile Phe Gly Asp Trp Leu Cys Glu Thr Ala Ala Lys Asp
                325                 330                 335

Asn Lys Leu Met Ala Ile Thr Pro Ala Met Arg Glu Gly Ser Gly Met
                340                 345                 350

Val Glu Phe Ser Arg Lys Phe Pro Asp Arg Tyr Phe Asp Val Ala Ile
                355                 360                 365

Ala Glu Gln His Ala Val Thr Phe Ala Ala Gly Leu Ala Ile Gly Gly
                370                 375                 380

Tyr Lys Pro Ile Val Ala Ile Tyr Ser Thr Phe Leu Gln Arg Ala Tyr
385                 390                 395                 400

Asp Gln Val Leu His Asp Val Ala Ile Gln Lys Leu Pro Val Leu Phe
                405                 410                 415

Ala Ile Asp Arg Ala Gly Ile Val Gly Ala Asp Gly Gln Thr His Gln
                420                 425                 430

Gly Ala Phe Asp Leu Ser Tyr Leu Arg Cys Ile Pro Glu Met Val Ile
                435                 440                 445

Met Thr Pro Ser Asp Glu Asn Glu Cys Arg Gln Met Leu Tyr Thr Gly
                450                 455                 460

Tyr His Tyr Asn Asp Gly Pro Ser Ala Val Arg Tyr Pro Arg Gly Asn
465                 470                 475                 480

Ala Val Gly Val Glu Leu Thr Pro Leu Glu Lys Leu Pro Ile Gly Lys
                485                 490                 495

Gly Ile Val Lys Arg Arg Gly Glu Lys Leu Ala Ile Leu Asn Phe Gly
                500                 505                 510

Thr Leu Met Pro Glu Ala Ala Lys Val Ala Glu Ser Leu Asn Ala Thr
                515                 520                 525

Leu Val Asp Met Arg Phe Val Lys Pro Leu Asp Glu Ala Leu Ile Leu
                530                 535                 540

Glu Met Ala Ala Ser His Glu Ala Leu Val Thr Val Glu Glu Asn Ala
545                 550                 555                 560

Ile Met Gly Gly Ala Gly Ser Gly Val Asn Glu Val Leu Met Ala His
                565                 570                 575

Arg Lys Pro Val Pro Val Leu Asn Ile Gly Leu Pro Asp Phe Phe Ile
                580                 585                 590

Pro Gln Gly Thr Gln Glu Glu Met Arg Ala Glu Leu Gly Leu Asp Ala
                595                 600                 605
```

Ala Gly Met Glu Ala Lys Ile Lys Ala Trp Leu Ala
610                 615                 620

<210> SEQ ID NO 4
<211> LENGTH: 398
<212> TYPE: PRT
<213> ORGANISM: E. coli

<400> SEQUENCE: 4

Met Lys Gln Leu Thr Ile Leu Gly Ser Thr Gly Ser Ile Gly Cys Ser
1               5                   10                  15

Thr Leu Asp Val Val Arg His Asn Pro Glu His Phe Arg Val Val Ala
            20                  25                  30

Leu Val Ala Gly Lys Asn Val Thr Arg Met Val Glu Gln Cys Leu Glu
        35                  40                  45

Phe Ser Pro Arg Tyr Ala Val Met Asp Asp Glu Ala Ser Ala Lys Leu
    50                  55                  60

Leu Lys Thr Met Leu Gln Gln Gly Ser Arg Thr Glu Val Leu Ser
65                  70                  75                  80

Gly Gln Gln Ala Ala Cys Asp Met Ala Ala Leu Glu Asp Val Asp Gln
                85                  90                  95

Val Met Ala Ala Ile Val Gly Ala Ala Gly Leu Leu Pro Thr Leu Ala
            100                 105                 110

Ala Ile Arg Ala Gly Lys Thr Ile Leu Leu Ala Asn Lys Glu Ser Leu
        115                 120                 125

Val Thr Cys Gly Arg Leu Phe Met Asp Ala Val Lys Gln Ser Lys Ala
    130                 135                 140

Gln Leu Leu Pro Val Asp Ser Glu His Asn Ala Ile Phe Gln Ser Leu
145                 150                 155                 160

Pro Gln Pro Ile Gln His Asn Leu Gly Tyr Ala Asp Leu Glu Gln Asn
                165                 170                 175

Gly Val Val Ser Ile Leu Leu Thr Gly Ser Gly Gly Pro Phe Arg Glu
            180                 185                 190

Thr Pro Leu Arg Asp Leu Ala Thr Met Thr Pro Asp Gln Ala Cys Arg
        195                 200                 205

His Pro Asn Trp Ser Met Gly Arg Lys Ile Ser Val Asp Ser Ala Thr
    210                 215                 220

Met Met Asn Lys Gly Leu Glu Tyr Ile Glu Ala Arg Trp Leu Phe Asn
225                 230                 235                 240

Ala Ser Ala Ser Gln Met Glu Val Leu Ile His Pro Gln Ser Val Ile
                245                 250                 255

His Ser Met Val Arg Tyr Gln Asp Gly Ser Val Leu Ala Gln Leu Gly
            260                 265                 270

Glu Pro Asp Met Arg Thr Pro Ile Ala His Thr Met Ala Trp Pro Asn
        275                 280                 285

Arg Val Asn Ser Gly Val Lys Pro Leu Asp Phe Cys Lys Leu Ser Ala
    290                 295                 300

Leu Thr Phe Ala Ala Pro Asp Tyr Asp Arg Tyr Pro Cys Leu Lys Leu
305                 310                 315                 320

Ala Met Glu Ala Phe Glu Gln Gly Gln Ala Ala Thr Thr Ala Leu Asn
                325                 330                 335

Ala Ala Asn Glu Ile Thr Val Ala Ala Phe Leu Ala Gln Gln Ile Arg
            340                 345                 350

Phe Thr Asp Ile Ala Ala Leu Asn Leu Ser Val Leu Glu Lys Met Asp

```
                        355                 360                 365
Met Arg Glu Pro Gln Cys Val Asp Asp Val Leu Ser Val Asp Ala Asn
            370                 375                 380

Ala Arg Glu Val Ala Arg Lys Glu Val Met Arg Leu Ala Ser
385                 390                 395

<210> SEQ ID NO 5
<211> LENGTH: 236
<212> TYPE: PRT
<213> ORGANISM: E. coli

<400> SEQUENCE: 5

Met Ala Thr Thr His Leu Asp Val Cys Ala Val Val Pro Ala Ala Gly
1               5                   10                  15

Phe Gly Arg Arg Met Gln Thr Glu Cys Pro Lys Gln Tyr Leu Ser Ile
            20                  25                  30

Gly Asn Gln Thr Ile Leu Glu His Ser Val His Ala Leu Leu Ala His
        35                  40                  45

Pro Arg Val Lys Arg Val Val Ile Ala Ile Ser Pro Gly Asp Ser Arg
    50                  55                  60

Phe Ala Gln Leu Pro Leu Ala Asn His Pro Gln Ile Thr Val Val Asp
65                  70                  75                  80

Gly Gly Asp Glu Arg Ala Asp Ser Val Leu Ala Gly Leu Lys Ala Ala
                85                  90                  95

Gly Asp Ala Gln Trp Val Leu Val His Asp Ala Ala Arg Pro Cys Leu
            100                 105                 110

His Gln Asp Asp Leu Ala Arg Leu Leu Ala Leu Ser Glu Thr Ser Arg
        115                 120                 125

Thr Gly Gly Ile Leu Ala Ala Pro Val Arg Asp Thr Met Lys Arg Ala
    130                 135                 140

Glu Pro Gly Lys Asn Ala Ile Ala His Thr Val Asp Arg Asn Gly Leu
145                 150                 155                 160

Trp His Ala Leu Thr Pro Gln Phe Phe Pro Arg Glu Leu Leu His Asp
                165                 170                 175

Cys Leu Thr Arg Ala Leu Asn Glu Gly Ala Thr Ile Thr Asp Glu Ala
            180                 185                 190

Ser Ala Leu Glu Tyr Cys Gly Phe His Pro Gln Leu Val Glu Gly Arg
        195                 200                 205

Ala Asp Asn Ile Lys Val Thr Arg Pro Glu Asp Leu Ala Leu Ala Glu
    210                 215                 220

Phe Tyr Leu Thr Arg Thr Ile His Gln Glu Asn Thr
225                 230                 235

<210> SEQ ID NO 6
<211> LENGTH: 283
<212> TYPE: PRT
<213> ORGANISM: E. coli

<400> SEQUENCE: 6

Met Arg Thr Gln Trp Pro Ser Pro Ala Lys Leu Asn Leu Phe Leu Tyr
1               5                   10                  15

Ile Thr Gly Gln Arg Ala Asp Gly Tyr His Thr Leu Gln Thr Leu Phe
            20                  25                  30

Gln Phe Leu Asp Tyr Gly Asp Thr Ile Ser Ile Glu Leu Arg Asp Asp
        35                  40                  45

Gly Asp Ile Arg Leu Leu Thr Pro Val Glu Gly Val Glu His Glu Asp
```

```
            50                  55                  60
Asn Leu Ile Val Arg Ala Ala Arg Leu Leu Met Lys Thr Ala Ala Asp
 65                  70                  75                  80

Ser Gly Arg Leu Pro Thr Gly Ser Gly Ala Asn Ile Ser Ile Asp Lys
                     85                  90                  95

Arg Leu Pro Met Gly Gly Gly Leu Gly Gly Ser Ser Asn Ala Ala
                100                 105                 110

Thr Val Leu Val Ala Leu Asn His Leu Trp Gln Cys Gly Leu Ser Met
                115                 120                 125

Asp Glu Leu Ala Glu Met Gly Leu Thr Leu Gly Ala Asp Val Pro Val
                130                 135                 140

Phe Val Arg Gly His Ala Ala Phe Ala Glu Gly Val Gly Glu Ile Leu
145                 150                 155                 160

Thr Pro Val Asp Pro Pro Glu Lys Trp Tyr Leu Val Ala His Pro Gly
                165                 170                 175

Val Ser Ile Pro Thr Pro Val Ile Phe Lys Asp Pro Glu Leu Pro Arg
                180                 185                 190

Asn Thr Pro Lys Arg Ser Ile Glu Thr Leu Leu Lys Cys Glu Phe Ser
                195                 200                 205

Asn Asp Cys Glu Val Ile Ala Arg Lys Arg Phe Arg Glu Val Asp Ala
210                 215                 220

Val Leu Ser Trp Leu Leu Glu Tyr Ala Pro Ser Arg Leu Thr Gly Thr
225                 230                 235                 240

Gly Ala Cys Val Phe Ala Glu Phe Asp Thr Glu Ser Glu Ala Arg Gln
                245                 250                 255

Val Leu Glu Gln Ala Pro Glu Trp Leu Asn Gly Phe Val Ala Lys Gly
                260                 265                 270

Ala Asn Leu Ser Pro Leu His Arg Ala Met Leu
                275                 280

<210> SEQ ID NO 7
<211> LENGTH: 159
<212> TYPE: PRT
<213> ORGANISM: E. coli

<400> SEQUENCE: 7

Met Arg Ile Gly His Gly Phe Asp Val His Ala Phe Gly Gly Glu Gly
  1               5                  10                  15

Pro Ile Ile Ile Gly Gly Val Arg Ile Pro Tyr Glu Lys Gly Leu Leu
                 20                  25                  30

Ala His Ser Asp Gly Asp Val Ala Leu His Ala Leu Thr Asp Ala Leu
                 35                  40                  45

Leu Gly Ala Ala Ala Leu Gly Asp Ile Gly Lys Leu Phe Pro Asp Thr
 50                  55                  60

Asp Pro Ala Phe Lys Gly Ala Asp Ser Arg Glu Leu Leu Arg Glu Ala
 65                  70                  75                  80

Trp Arg Arg Ile Gln Ala Lys Gly Tyr Thr Leu Gly Asn Val Asp Val
                 85                  90                  95

Thr Ile Ile Ala Gln Ala Pro Lys Met Leu Pro His Ile Pro Gln Met
                100                 105                 110

Arg Val Phe Ile Ala Glu Asp Leu Gly Cys His Met Asp Asp Val Asn
                115                 120                 125

Val Lys Ala Thr Thr Thr Glu Lys Leu Gly Phe Thr Gly Arg Gly Glu
                130                 135                 140
```

Gly Ile Ala Cys Glu Ala Val Ala Leu Leu Ile Lys Ala Thr Lys
145                 150                 155

<210> SEQ ID NO 8
<211> LENGTH: 182
<212> TYPE: PRT
<213> ORGANISM: E. coli

<400> SEQUENCE: 8

Met Gln Thr Glu His Val Ile Leu Leu Asn Ala Gln Gly Val Pro Thr
1               5                   10                  15

Gly Thr Leu Glu Lys Tyr Ala Ala His Thr Ala Asp Thr Arg Leu His
            20                  25                  30

Leu Ala Phe Ser Ser Trp Leu Phe Asn Ala Lys Gly Gln Leu Leu Val
        35                  40                  45

Thr Arg Arg Ala Leu Ser Lys Lys Ala Trp Pro Gly Val Trp Thr Asn
50                  55                  60

Ser Val Cys Gly His Pro Gln Leu Gly Glu Ser Asn Glu Asp Ala Val
65                  70                  75                  80

Ile Arg Arg Cys Arg Tyr Glu Leu Gly Val Glu Ile Thr Pro Pro Glu
                85                  90                  95

Ser Ile Tyr Pro Asp Phe Arg Tyr Arg Ala Thr Asp Pro Ser Gly Ile
            100                 105                 110

Val Glu Asn Glu Val Cys Pro Val Phe Ala Ala Arg Thr Thr Ser Ala
        115                 120                 125

Leu Gln Ile Asn Asp Asp Glu Val Met Asp Tyr Gln Trp Cys Asp Leu
130                 135                 140

Ala Asp Val Leu His Gly Ile Asp Ala Thr Pro Trp Ala Phe Ser Pro
145                 150                 155                 160

Trp Met Val Met Gln Ala Thr Asn Arg Glu Ala Arg Lys Arg Leu Ser
                165                 170                 175

Ala Phe Thr Gln Leu Lys
            180

<210> SEQ ID NO 9
<211> LENGTH: 1174
<212> TYPE: PRT
<213> ORGANISM: E. coli

<400> SEQUENCE: 9

Met Ile Thr Ile Asp Gly Asn Gly Ala Val Ala Ser Val Ala Phe Arg
1               5                   10                  15

Thr Ser Glu Val Ile Ala Ile Tyr Pro Ile Thr Pro Ser Ser Thr Met
            20                  25                  30

Ala Glu Gln Ala Asp Ala Trp Ala Gly Asn Gly Leu Lys Asn Val Trp
        35                  40                  45

Gly Asp Thr Pro Arg Val Val Glu Met Gln Ser Glu Ala Gly Ala Ile
50                  55                  60

Ala Thr Val His Gly Ala Leu Gln Thr Gly Ala Leu Ser Thr Ser Phe
65                  70                  75                  80

Thr Ser Ser Gln Gly Leu Leu Leu Met Ile Pro Thr Leu Tyr Lys Leu
                85                  90                  95

Ala Gly Glu Leu Thr Pro Phe Val Leu His Val Ala Ala Arg Thr Val
            100                 105                 110

Ala Thr His Ala Leu Ser Ile Phe Gly Asp His Ser Asp Val Met Ala
        115                 120                 125

```
Val Arg Gln Thr Gly Cys Ala Met Leu Cys Ala Ala Asn Val Gln Glu
130                 135                 140

Ala Gln Asp Phe Ala Leu Ile Ser Gln Ile Ala Thr Leu Lys Ser Arg
145                 150                 155                 160

Val Pro Phe Ile His Phe Phe Asp Gly Phe Arg Thr Ser His Glu Ile
                165                 170                 175

Asn Lys Ile Val Pro Leu Ala Asp Asp Thr Ile Leu Asp Leu Met Pro
            180                 185                 190

Gln Val Glu Ile Asp Ala His Arg Ala Arg Ala Leu Asn Pro Glu His
        195                 200                 205

Pro Val Ile Arg Gly Thr Ser Ala Asn Pro Asp Thr Tyr Phe Gln Ser
210                 215                 220

Arg Glu Ala Thr Asn Pro Trp Tyr Asn Ala Val Tyr Asp His Val Glu
225                 230                 235                 240

Gln Ala Met Asn Asp Phe Ser Ala Ala Thr Gly Arg Gln Tyr Gln Pro
                245                 250                 255

Phe Glu Tyr Tyr Gly His Pro Gln Ala Glu Arg Val Ile Ile Leu Met
            260                 265                 270

Gly Ser Ala Ile Gly Thr Cys Glu Glu Val Val Asp Glu Leu Leu Thr
        275                 280                 285

Arg Gly Glu Lys Val Gly Val Leu Lys Val Arg Leu Tyr Arg Pro Phe
290                 295                 300

Ser Ala Lys His Leu Leu Gln Ala Leu Pro Gly Ser Val Arg Ser Val
305                 310                 315                 320

Ala Val Leu Asp Arg Thr Lys Glu Pro Gly Ala Gln Ala Glu Pro Leu
                325                 330                 335

Tyr Leu Asp Val Met Thr Ala Leu Ala Glu Ala Phe Asn Asn Gly Glu
            340                 345                 350

Arg Glu Thr Leu Pro Arg Val Ile Gly Gly Arg Tyr Gly Leu Ser Ser
        355                 360                 365

Lys Glu Phe Gly Pro Asp Cys Val Leu Ala Val Phe Ala Glu Leu Asn
370                 375                 380

Ala Ala Lys Pro Lys Ala Arg Phe Thr Val Gly Ile Tyr Asp Asp Val
385                 390                 395                 400

Thr Asn Leu Ser Leu Pro Leu Pro Glu Asn Thr Leu Pro Asn Ser Ala
                405                 410                 415

Lys Leu Glu Ala Leu Phe Tyr Gly Leu Gly Ser Asp Gly Ser Val Ser
            420                 425                 430

Ala Thr Lys Asn Asn Ile Lys Ile Ile Gly Asn Ser Thr Pro Trp Tyr
        435                 440                 445

Ala Gln Gly Tyr Phe Val Tyr Asp Ser Lys Lys Ala Gly Gly Leu Thr
450                 455                 460

Val Ser His Leu Arg Val Ser Glu Gln Pro Ile Arg Ser Ala Tyr Leu
465                 470                 475                 480

Ile Ser Gln Ala Asp Phe Val Gly Cys His Gln Leu Gln Phe Ile Asp
                485                 490                 495

Lys Tyr Gln Met Ala Glu Arg Leu Lys Pro Gly Gly Ile Phe Leu Leu
            500                 505                 510

Asn Thr Pro Tyr Ser Ala Asp Glu Val Trp Ser Arg Leu Pro Gln Glu
        515                 520                 525

Val Gln Ala Val Leu Asn Gln Lys Ala Arg Phe Tyr Val Ile Asn
530                 535                 540

Ala Ala Lys Ile Ala Arg Glu Cys Gly Leu Ala Ala Arg Ile Asn Thr
```

-continued

```
            545                 550                 555                 560
Val Met Gln Met Ala Phe Phe His Leu Thr Gln Ile Leu Pro Gly Asp
                565                 570                 575
Ser Ala Leu Ala Glu Leu Gln Gly Ala Ile Ala Lys Ser Tyr Ser Ser
                580                 585                 590
Lys Gly Gln Asp Leu Val Glu Arg Asn Trp Gln Ala Leu Ala Leu Ala
                595                 600                 605
Arg Glu Ser Val Glu Glu Val Pro Leu Gln Pro Val Asn Pro His Ser
            610                 615                 620
Ala Asn Arg Pro Pro Val Val Ser Asp Ala Ala Pro Asp Phe Val Lys
625                 630                 635                 640
Thr Val Thr Ala Ala Met Leu Ala Gly Leu Gly Asp Ala Leu Pro Val
                645                 650                 655
Ser Ala Leu Pro Pro Asp Gly Thr Trp Pro Met Gly Thr Thr Arg Trp
                660                 665                 670
Glu Lys Arg Asn Ile Ala Glu Glu Ile Pro Ile Trp Lys Glu Glu Leu
                675                 680                 685
Cys Thr Gln Cys Asn His Cys Val Ala Ala Cys Pro His Ser Ala Ile
            690                 695                 700
Arg Ala Lys Val Val Pro Glu Ala Met Glu Asn Ala Pro Ala Ser
705                 710                 715                 720
Leu His Ser Leu Asp Val Lys Ser Arg Asp Met Arg Gly Gln Lys Tyr
                725                 730                 735
Val Leu Gln Val Ala Pro Glu Asp Cys Thr Gly Cys Asn Leu Cys Val
                740                 745                 750
Glu Val Cys Pro Ala Lys Asp Arg Gln Asn Pro Glu Ile Lys Ala Ile
            755                 760                 765
Asn Met Met Ser Arg Leu Glu His Val Glu Glu Lys Ile Asn Tyr
            770                 775                 780
Asp Phe Phe Leu Asn Leu Pro Glu Ile Asp Arg Ser Lys Leu Glu Arg
785                 790                 795                 800
Ile Asp Ile Arg Thr Ser Gln Leu Ile Thr Pro Leu Phe Glu Tyr Ser
                805                 810                 815
Gly Ala Cys Ser Gly Cys Gly Glu Thr Pro Tyr Ile Lys Leu Leu Thr
                820                 825                 830
Gln Leu Tyr Gly Asp Arg Met Leu Ile Ala Asn Ala Thr Gly Cys Ser
                835                 840                 845
Ser Ile Tyr Gly Gly Asn Leu Pro Ser Thr Pro Tyr Thr Thr Asp Ala
            850                 855                 860
Asn Gly Arg Gly Pro Ala Trp Ala Asn Ser Leu Phe Glu Asp Asn Ala
865                 870                 875                 880
Glu Phe Gly Leu Gly Phe Arg Leu Thr Val Asp Gln His Arg Val Arg
                885                 890                 895
Val Leu Arg Leu Leu Asp Gln Phe Ala Asp Lys Ile Pro Ala Glu Leu
                900                 905                 910
Leu Thr Ala Leu Lys Ser Asp Ala Thr Pro Glu Val Arg Arg Glu Gln
                915                 920                 925
Val Ala Ala Leu Arg Gln Gln Leu Asn Asp Val Ala Glu Ala His Glu
            930                 935                 940
Leu Leu Arg Asp Ala Asp Ala Leu Val Glu Lys Ser Ile Trp Leu Ile
945                 950                 955                 960
Gly Gly Asp Gly Trp Ala Tyr Asp Ile Gly Phe Gly Gly Leu Asp His
                965                 970                 975
```

```
Val Leu Ser Leu Thr Glu Asn Val Asn Ile Leu Val Leu Asp Thr Gln
                980                 985                 990

Cys Tyr Ser Asn Thr Gly Gly Gln  Ala Ser Lys Ala Thr  Pro Leu Gly
            995                 1000                 1005

Ala Val Thr Lys Phe Gly Glu  His Gly Lys Arg Lys  Ala Arg Lys
            1010                 1015                 1020

Asp Leu Gly Val Ser Met Met  Met Tyr Gly His Val  Tyr Val Ala
            1025                 1030                 1035

Gln Ile Ser Leu Gly Ala Gln  Leu Asn Gln Thr Val  Lys Ala Ile
            1040                 1045                 1050

Gln Glu Ala Glu Ala Tyr Pro  Gly Pro Ser Leu Ile  Ile Ala Tyr
            1055                 1060                 1065

Ser Pro Cys Glu Glu His Gly  Tyr Asp Leu Ala Leu  Ser His Asp
            1070                 1075                 1080

Gln Met Arg Gln Leu Thr Ala  Thr Gly Phe Trp Pro  Leu Tyr Arg
            1085                 1090                 1095

Phe Asp Pro Arg Arg Ala Asp  Glu Gly Lys Leu Pro  Leu Ala Leu
            1100                 1105                 1110

Asp Ser Arg Pro Pro Ser Glu  Ala Pro Glu Glu Thr  Leu Leu His
            1115                 1120                 1125

Glu Gln Arg Phe Arg Arg Leu  Asn Ser Gln Gln Pro  Glu Val Ala
            1130                 1135                 1140

Glu Gln Leu Trp Lys Asp Ala  Ala Ala Asp Leu Gln  Lys Arg Tyr
            1145                 1150                 1155

Asp Phe Leu Ala Gln Met Ala  Gly Lys Ala Glu Lys  Ser Asn Thr
            1160                 1165                 1170

Asp

<210> SEQ ID NO 10
<211> LENGTH: 56
<212> TYPE: PRT
<213> ORGANISM: Clostridium pasteurianum

<400> SEQUENCE: 10

Met Ala Tyr Lys Ile Ala Asp Ser Cys Val Ser Cys Gly Ala Cys Ala
1               5                   10                  15

Ser Glu Cys Pro Val Asn Ala Ile Ser Gln Gly Asp Ser Ile Phe Val
                20                  25                  30

Ile Asp Ala Asp Thr Cys Ile Asp Cys Gly Asn Cys Ala Asn Val Cys
            35                  40                  45

Pro Val Gly Ala Pro Val Gln Glu
        50                  55

<210> SEQ ID NO 11
<211> LENGTH: 254
<212> TYPE: PRT
<213> ORGANISM: E. coli

<400> SEQUENCE: 11

Met Arg Ser Ile Ala Arg Arg Thr Ala Val Gly Ala Ala Leu Leu Leu
1               5                   10                  15

Val Met Pro Val Ala Val Trp Ile Ser Gly Trp Arg Trp Gln Pro Gly
                20                  25                  30

Glu Gln Ser Trp Leu Leu Lys Ala Ala Phe Trp Val Thr Glu Thr Val
            35                  40                  45
```

```
Thr Gln Pro Trp Gly Val Ile Thr His Leu Ile Leu Phe Gly Trp Phe
    50                  55                  60

Leu Trp Cys Leu Arg Phe Arg Ile Lys Ala Ala Phe Val Leu Phe Ala
 65              70                  75                      80

Ile Leu Ala Ala Ala Ile Leu Val Gly Gln Gly Val Lys Ser Trp Ile
                85                  90                  95

Lys Asp Lys Val Gln Glu Pro Arg Pro Phe Val Ile Trp Leu Glu Lys
            100                 105                 110

Thr His His Ile Pro Val Asp Glu Phe Tyr Thr Leu Lys Arg Ala Glu
                115                 120                 125

Arg Gly Asn Leu Val Lys Glu Gln Leu Ala Glu Lys Asn Ile Pro
        130                 135                 140

Gln Tyr Leu Arg Ser His Trp Gln Lys Glu Thr Gly Phe Ala Phe Pro
145                 150                 155                 160

Ser Gly His Thr Met Phe Ala Ala Ser Trp Ala Leu Ala Val Gly
                165                 170                 175

Leu Leu Trp Pro Arg Arg Thr Leu Thr Ile Ala Ile Leu Leu Val
        180                 185                 190

Trp Ala Thr Gly Val Met Gly Ser Arg Leu Leu Gly Met His Trp
        195                 200                 205

Pro Arg Asp Leu Val Val Ala Thr Leu Ile Ser Trp Ala Leu Val Ala
210                 215                 220

Val Ala Thr Trp Leu Ala Gln Arg Ile Cys Gly Pro Leu Thr Pro Pro
225                 230                 235                 240

Ala Glu Glu Asn Arg Glu Ile Ala Gln Arg Glu Gln Glu Ser
                245                 250

<210> SEQ ID NO 12
<211> LENGTH: 150
<212> TYPE: PRT
<213> ORGANISM: E. coli

<400> SEQUENCE: 12

Met Lys Asp Lys Val Tyr Lys Arg Pro Val Ser Ile Leu Val Val Ile
 1               5                  10                  15

Tyr Ala Gln Asp Thr Lys Arg Val Leu Met Leu Gln Arg Arg Asp Asp
                20                  25                  30

Pro Asp Phe Trp Gln Ser Val Thr Gly Ser Val Glu Glu Gly Glu Thr
            35                  40                  45

Ala Pro Gln Ala Ala Met Arg Glu Val Lys Glu Glu Val Thr Ile Asp
         50                 55                  60

Val Val Ala Glu Gln Leu Thr Leu Ile Asp Cys Gln Arg Thr Val Glu
 65                 70                  75                  80

Phe Glu Ile Phe Ser His Leu Arg His Arg Tyr Ala Pro Gly Val Thr
                 85                 90                  95

Arg Asn Thr Glu Ser Trp Phe Cys Leu Ala Leu Pro His Glu Arg Gln
            100                 105                 110

Ile Val Phe Thr Glu His Leu Ala Tyr Lys Trp Leu Asp Ala Pro Ala
            115                 120                 125

Ala Ala Ala Leu Thr Lys Ser Trp Ser Asn Arg Gln Ala Ile Glu Gln
            130                 135                 140

Phe Val Ile Asn Ala Ala
145                 150

<210> SEQ ID NO 13
```

<211> LENGTH: 6
<212> TYPE: PRT
<213> ORGANISM: E. coli

<400> SEQUENCE: 13

Ala Gly Gly Ala Gly Gly
1               5

<210> SEQ ID NO 14
<211> LENGTH: 613
<212> TYPE: PRT
<213> ORGANISM: Methanococcus maripaludis

<400> SEQUENCE: 14

Met Asn Ile Leu Ile Asp Gly Ser Arg Gln Asn Tyr Glu Glu Leu Glu
1               5                   10                  15

Glu Ser Glu Phe Pro Ile Ser Phe Gly Ile Asn Leu His Thr Lys Gln
            20                  25                  30

Glu Thr Trp Lys Tyr Asp Ala Phe Asp Glu Lys Asn Leu Phe Cys Phe
        35                  40                  45

Gly Lys Gly Ile Leu Pro Ile Ile Gly Gly His Arg Leu Ile Phe Ser
    50                  55                  60

Phe Arg Ser Pro Leu Trp Asp Gly Phe His Phe Ser Ala Met Gly Gly
65                  70                  75                  80

Ala Gly Tyr Thr Phe Lys Asp Thr Gly Ile Gln Asn Val Ala Ile Thr
                85                  90                  95

Gly Lys Cys Glu Val Pro Thr Val Ile Val Leu Asn Gly Glu Glu Asp
            100                 105                 110

Lys Leu Lys Ile Glu Phe Met Pro Phe Thr Glu Glu Ile Thr Asp Ile
        115                 120                 125

Tyr Glu Phe Asn Asp Lys Ile Ile Asp Leu Phe Lys Glu Lys Asn Tyr
    130                 135                 140

Arg Ala Phe Leu Val Gly Pro Ala Ser Lys Thr Thr Asn Met Gly Gly
145                 150                 155                 160

Ile Tyr Ser Gln Thr Ile Arg Asn Gly Lys Ile Val Glu Gly Ser Glu
                165                 170                 175

Asp Trp Ala Ala Arg Gly Gly Gly Ser Val Leu Tyr Gln Ala His
            180                 185                 190

Asn Val Leu Gly Val Val Phe Phe Gly Lys Lys Thr Pro Glu Lys Asn
        195                 200                 205

Leu Lys Glu Ile Val Glu Glu His Tyr Asn Lys Pro Tyr Thr Lys Val
    210                 215                 220

Val Leu Glu His Thr Glu Lys Tyr Arg Tyr Ser Glu Glu Lys Lys Thr
225                 230                 235                 240

Gly Gly Thr Phe Gly Asn Asn Tyr His Val Thr Met Glu Leu Thr Pro
                245                 250                 255

Val Phe Asn Trp Arg Met Pro Phe Ile Asp Lys Asn Lys Arg Met Lys
            260                 265                 270

Leu His Lys Lys Ile Ile Glu Tyr Phe Val Asn Arg Phe Asp Glu Glu
        275                 280                 285

Ala Ile Glu Thr Lys Asn Trp Thr Asn Cys Gly Glu Pro Cys Pro Val
    290                 295                 300

Val Cys Lys Lys Tyr Arg Lys Gly Leu His Val Asp Tyr Glu Pro Tyr
305                 310                 315                 320

Glu Ala Asn Gly Pro Cys Ile Gly Val Phe Asp Ile Tyr Ala Ala Asp
                325                 330                 335

```
Lys Val Val His Thr Ile Asp Lys Leu Gly Phe Asp Ala Ile Glu Phe
                340                 345                 350

Gly Asn Leu Cys Ser Trp Thr Phe Glu Leu Leu Asp Asn Gly Met Leu
            355                 360                 365

Lys Pro Glu Glu Val Gly Ile Glu Lys Pro Val Phe Asp Ile Ser Asn
370                 375                 380

Phe Glu Asn Asp Glu Asp Ile Leu Lys Asn Ser Met His Asn Ala Glu
385                 390                 395                 400

Gln Ala Val Lys Leu Ala Glu Ile Ile Ala Phe Gln Thr Asn Glu Phe
                405                 410                 415

Gly Lys Ile Cys Lys Ser Gly Thr Arg Arg Ala Gly Lys Ile Leu Asn
            420                 425                 430

Glu Lys Tyr Pro Asp Arg Ile Lys Asp Lys Lys Phe Glu Asp Phe Gly
        435                 440                 445

Val Tyr Asp Ser Phe Gly Glu Arg Gly Gln Ile Ser Pro Thr Met Tyr
    450                 455                 460

Trp Ala Ile Gly Asn Phe Met Pro Tyr Leu Ile Gln Gly Lys Tyr Leu
465                 470                 475                 480

Thr His Tyr Gln Cys Gly Val Phe Leu Glu Pro Glu Glu Leu Ala Glu
                485                 490                 495

Leu Ser Val Lys Asn Ser Ile Glu Ile Thr Leu Gly Asn Leu Gly
            500                 505                 510

Ile Cys Arg Phe His Arg Lys Trp Val Thr Pro Ile Ile Glu Lys Leu
        515                 520                 525

Val Lys Glu Met Ser Asp Val Asn Leu Asn Glu Ser Met Glu Leu
    530                 535                 540

Phe Lys Lys Ile Ala Lys Tyr Asp Ser Asn Ile Gly Cys Pro Glu Met
545                 550                 555                 560

Glu Ser Glu Arg Val Lys Glu Leu Ile Ile Ala Gly Ala Phe Glu Phe
                565                 570                 575

Glu Asn Glu Lys Trp Ser Lys Glu Phe Glu Asn Gly Asn Phe Asp Glu
            580                 585                 590

Tyr Ile Lys Arg Val Leu Glu Lys Tyr Ser Glu Leu Leu Glu Ile Asp
        595                 600                 605

Trp Lys Leu Lys Glu
    610

<210> SEQ ID NO 15
<211> LENGTH: 54
<212> TYPE: PRT
<213> ORGANISM: Heliobacterium modesticaldum

<400> SEQUENCE: 15

Met Ala Tyr Lys Ile Thr Asp Ala Cys Thr Ala Cys Gly Ala Cys Met
1               5                   10                  15

Asp Gly Cys Cys Val Gly Ala Ile Val Glu Gly Lys Lys Tyr Ser Ile
            20                  25                  30

Thr Ser Asp Cys Val Asp Cys Gly Val Cys Ala Asp Lys Cys Pro Val
        35                  40                  45

Asp Ala Ile Ile Pro Gly
    50

<210> SEQ ID NO 16
<211> LENGTH: 83
<212> TYPE: PRT
```

<213> ORGANISM: Pseudomonas aeruginosa

<400> SEQUENCE: 16

Met Ser Leu Lys Ile Thr Asp Asp Cys Ile Asn Cys Asp Val Cys Glu
1               5                   10                  15

Pro Glu Cys Pro Asn Gly Ala Ile Ser Gln Gly Glu Glu Ile Tyr Val
                20                  25                  30

Ile Asp Pro Asn Leu Cys Thr Glu Cys Val Gly His Tyr Asp Glu Pro
            35                  40                  45

Gln Cys Gln Gln Val Cys Pro Val Asp Cys Ile Pro Leu Asp Asp Ala
        50                  55                  60

Asn Val Glu Ser Lys Asp Gln Leu Met Glu Lys Tyr Arg Lys Ile Thr
65                  70                  75                  80

Gly Lys Ala

<210> SEQ ID NO 17
<211> LENGTH: 83
<212> TYPE: PRT
<213> ORGANISM: Allochromatium vinosum

<400> SEQUENCE: 17

Met Ala Leu Met Ile Thr Asp Glu Cys Ile Asn Cys Asp Val Cys Glu
1               5                   10                  15

Pro Glu Cys Pro Asn Gly Ala Ile Ser Gln Gly Asp Glu Thr Tyr Val
                20                  25                  30

Ile Glu Pro Ser Leu Cys Thr Glu Cys Val Gly His Tyr Glu Thr Ser
            35                  40                  45

Gln Cys Val Glu Val Cys Pro Val Asp Cys Ile Ile Lys Asp Pro Ser
        50                  55                  60

His Glu Glu Thr Glu Asp Glu Leu Arg Ala Lys Tyr Glu Arg Ile Thr
65                  70                  75                  80

Gly Glu Gly

<210> SEQ ID NO 18
<211> LENGTH: 83
<212> TYPE: PRT
<213> ORGANISM: Artificial Sequence
<220> FEATURE:
<223> OTHER INFORMATION: Synthetic Polypeptide

<400> SEQUENCE: 18

Met Ala Leu Met Ile Thr Asp Glu Cys Ile Asn Cys Asp Val Cys Glu
1               5                   10                  15

Pro Glu Cys Pro Asn Gly Ala Ile Ser Gln Gly Asp Glu Thr Tyr Val
                20                  25                  30

Ile Glu Pro Ser Leu Cys Thr Glu Cys Val Gly His Tyr Glu Thr Ser
            35                  40                  45

Gln Cys Val Glu Val Cys Pro Val Asp Ala Ile Ile Lys Asp Pro Ser
        50                  55                  60

His Glu Glu Thr Glu Asp Glu Leu Arg Ala Lys Tyr Glu Arg Ile Thr
65                  70                  75                  80

Gly Glu Gly

<210> SEQ ID NO 19
<211> LENGTH: 86
<212> TYPE: PRT
<213> ORGANISM: E. coli

```
<400> SEQUENCE: 19

Met Ala Leu Leu Ile Thr Lys Lys Cys Ile Asn Cys Asp Met Cys Glu
1               5                   10                  15

Pro Glu Cys Pro Asn Glu Ala Ile Ser Met Gly Asp His Ile Tyr Glu
            20                  25                  30

Ile Asn Ser Asp Lys Cys Thr Glu Cys Val Gly His Tyr Glu Thr Pro
        35                  40                  45

Thr Cys Gln Lys Val Cys Pro Ile Pro Asn Thr Ile Val Lys Asp Pro
    50                  55                  60

Ala His Val Glu Thr Glu Gln Leu Trp Asp Lys Phe Val Leu Met
65                  70                  75                  80

His His Ala Asp Lys Ile
                85

<210> SEQ ID NO 20
<211> LENGTH: 56
<212> TYPE: PRT
<213> ORGANISM: Clostridium acetobutylicum

<400> SEQUENCE: 20

Met Ala Tyr Lys Ile Thr Asp Ala Cys Val Ser Cys Gly Ser Cys Ala
1               5                   10                  15

Ser Glu Cys Pro Val Ser Ala Ile Ser Gln Gly Asp Thr Gln Phe Val
            20                  25                  30

Ile Asp Ala Asp Thr Cys Ile Glu Cys Gly Asn Cys Ala Asn Val Cys
        35                  40                  45

Pro Val Gly Ala Pro Val Gln Glu
    50                  55

<210> SEQ ID NO 21
<211> LENGTH: 111
<212> TYPE: PRT
<213> ORGANISM: E. coli

<400> SEQUENCE: 21

Met Pro Lys Ile Val Ile Leu Pro His Gln Asp Leu Cys Pro Asp Gly
1               5                   10                  15

Ala Val Leu Glu Ala Asn Ser Gly Glu Thr Ile Leu Asp Ala Ala Leu
            20                  25                  30

Arg Asn Gly Ile Glu Ile Glu His Ala Cys Glu Lys Ser Cys Ala Cys
        35                  40                  45

Thr Thr Cys His Cys Ile Val Arg Glu Gly Phe Asp Ser Leu Pro Glu
    50                  55                  60

Ser Ser Glu Gln Glu Asp Asp Met Leu Asp Lys Ala Trp Gly Leu Glu
65                  70                  75                  80

Pro Glu Ser Arg Leu Ser Cys Gln Ala Arg Val Thr Asp Glu Asp Leu
            85                  90                  95

Val Val Glu Ile Pro Arg Tyr Thr Ile Asn His Ala Arg Glu His
            100                 105                 110

<210> SEQ ID NO 22
<211> LENGTH: 71
<212> TYPE: PRT
<213> ORGANISM: Ectothiorhodospira shaposhnikovii

<400> SEQUENCE: 22

Met Glu Arg Leu Ser Glu Asp Asp Pro Ala Ala Gln Ala Leu Glu Tyr
1               5                   10                  15
```

Arg His Asp Ala Ser Ser Val Gln His Pro Ala Tyr Glu Glu Gly Gln
                20                  25                  30

Thr Cys Leu Asn Cys Leu Leu Tyr Thr Asp Ala Ser Ala Gln Asp Trp
            35                  40                  45

Gly Pro Cys Ser Val Phe Pro Gly Lys Leu Val Ser Ala Asn Gly Trp
50                  55                  60

Cys Thr Ala Trp Val Ala Arg
65                  70

<210> SEQ ID NO 23
<211> LENGTH: 83
<212> TYPE: PRT
<213> ORGANISM: Pseudomonas putida

<400> SEQUENCE: 23

Met Ser Leu Ile Ile Thr Asp Asp Cys Ile Asn Cys Asp Val Cys Glu
1               5                   10                  15

Pro Glu Cys Pro Asn Ala Ala Ile Ser Gln Gly Glu Glu Ile Tyr Val
                20                  25                  30

Ile Asp Pro Asn Leu Cys Thr Gln Cys Val Gly His Tyr Asp Glu Pro
            35                  40                  45

Gln Cys Gln Gln Val Cys Pro Val Asp Cys Ile Pro Leu Asp Glu Ala
        50                  55                  60

His Pro Glu Thr His Asp Glu Leu Met Glu Lys Tyr Lys Arg Ile Thr
65                  70                  75                  80

Gly Lys Ala

<210> SEQ ID NO 24
<211> LENGTH: 80
<212> TYPE: PRT
<213> ORGANISM: Pseudomonas putida

<400> SEQUENCE: 24

Met Ser Leu Ile Ile Thr Asp Asp Cys Ile Asn Cys Asp Val Cys Glu
1               5                   10                  15

Pro Glu Cys Pro Asn Glu Ala Ile Ser Gln Gly Glu Glu Ile Tyr Val
                20                  25                  30

Ile Asp Pro Asn Leu Cys Thr Gln Cys Val Gly His Tyr Asp Glu Pro
            35                  40                  45

Gln Cys Gln Gln Val Cys Pro Val Asp Cys Ile Pro Leu Asp Glu Ala
        50                  55                  60

His Pro Glu Thr Glu Glu Leu Met Ala Lys Tyr Arg Arg Ile Thr
65                  70                  75                  80

<210> SEQ ID NO 25
<211> LENGTH: 180
<212> TYPE: PRT
<213> ORGANISM: Azotobacter vinelandii

<400> SEQUENCE: 25

Met Ala Lys Ile Gly Leu Phe Phe Gly Ser Asn Thr Gly Lys Thr Arg
1               5                   10                  15

Lys Val Ala Lys Ser Ile Lys Lys Arg Phe Asp Asp Glu Thr Met Ser
                20                  25                  30

Asp Ala Leu Asn Val Asn Arg Val Ser Ala Glu Asp Phe Ala Gln Tyr
            35                  40                  45

Gln Phe Leu Ile Leu Gly Thr Pro Thr Leu Gly Glu Gly Glu Leu Pro

```
            50                  55                  60
Gly Leu Ser Ser Asp Cys Glu Asn Glu Ser Trp Glu Phe Leu Pro
65                  70                  75                  80

Lys Ile Glu Gly Leu Asp Phe Ser Gly Lys Thr Val Ala Leu Phe Gly
                85                  90                  95

Leu Gly Asp Gln Val Gly Tyr Pro Glu Asn Tyr Leu Asp Ala Leu Gly
                100                 105                 110

Glu Leu Tyr Ser Phe Phe Lys Asp Arg Gly Ala Lys Ile Val Gly Ser
                115                 120                 125

Trp Ser Thr Asp Gly Tyr Glu Phe Glu Ser Ser Glu Ala Val Val Asp
            130                 135                 140

Gly Lys Phe Val Gly Leu Ala Leu Asp Leu Asp Asn Gln Ser Gly Lys
145                 150                 155                 160

Thr Asp Glu Arg Val Ala Ala Trp Leu Ala Gln Ile Ala Pro Glu Phe
                165                 170                 175

Gly Leu Ser Leu
            180

<210> SEQ ID NO 26
<211> LENGTH: 180
<212> TYPE: PRT
<213> ORGANISM: Azotobacter chroococcum

<400> SEQUENCE: 26

Met Ala Lys Ile Gly Leu Phe Phe Gly Ser Asn Thr Gly Lys Thr Arg
1               5                   10                  15

Lys Val Ala Lys Ser Ile Lys Lys Arg Phe Asp Asp Glu Thr Met Ser
                20                  25                  30

Asp Ala Val Asn Val Asn Arg Val Ser Ala Glu Asp Phe Ala Gln Tyr
            35                  40                  45

Gln Phe Leu Ile Leu Gly Thr Pro Thr Leu Gly Glu Gly Glu Leu Pro
        50                  55                  60

Gly Leu Ser Ser Asp Cys Glu Asn Glu Ser Trp Glu Phe Leu Pro
65                  70                  75                  80

Lys Ile Glu Gly Leu Asp Phe Ser Gly Lys Thr Val Ala Leu Phe Gly
                85                  90                  95

Leu Gly Asp Gln Val Gly Tyr Pro Glu Asn Phe Leu Asp Ala Met Gly
                100                 105                 110

Glu Leu His Ser Phe Phe Thr Glu Arg Gly Ala Lys Val Val Gly Ala
                115                 120                 125

Trp Ser Thr Asp Gly Tyr Glu Phe Gly Ser Thr Ala Val Val Asp
            130                 135                 140

Gly Lys Phe Val Gly Leu Ala Leu Asp Leu Asp Asn Gln Ser Gly Lys
145                 150                 155                 160

Thr Asp Glu Arg Val Ala Ala Trp Leu Ala Gln Ile Ala Pro Glu Phe
                165                 170                 175

Gly Leu Ser Leu
            180

<210> SEQ ID NO 27
<211> LENGTH: 176
<212> TYPE: PRT
<213> ORGANISM: E. coli

<400> SEQUENCE: 27

Met Ala Ile Thr Gly Ile Phe Phe Gly Ser Asp Thr Gly Asn Thr Glu
```

-continued

```
             1               5                  10                 15
           Asn Ile Ala Lys Met Ile Gln Lys Gln Leu Gly Lys Asp Val Ala Asp
                           20                  25                 30

Val His Asp Ile Ala Lys Ser Ser Lys Glu Asp Leu Glu Ala Tyr Asp
                           35                  40                 45

Ile Leu Leu Leu Gly Ile Pro Thr Trp Tyr Tyr Gly Glu Ala Gln Cys
                           50                  55                 60

Asp Trp Asp Asp Phe Phe Pro Thr Leu Glu Glu Ile Asp Phe Asn Gly
           65                          70                  75                 80

Lys Leu Val Ala Leu Phe Gly Cys Gly Asp Gln Glu Asp Tyr Ala Glu
                               85                  90                 95

Tyr Phe Cys Asp Ala Leu Gly Thr Ile Arg Asp Ile Ile Glu Pro Arg
                              100                 105                110

Gly Ala Thr Ile Val Gly His Trp Pro Thr Ala Gly Tyr His Phe Glu
                              115                 120                125

Ala Ser Lys Gly Leu Ala Asp Asp His Phe Val Gly Leu Ala Ile
                              130                 135                140

Asp Glu Asp Arg Gln Pro Glu Leu Thr Ala Glu Arg Val Glu Lys Trp
           145                         150                 155                160

Val Lys Gln Ile Ser Glu Glu Leu His Leu Asp Glu Ile Leu Asn Ala
                              165                 170                175

<210> SEQ ID NO 28
<211> LENGTH: 158
<212> TYPE: PRT
<213> ORGANISM: B. subtilis

<400> SEQUENCE: 28

Met Ala Lys Ala Leu Ile Thr Tyr Ala Ser Met Ser Gly Asn Thr Glu
           1               5                  10                 15

Asp Ile Ala Phe Ile Ile Lys Asp Thr Leu Gln Glu Tyr Glu Leu Asp
                           20                  25                 30

Ile Asp Cys Val Glu Ile Asn Asp Met Asp Ala Ser Cys Leu Thr Ser
                           35                  40                 45

Tyr Asp Tyr Val Leu Ile Gly Thr Tyr Thr Trp Gly Asp Gly Asp Leu
                           50                  55                 60

Pro Tyr Glu Ala Glu Asp Phe Phe Glu Val Lys Gln Ile Gln Leu
           65                          70                  75                 80

Asn Gly Leu Lys Thr Ala Cys Phe Gly Ser Gly Asp Tyr Ser Tyr Pro
                               85                  90                 95

Lys Phe Cys Glu Ala Val Asn Leu Phe Asn Val Met Leu Gln Glu Ala
                              100                 105                110

Gly Ala Ala Val Tyr Gln Glu Thr Leu Lys Ile Glu Leu Ala Pro Glu
                              115                 120                125

Thr Asp Glu Asp Val Glu Ser Cys Arg Ala Phe Ala Arg Gly Phe Leu
           130                         135                 140

Ala Trp Ala Asp Tyr Met Asn Lys Glu Lys Ile His Val Ser
           145                         150                 155

<210> SEQ ID NO 29
<211> LENGTH: 1199
<212> TYPE: PRT
<213> ORGANISM: Synechocystis sp.

<400> SEQUENCE: 29

Met Ser Leu Pro Thr Tyr Ala Thr Leu Asp Gly Asn Glu Ala Val Ala
```

-continued

```
1               5                   10                  15
Arg Val Ala Tyr Leu Leu Ser Glu Val Ile Ala Ile Tyr Pro Ile Thr
                20                  25                  30
Pro Ser Ser Pro Met Gly Glu Trp Ser Asp Ala Trp Ala Ala Glu His
                35                  40                  45
Arg Pro Asn Leu Trp Gly Thr Val Pro Leu Val Val Glu Met Gln Ser
 50                 55                  60
Glu Gly Gly Ala Ala Gly Thr Val His Gly Ala Leu Gln Ser Gly Ala
 65                 70                  75                  80
Leu Thr Thr Thr Phe Thr Ala Ser Gln Gly Leu Met Leu Met Leu Pro
                85                  90                  95
Asn Met His Lys Ile Ala Gly Glu Leu Thr Ala Met Val Leu His Val
                100                 105                 110
Ala Ala Arg Ser Leu Ala Ala Gln Gly Leu Ser Ile Phe Gly Asp His
                115                 120                 125
Ser Asp Val Met Ala Ala Arg Asn Thr Gly Phe Ala Met Leu Ser Ser
 130                135                 140
Asn Ser Val Gln Glu Ala His Asp Phe Ala Leu Ile Ala Thr Ala Thr
 145                150                 155                 160
Ser Phe Ala Thr Arg Ile Pro Gly Leu His Phe Asp Gly Phe Arg
                165                 170                 175
Thr Ser His Glu Glu Gln Lys Ile Glu Leu Leu Pro Gln Glu Val Leu
                180                 185                 190
Arg Gly Leu Ile Lys Asp Glu Asp Val Leu Ala His Arg Gly Arg Ala
                195                 200                 205
Leu Thr Pro Asp Arg Pro Lys Leu Arg Gly Thr Ala Gln Asn Pro Asp
 210                215                 220
Val Tyr Phe Gln Ala Arg Glu Thr Val Asn Pro Phe Tyr Ala Ser Tyr
 225                230                 235                 240
Pro Asn Val Leu Glu Gln Val Met Glu Gln Phe Gly Gln Leu Thr Gly
                245                 250                 255
Arg His Tyr Arg Pro Tyr Glu Tyr Cys Gly His Pro Glu Ala Glu Arg
                260                 265                 270
Val Ile Val Leu Met Gly Ser Gly Ala Glu Thr Ala Gln Glu Thr Val
                275                 280                 285
Asp Phe Leu Thr Ala Gln Gly Glu Lys Val Gly Leu Leu Lys Val Arg
                290                 295                 300
Leu Tyr Arg Pro Phe Ala Gly Asp Arg Leu Val Asn Ala Leu Pro Lys
 305                310                 315                 320
Thr Val Gln Lys Ile Ala Val Leu Asp Arg Cys Lys Glu Pro Gly Ser
                325                 330                 335
Ile Gly Glu Pro Leu Tyr Gln Asp Val Leu Thr Ala Phe Phe Glu Ala
                340                 345                 350
Gly Met Met Pro Lys Ile Gly Gly Arg Tyr Gly Leu Ser Ser Lys
                355                 360                 365
Glu Phe Thr Pro Ala Met Val Lys Gly Val Leu Asp His Leu Asn Gln
                370                 375                 380
Thr Asn Pro Lys Asn His Phe Thr Val Gly Ile Asn Asp Asp Leu Ser
 385                390                 395                 400
His Thr Ser Ile Asp Tyr Asp Pro Ser Phe Ser Thr Glu Ala Asp Ser
                405                 410                 415
Val Val Arg Ala Ile Phe Tyr Gly Leu Gly Ser Asp Gly Thr Val Gly
                420                 425                 430
```

```
Ala Asn Lys Asn Ser Ile Lys Ile Ile Gly Glu Asp Thr Asp Asn Tyr
        435                 440                 445

Ala Gln Gly Tyr Phe Val Tyr Asp Ser Lys Lys Ser Gly Ser Val Thr
        450                 455                 460

Val Ser His Leu Arg Phe Gly Pro Asn Pro Ile Leu Ser Thr Tyr Leu
465                 470                 475                 480

Ile Ser Gln Ala Asn Phe Val Ala Cys His Gln Trp Glu Phe Leu Glu
                485                 490                 495

Gln Phe Glu Val Leu Glu Pro Ala Val Asp Gly Val Phe Leu Val
                500                 505                 510

Asn Ser Pro Tyr Gly Pro Glu Glu Ile Trp Arg Glu Phe Pro Arg Lys
        515                 520                 525

Val Gln Gln Glu Ile Ile Asp Lys Asn Leu Lys Val Tyr Thr Ile Asn
        530                 535                 540

Ala Asn Asp Val Ala Arg Asp Ala Gly Met Gly Arg Arg Thr Asn Thr
545                 550                 555                 560

Val Met Gln Thr Cys Phe Phe Ala Leu Ala Gly Val Leu Pro Arg Glu
                565                 570                 575

Glu Ala Ile Ala Lys Ile Lys Gln Ser Val Gln Lys Thr Tyr Gly Lys
                580                 585                 590

Lys Gly Gln Glu Ile Val Glu Met Asn Ile Lys Ala Val Asp Ser Thr
        595                 600                 605

Leu Ala His Leu Tyr Glu Val Ser Val Pro Glu Thr Val Ser Asp Asp
        610                 615                 620

Ala Pro Ala Met Arg Pro Val Val Pro Asp Asn Ala Pro Val Phe Val
625                 630                 635                 640

Arg Glu Val Leu Gly Lys Ile Met Ala Arg Gln Gly Asp Asp Leu Pro
                645                 650                 655

Val Ser Ala Leu Pro Cys Asp Gly Thr Tyr Pro Thr Ala Thr Thr Gln
                660                 665                 670

Trp Glu Lys Arg Asn Val Gly His Glu Ile Pro Val Trp Asp Pro Asp
        675                 680                 685

Val Cys Val Gln Cys Gly Lys Cys Val Ile Val Cys Pro His Ala Val
        690                 695                 700

Ile Arg Gly Lys Val Tyr Glu Glu Ala Glu Leu Ala Asn Ala Pro Val
705                 710                 715                 720

Ser Phe Lys Phe Thr Asn Ala Lys Asp His Asp Trp Gln Gly Ser Lys
                725                 730                 735

Phe Thr Ile Gln Val Ala Pro Glu Asp Cys Thr Gly Cys Gly Ile Cys
                740                 745                 750

Val Asp Val Cys Pro Ala Lys Asn Lys Ser Gln Pro Arg Leu Arg Ala
        755                 760                 765

Ile Asn Met Ala Pro Gln Leu Pro Leu Arg Glu Gln Glu Arg Glu Asn
        770                 775                 780

Trp Asp Phe Phe Leu Asp Leu Pro Asn Pro Asp Arg Leu Ser Leu Asn
785                 790                 795                 800

Leu Asn Lys Ile Ser His Gln Gln Met Gln Glu Pro Leu Phe Glu Phe
                805                 810                 815

Ser Gly Ala Cys Ala Gly Cys Gly Glu Thr Pro Tyr Leu Lys Leu Val
                820                 825                 830

Ser Gln Leu Phe Gly Asp Arg Met Leu Val Ala Asn Ala Thr Gly Cys
        835                 840                 845
```

-continued

Ser Ser Ile Tyr Gly Gly Asn Leu Pro Thr Thr Pro Trp Ala Gln Asn
850                 855                 860

Ala Glu Gly Arg Gly Pro Ala Trp Ser Asn Ser Leu Phe Glu Asp Asn
865                 870                 875                 880

Ala Glu Phe Gly Leu Gly Phe Arg Val Ala Ile Asp Lys Gln Thr Glu
            885                 890                 895

Phe Ala Gly Glu Leu Leu Lys Thr Phe Ala Gly Glu Leu Gly Asp Ser
            900                 905                 910

Leu Val Ser Glu Ile Leu Asn Asn Ala Gln Thr Thr Glu Ala Asp Ile
915                 920                 925

Phe Glu Gln Arg Gln Leu Val Glu Gln Val Lys Gln Arg Leu Gln Asn
930                 935                 940

Leu Glu Thr Pro Gln Ala Gln Met Phe Leu Ser Val Ala Asp Tyr Leu
945                 950                 955                 960

Val Lys Lys Ser Val Trp Ile Ile Gly Gly Asp Gly Trp Ala Tyr Asp
            965                 970                 975

Ile Gly Tyr Gly Gly Leu Asp His Val Leu Ala Ser Gly Arg Asn Val
            980                 985                 990

Asn Ile Leu Val Met Asp Thr Glu Val Tyr Ser Asn Thr Gly Gly Gln
            995                 1000                1005

Ala Ser Lys Ala Thr Pro Arg Ala Ala Val Ala Lys Phe Ala Ala
    1010                1015                1020

Gly Gly Lys Pro Ser Pro Lys Lys Asp Leu Gly Leu Met Ala Met
    1025                1030                1035

Thr Tyr Gly Asn Val Tyr Val Ala Ser Ile Ala Met Gly Ala Lys
    1040                1045                1050

Asn Glu Gln Ser Ile Lys Ala Phe Met Glu Ala Glu Ala Tyr Pro
    1055                1060                1065

Gly Val Ser Leu Ile Ile Ala Tyr Ser His Cys Ile Ala His Gly
    1070                1075                1080

Ile Asn Met Thr Thr Ala Met Asn His Gln Lys Glu Leu Val Asp
    1085                1090                1095

Ser Gly Arg Trp Leu Leu Tyr Arg Tyr Asn Pro Leu Leu Ala Asp
    1100                1105                1110

Glu Gly Lys Asn Pro Leu Gln Leu Asp Met Gly Ser Pro Lys Val
    1115                1120                1125

Ala Ile Asp Lys Thr Val Tyr Ser Glu Asn Arg Phe Ala Met Leu
    1130                1135                1140

Thr Arg Ser Gln Pro Glu Ala Lys Arg Leu Met Lys Leu Ala
    1145                1150                1155

Gln Gly Asp Val Asn Thr Arg Trp Ala Met Tyr Glu Tyr Leu Ala
    1160                1165                1170

Lys Arg Ser Leu Gly Gly Glu Ile Asn Gly Asn Asn His Gly Val
    1175                1180                1185

Ser Pro Ser Pro Glu Val Ile Ala Lys Ser Val
    1190                1195

<210> SEQ ID NO 30
<211> LENGTH: 1170
<212> TYPE: PRT
<213> ORGANISM: Kluyvera intermedia

<400> SEQUENCE: 30

Met Ser Gly Lys Met Lys Thr Met Asp Gly Asn Ala Ala Ala Ala Trp
1               5                   10                  15

```
Ile Ser Tyr Ala Phe Thr Asp Val Ala Ala Ile Tyr Pro Ile Thr Pro
             20                  25                  30

Ser Thr Pro Met Ala Glu Asn Val Asp Glu Trp Thr Ala Gln Gly Lys
         35                  40                  45

Lys Asn Leu Phe Gly Gln Pro Val Arg Leu Met Glu Met Gln Ser Glu
 50                  55                  60

Ala Gly Ala Ala Gly Ala Val His Gly Ala Leu Gln Ala Gly Ala Leu
 65                  70                  75                  80

Thr Thr Thr Tyr Thr Ala Ser Gln Gly Leu Leu Leu Met Ile Pro Asn
                 85                  90                  95

Leu Tyr Lys Ile Ala Gly Glu Leu Leu Pro Gly Val Phe His Val Ser
                100                 105                 110

Ala Arg Ala Leu Ala Thr Asn Ser Leu Asn Ile Phe Gly Asp His Gln
             115                 120                 125

Asp Val Met Ala Val Arg Gln Thr Gly Cys Ala Met Leu Ala Glu Asn
130                 135                 140

Asn Val Gln Gln Val Met Asp Leu Ser Ala Val Ala His Leu Ser Ala
145                 150                 155                 160

Ile Lys Gly Arg Val Pro Phe Ile Asn Phe Phe Asp Gly Phe Arg Thr
                165                 170                 175

Ser His Glu Ile Gln Lys Ile Glu Val Leu Glu His Glu Ala Leu Ala
            180                 185                 190

Pro Leu Leu Asp Gln Glu Ala Leu Asn Leu Phe Arg Arg Asn Ala Leu
            195                 200                 205

Asn Pro Asp His Pro Val Ile Arg Gly Thr Ala Gln Asn Pro Asp Ile
            210                 215                 220

Tyr Phe Gln Glu Arg Glu Ala Ser Asn Arg Phe Tyr Gln Ala Leu Pro
225                 230                 235                 240

Asp Ile Val Glu Gly Tyr Met Ala Glu Ile Tyr Arg Ile Thr Gly Arg
                245                 250                 255

Glu Tyr His Leu Phe Asp Tyr Tyr Gly Ser Pro Asp Ala Glu Gln Ile
            260                 265                 270

Ile Ile Ala Met Gly Ser Val Cys Asp Thr Ile Gln Glu Val Val Asp
            275                 280                 285

Ala Met Ile Asp Ser Gly Glu Lys Val Gly Leu Val Ser Val His Leu
290                 295                 300

Phe Arg Pro Phe Ser Leu Ala His Phe Met Ala Lys Ile Pro Ala Ser
305                 310                 315                 320

Val Lys Arg Ile Ala Val Leu Asp Arg Thr Lys Glu Pro Gly Ala Gln
                325                 330                 335

Ala Glu Pro Leu Cys Leu Asp Val Lys Asn Ala Phe Tyr His His Asp
            340                 345                 350

Asn Pro Pro Leu Ile Val Gly Gly Arg Tyr Ala Leu Gly Gly Lys Asp
            355                 360                 365

Val Leu Pro Gly His Ile Val Ser Val Phe Glu Asn Leu Lys Lys Pro
            370                 375                 380

Leu Pro Met Asp Gly Phe Thr Val Gly Ile Phe Asp Asp Val Thr His
385                 390                 395                 400

Thr Ser Leu Pro Val Pro Ala Tyr Asp Ile His Val Ser Arg Glu Gly
                405                 410                 415

Ile Thr Ala Cys Lys Phe Trp Gly Leu Gly Ser Asp Gly Thr Val Ser
            420                 425                 430
```

```
Ala Asn Lys Asn Ala Ile Lys Ile Ile Gly Asp Asn Thr Ser Met Phe
            435                 440                 445

Ala Gln Ala Tyr Phe Ala Tyr Asp Ser Lys Lys Ser Gly Gly Ile Thr
450                 455                 460

Met Ser His Leu Arg Phe Gly Lys Arg Pro Ile Thr Ser Pro Tyr Leu
465                 470                 475                 480

Ile His Asn Ala Asp Phe Ile Ala Cys Ser Gln Gln Ser Tyr Val Asp
                485                 490                 495

Lys Tyr Asp Leu Leu Asp Gly Ile Asn Pro Gly Gly Ile Phe Leu Leu
            500                 505                 510

Asn Cys Thr Trp Phe Gly Glu Glu Val Glu Arg His Leu Pro Asn Lys
            515                 520                 525

Met Lys Arg Ile Ile Ala Arg Gln Gly Val Arg Phe Tyr Thr Leu Asn
            530                 535                 540

Ala Val Asp Ile Ala Arg Lys Leu Gly Leu Gly Arg Phe Asn Met
545                 550                 555                 560

Leu Met Gln Ala Ala Phe Phe Lys Leu Thr Asp Ile Ile Asp Ala Lys
                565                 570                 575

Thr Ala Ser Glu His Leu Lys Lys Ala Val Ala Lys Ser Tyr Gly Ser
            580                 585                 590

Lys Gly Gln Asn Val Val Asp Met Asn Asn Ala Ala Ile Asp Leu Gly
            595                 600                 605

Met Asp Ala Leu Gln Glu Ile Ile Val Pro Asp His Trp Ala Tyr Val
            610                 615                 620

Glu Glu Glu Ala Asn Asn Asp Gly Lys Leu Met Pro Asp Phe Ile Arg
625                 630                 635                 640

Asn Ile Leu Glu Pro Met Asn Arg Gln Asn Gly Asp Lys Leu Pro Val
                645                 650                 655

Ser Ala Phe Leu Gly Met Glu Asp Gly Thr Phe Pro Pro Gly Thr Ala
            660                 665                 670

Ala Trp Glu Lys Arg Gly Ile Ala Met Gln Val Pro Val Trp Gln Pro
            675                 680                 685

Glu Gly Cys Thr Gln Cys Asn Gln Cys Ala Phe Ile Cys Pro His Ala
690                 695                 700

Ala Ile Arg Pro Ala Leu Leu Ser Ser Glu Glu Arg Glu Ala Ala Pro
705                 710                 715                 720

Val Ala Leu Leu Ser Lys Val Ala Gln Gly Ala Lys His Tyr Glu Tyr
                725                 730                 735

His Leu Ala Val Ser Pro Leu Asp Cys Ser Gly Cys Gly Asn Cys Val
            740                 745                 750

Asp Ile Cys Pro Ser Lys Gly Lys Ala Leu Ala Met Lys Pro Leu Asp
            755                 760                 765

Ser Gln Arg His Met Val Pro Val Trp Asp His Ala Leu Ala Leu Ala
            770                 775                 780

Pro Lys Glu Asn Pro Phe Ser Lys Ala Thr Val Lys Gly Cys Gln Phe
785                 790                 795                 800

Glu Pro Pro Leu Leu Glu Phe Ser Gly Ala Cys Ala Gly Cys Gly Glu
                805                 810                 815

Thr Pro Tyr Ala Arg Leu Ile Thr Gln Leu Phe Gly Asp Arg Met Met
            820                 825                 830

Ile Ala Asn Ala Thr Gly Cys Ser Ser Ile Trp Gly Ala Ser Ala Pro
            835                 840                 845

Ser Ile Pro Trp Thr Thr Asn His Lys Gly Gln Gly Pro Ala Trp Ala
```

```
                        850                 855                 860
Asn Ser Leu Phe Glu Asp Asn Ala Glu Phe Gly Leu Gly Met Met Leu
865                 870                 875                 880

Gly Gly Arg Ala Ile Arg Glu Gln Leu Ala Ser Asp Ala Ala Ser Val
                        885                 890                 895

Leu Glu Arg Pro Leu His Pro Asp Leu Gln Gln Ala Leu Arg Asp Trp
                900                 905                 910

Leu Glu His Lys Asp Leu Gly Glu Gly Thr Arg Ala Arg Ala Glu Lys
            915                 920                 925

Leu Ser Ala Leu Leu Ala Ala Glu Lys Gly Asp Asp Leu Leu Asn
        930                 935                 940

Arg Leu Tyr Gln Asn Gln Asp Tyr Phe Thr Lys Arg Ser Gln Trp Ile
945                 950                 955                 960

Phe Gly Asp Gly Trp Ala Tyr Asp Ile Gly Phe Gly Gly Leu Asp
                965                 970                 975

His Val Leu Ala Ser Gly Glu Asp Val Asn Ile Leu Val Phe Asp Thr
                980                 985                 990

Glu Val Tyr Ser Asn Thr Gly Gly  Gln Ser Ser Lys Ser  Thr Pro Val
            995                 1000                1005

Ala Ala  Ile Ala Lys Phe Ala  Ala Glu Gly Lys Arg  Thr Arg Lys
        1010                1015                1020

Lys Asp  Leu Gly Met Met Ala  Val Ser Tyr Gly Asn  Val Tyr Val
        1025                1030                1035

Ala Gln  Val Ala Met Gly Ala  Asp Lys Ala Gln Thr  Leu Arg Ala
        1040                1045                1050

Ile Ala  Glu Ala Glu Ala Trp  Pro Gly Pro Ser Leu  Val Ile Ala
        1055                1060                1065

Tyr Ala  Ala Cys Ile Asn His  Gly Leu Lys Ala Gly  Met Gly Arg
        1070                1075                1080

Ser Ile  Ser Glu Ala Lys Arg  Ala Val Glu Ala Gly  Tyr Trp His
        1085                1090                1095

Leu Trp  Arg Tyr Asn Pro Gln  Leu Leu Ala Lys Gly  Lys Asn Pro
        1100                1105                1110

Phe Ile  Leu Asp Ser Glu Glu  Pro Glu Ser Phe  Arg Asp Phe
        1115                1120                1125

Leu Met  Gly Glu Val Arg Tyr  Ala Ser Leu Gly Arg  Thr Ser Pro
        1130                1135                1140

Glu Val  Ala Asp Ser Leu Phe  Ala Gln Thr Glu Gln  Asp Ala Lys
        1145                1150                1155

Asp Arg  Tyr Ala Gln Tyr Arg  Arg Leu Ala Gly Glu
        1160                1165                1170

<210> SEQ ID NO 31
<211> LENGTH: 1232
<212> TYPE: PRT
<213> ORGANISM: Desulfovibrio africanus

<400> SEQUENCE: 31

Met Gly Lys Lys Met Met Thr Thr Asp Gly Asn Thr Ala Thr Ala His
1               5                   10                  15

Val Ala Tyr Ala Met Ser Glu Val Ala Ala Ile Tyr Pro Ile Thr Pro
                20                  25                  30

Ser Ser Thr Met Gly Glu Glu Ala Asp Asp Trp Ala Ala Gln Gly Arg
            35                  40                  45
```

```
Lys Asn Ile Phe Gly Gln Thr Leu Thr Ile Arg Glu Met Gln Ser Glu
 50                  55                  60
Ala Gly Ala Ala Gly Ala Val His Gly Ala Leu Ala Gly Ala Leu
 65                  70                  75                  80
Thr Thr Thr Phe Thr Ala Ser Gln Gly Leu Leu Leu Met Ile Pro Asn
                     85                  90                  95
Met Tyr Lys Ile Ser Gly Glu Leu Leu Pro Gly Val Phe His Val Thr
                100                 105                 110
Ala Arg Ala Ile Ala Ala His Ala Leu Ser Ile Phe Gly Asp His Gln
                115                 120                 125
Asp Ile Tyr Ala Ala Arg Gln Thr Gly Phe Ala Met Leu Ala Ser Ser
130                 135                 140
Ser Val Gln Glu Ala His Asp Met Ala Leu Val Ala His Leu Ala Ala
145                 150                 155                 160
Ile Glu Ser Asn Val Pro Phe Met His Phe Asp Gly Phe Arg Thr
                    165                 170                 175
Ser His Glu Ile Gln Lys Ile Glu Val Leu Asp Tyr Ala Asp Met Ala
                180                 185                 190
Ser Leu Val Asn Gln Lys Ala Leu Ala Glu Phe Arg Ala Lys Ser Met
                195                 200                 205
Asn Pro Glu His Pro His Val Arg Gly Thr Ala Gln Asn Pro Asp Ile
210                 215                 220
Tyr Phe Gln Gly Arg Glu Ala Ala Asn Pro Tyr Leu Lys Val Pro
225                 230                 235                 240
Gly Ile Val Ala Glu Tyr Met Gln Lys Val Ala Ala Leu Thr Gly Arg
                245                 250                 255
Ser Tyr Lys Leu Phe Asp Tyr Val Gly Ala Pro Asp Ala Glu Arg Val
                260                 265                 270
Ile Val Ser Met Gly Ser Ser Cys Glu Thr Ile Glu Glu Val Ile Asn
                275                 280                 285
His Leu Ala Ala Lys Gly Asp Lys Ile Gly Leu Ile Lys Val Arg Leu
                290                 295                 300
Tyr Arg Pro Phe Val Ser Glu Ala Phe Phe Ala Ala Leu Pro Ala Ser
305                 310                 315                 320
Ala Lys Val Ile Thr Val Leu Asp Arg Thr Lys Glu Pro Gly Ala Pro
                325                 330                 335
Gly Asp Pro Leu Tyr Leu Asp Val Cys Ser Ala Phe Val Glu Arg Gly
                340                 345                 350
Glu Ala Met Pro Lys Ile Leu Ala Gly Arg Tyr Gly Leu Gly Ser Lys
                355                 360                 365
Glu Phe Ser Pro Ala Met Val Lys Ser Val Tyr Asp Asn Met Ser Gly
370                 375                 380
Ala Lys Lys Asn His Phe Thr Val Gly Ile Glu Asp Val Thr Gly
385                 390                 395                 400
Thr Ser Leu Pro Val Asp Asn Ala Phe Ala Asp Thr Thr Pro Lys Gly
                405                 410                 415
Thr Ile Gln Cys Gln Phe Trp Gly Leu Gly Ala Asp Gly Thr Val Gly
                420                 425                 430
Ala Asn Lys Gln Ala Ile Lys Ile Gly Asp Asn Thr Asp Leu Phe
                435                 440                 445
Ala Gln Gly Tyr Phe Ser Tyr Asp Ser Lys Lys Ser Gly Gly Ile Thr
450                 455                 460
Ile Ser His Leu Arg Phe Gly Glu Lys Pro Ile Gln Ser Thr Tyr Leu
```

```
            465                 470                 475                 480
        Val Asn Arg Ala Asp Tyr Val Ala Cys His Asn Pro Ala Tyr Val Gly
                        485                 490                 495

Ile Tyr Asp Ile Leu Glu Gly Ile Lys Asp Gly Gly Thr Phe Val Leu
                        500                 505                 510

Asn Ser Pro Trp Ser Ser Leu Glu Asp Met Asp Lys His Leu Pro Ser
                        515                 520                 525

Gly Ile Lys Arg Thr Ile Ala Asn Lys Lys Leu Lys Phe Tyr Asn Ile
                        530                 535                 540

Asp Ala Val Lys Ile Ala Thr Asp Val Gly Leu Gly Gly Arg Ile Asn
        545                 550                 555                 560

Met Ile Met Gln Thr Ala Phe Phe Lys Leu Ala Gly Val Leu Pro Phe
                            565                 570                 575

Glu Lys Ala Val Asp Leu Leu Lys Lys Ser Ile His Lys Ala Tyr Gly
                        580                 585                 590

Lys Lys Gly Glu Lys Ile Val Lys Met Asn Thr Asp Ala Val Asp Gln
                        595                 600                 605

Ala Val Thr Ser Leu Gln Glu Phe Lys Tyr Pro Ala Ser Trp Lys Asp
                        610                 615                 620

Ala Pro Ala Glu Thr Lys Ala Glu Pro Lys Thr Asn Glu Phe Phe Lys
        625                 630                 635                 640

Asn Val Val Lys Pro Ile Leu Thr Gln Gln Gly Asp Lys Leu Pro Val
                        645                 650                 655

Ser Ala Phe Glu Ala Asp Gly Arg Phe Pro Leu Gly Thr Ser Gln Phe
                        660                 665                 670

Glu Lys Arg Gly Val Ala Ile Asn Val Pro Gln Trp Val Pro Glu Asn
                        675                 680                 685

Cys Ile Gln Cys Asn Gln Cys Ala Phe Val Cys Pro His Ser Ala Ile
                        690                 695                 700

Leu Pro Val Leu Ala Lys Glu Glu Leu Val Gly Ala Pro Ala Asn
        705                 710                 715                 720

Phe Thr Ala Leu Glu Ala Lys Gly Lys Glu Leu Lys Gly Tyr Lys Phe
                            725                 730                 735

Arg Ile Gln Ile Asn Thr Leu Asp Cys Met Gly Cys Gly Asn Cys Ala
                            740                 745                 750

Asp Ile Cys Pro Pro Lys Glu Lys Ala Leu Val Met Gln Pro Leu Asp
                        755                 760                 765

Thr Gln Arg Asp Ala Gln Val Pro Asn Leu Glu Tyr Ala Ala Arg Ile
                        770                 775                 780

Pro Val Lys Ser Glu Val Leu Pro Arg Asp Ser Leu Lys Gly Ser Gln
        785                 790                 795                 800

Phe Gln Glu Pro Leu Met Glu Phe Ser Gly Ala Cys Ser Gly Cys Gly
                            805                 810                 815

Glu Thr Pro Tyr Val Arg Val Ile Thr Gln Leu Phe Gly Glu Arg Met
                        820                 825                 830

Phe Ile Ala Asn Ala Thr Gly Cys Ser Ser Ile Trp Gly Ala Ser Ala
                        835                 840                 845

Pro Ser Met Pro Tyr Lys Thr Asn Ser Leu Gly Gln Gly Pro Ala Trp
                        850                 855                 860

Gly Asn Ser Leu Phe Glu Asp Ala Ala Glu Tyr Gly Phe Gly Met Asn
        865                 870                 875                 880

Met Ser Met Phe Ala Arg Arg Thr His Leu Ala Asp Leu Ala Ala Lys
                        885                 890                 895
```

```
Ala Leu Glu Ser Asp Ala Ser Gly Asp Val Lys Glu Ala Leu Gln Gly
            900                 905                 910

Trp Leu Ala Gly Lys Asn Asp Pro Ile Lys Ser Lys Glu Tyr Gly Asp
        915                 920                 925

Lys Leu Lys Lys Leu Leu Ala Gly Gln Lys Asp Gly Leu Leu Gly Gln
    930                 935                 940

Ile Ala Ala Met Ser Asp Leu Tyr Thr Lys Lys Ser Val Trp Ile Phe
945                 950                 955                 960

Gly Gly Asp Gly Trp Ala Tyr Asp Ile Gly Tyr Gly Gly Leu Asp His
                965                 970                 975

Val Leu Ala Ser Gly Glu Asp Val Asn Val Phe Val Met Asp Thr Glu
            980                 985                 990

Val Tyr Ser Asn Thr Gly Gly Gln Ser Ser Lys Ala Thr Pro Thr Gly
        995                1000                1005

Ala Val Ala Lys Phe Ala Ala Gly Lys Arg Thr Gly Lys Lys
   1010                1015                1020

Asp Leu Ala Arg Met Val Met Thr Tyr Gly Tyr Val Tyr Val Ala
   1025                1030                1035

Thr Val Ser Met Gly Tyr Ser Lys Gln Gln Phe Leu Lys Val Leu
   1040                1045                1050

Lys Glu Ala Glu Ser Phe Pro Gly Pro Ser Leu Val Ile Ala Tyr
   1055                1060                1065

Ala Thr Cys Ile Asn Gln Gly Leu Arg Lys Gly Met Gly Lys Ser
   1070                1075                1080

Gln Asp Val Met Asn Thr Ala Val Lys Ser Gly Tyr Trp Pro Leu
   1085                1090                1095

Phe Arg Tyr Asp Pro Arg Leu Ala Ala Gln Gly Lys Asn Pro Phe
   1100                1105                1110

Gln Leu Asp Ser Lys Ala Pro Asp Gly Ser Val Glu Glu Phe Leu
   1115                1120                1125

Met Ala Gln Asn Arg Phe Ala Val Leu Asp Arg Ser Phe Pro Glu
   1130                1135                1140

Asp Ala Lys Arg Leu Arg Ala Gln Val Ala His Glu Leu Asp Val
   1145                1150                1155

Arg Phe Lys Glu Leu Glu Arg Met Ala Ala Thr Asn Ile Phe Glu
   1160                1165                1170

Ser Phe Ala Pro Ala Gly Gly Lys Ala Asp Gly Ser Val Asp Phe
   1175                1180                1185

Gly Glu Gly Ala Glu Phe Cys Thr Arg Asp Asp Thr Pro Met Met
   1190                1195                1200

Ala Arg Pro Asp Ser Gly Glu Ala Cys Asp Gln Asn Arg Ala Gly
   1205                1210                1215

Thr Ser Glu Gln Gln Gly Asp Leu Ser Lys Arg Thr Lys Lys
   1220                1225                1230

<210> SEQ ID NO 32
<211> LENGTH: 1199
<212> TYPE: PRT
<213> ORGANISM: Nostoc sp.

<400> SEQUENCE: 32

Met Ser Gln Thr Phe Ala Thr Ile Asp Gly Asn Glu Ala Val Ala Arg
1               5                   10                  15

Val Ala Tyr Lys Leu Asn Glu Val Ile Ala Ile Tyr Pro Ile Thr Pro
```

```
                20              25              30
Ser Ser Ala Met Gly Glu Trp Ala Asp Ala Trp Met Ala Glu Gly Arg
            35              40              45
Pro Asn Leu Trp Gly Thr Val Pro Ser Val Val Gln Met Gln Ser Glu
        50              55              60
Gly Gly Ala Ala Gly Ala Val His Gly Ala Leu Gln Thr Gly Ser Leu
65              70              75              80
Ser Thr Thr Phe Thr Ala Ser Gln Gly Leu Leu Met Ile Pro Asn
                85              90              95
Leu Tyr Lys Ile Gly Gly Glu Leu Thr Ser Met Val Val His Val Ala
                100             105             110
Ala Arg Ser Leu Ala Thr His Ala Leu Ser Ile Phe Gly Asp His Ser
            115             120             125
Asp Val Met Ala Ala Arg Gly Thr Gly Phe Ala Met Leu Cys Ser Ala
        130             135             140
Ser Val Gln Glu Ser His Asp Phe Ala Leu Ile Ala His Ala Ala Thr
145             150             155             160
Leu Asp Thr Arg Val Ser Phe Leu His Phe Phe Asp Gly Phe Arg Thr
                165             170             175
Ser His Glu Val Gln Lys Val Glu Leu Leu Ala Asp Asp Val Arg
                180             185             190
Ser Leu Ile Asn Glu Asp Lys Ile Phe Ala His Arg Ala Arg Ala Leu
                195             200             205
Thr Pro Asp Ser Pro Leu Leu Arg Gly Thr Ala Gln Asn Pro Asp Val
            210             215             220
Phe Phe Gln Ala Arg Glu Gly Ala Asn Pro Tyr Tyr Asn Ala Cys Pro
225             230             235             240
Ala Ile Val Gln Gly Ile Met Asp Lys Phe Gly Glu Arg Thr Gly Arg
                245             250             255
Tyr Tyr Gln Ile Tyr Glu Tyr His Gly Ala Ser Asp Ala Asp Arg Leu
                260             265             270
Ile Ile Ile Met Gly Ser Gly Cys Glu Thr Val His Glu Thr Val Asp
            275             280             285
Tyr Leu Asn Ala Arg Gly Glu Lys Val Gly Val Leu Lys Val Arg Leu
        290             295             300
Phe Arg Pro Trp Asp Val Glu Arg Phe Val Gln Ala Leu Pro His Ser
305             310             315             320
Val Gln Ala Ile Ala Val Leu Asp Arg Thr Lys Glu Pro Gly Ser Ala
                325             330             335
Gly Glu Pro Leu Tyr Gln Asp Val Val Thr Ala Ile His Glu Gly Trp
                340             345             350
Val Asn Lys Asn Asn Ser Pro Val Pro Ser Pro Gln Ser Pro Val Pro
            355             360             365
Lys Ile Ile Gly Gly Arg Tyr Gly Leu Ser Ser Lys Glu Phe Thr Pro
        370             375             380
Ala Met Val Lys Ala Val Phe Asp Asn Leu Ala Gln Ala Thr Pro Lys
385             390             395             400
Asn His Phe Thr Ile Gly Ile Asn Asp Asp Val Thr His Thr Ser Leu
                405             410             415
Glu Tyr Asp Pro Ser Phe Ser Thr Glu Pro Asp Asn Val Val Arg Ala
                420             425             430
Met Phe Tyr Gly Leu Gly Ser Asp Gly Thr Val Gly Ala Asn Lys Asn
            435             440             445
```

```
Ser Ile Lys Ile Ile Gly Glu Gly Thr Asp Asn Tyr Ala Gln Gly Tyr
    450                 455                 460

Phe Val Tyr Asp Ser Lys Lys Ser Gly Ser Met Thr Val Ser His Leu
465                 470                 475                 480

Arg Phe Gly Ser Gln Pro Ile Arg Ser Thr Tyr Leu Ile Asp Gln Ala
                485                 490                 495

Asn Phe Ile Gly Cys His His Trp Gly Phe Leu Glu Arg Ile Glu Val
                500                 505                 510

Leu Asn Ala Ala Ala His Gly Ala Thr Ile Leu Leu Asn Ser Pro Tyr
            515                 520                 525

Asn Ala Ala Thr Val Trp Glu Asn Leu Pro Leu Lys Val Arg Leu Gln
        530                 535                 540

Ile Leu Asp Lys Gln Leu Lys Leu Tyr Val Ile Asn Ala Asn Gln Val
545                 550                 555                 560

Ala Arg Asp Ser Gly Met Gly Gly Arg Ile Asn Thr Ile Met Gln Val
                565                 570                 575

Cys Phe Phe Ala Leu Ala Gly Val Leu Pro Glu Val Gln Ala Ile Ala
                580                 585                 590

Lys Ile Lys Gln Ala Ile Glu Lys Thr Tyr Gly Lys Lys Gly Val Glu
        595                 600                 605

Val Val Arg Met Asn Leu Gln Ala Val Asp Gln Thr Leu Glu Asn Leu
610                 615                 620

His Glu Val Lys Ile Pro Ile Glu Glu Lys Gly Lys Trp Ile Asp Glu
625                 630                 635                 640

Glu Ala Leu Leu Ser Asn Gln Ser Pro Phe Ser Thr Ser Ala Pro Lys
                645                 650                 655

Phe Val Arg Asp Val Leu Gly Lys Ile Met Val Trp Gln Gly Asp Asp
                660                 665                 670

Leu Pro Val Ser Thr Leu Pro Pro Asp Gly Thr Phe Pro Thr Gly Thr
            675                 680                 685

Ala Lys Trp Glu Lys Arg Asn Val Ala Gln Glu Ile Pro Val Trp Asp
        690                 695                 700

Thr Asp Ile Cys Val Gln Cys Ser Lys Cys Val Met Val Cys Pro His
705                 710                 715                 720

Ala Ala Ile Arg Ala Lys Val Tyr Gln Pro Ser Glu Leu Glu Asn Ala
                725                 730                 735

Pro Pro Thr Phe Lys Ser Val Asp Ala Lys Asp Arg Asp Phe Ala Asn
                740                 745                 750

Gln Lys Phe Thr Ile Gln Val Ala Pro Glu Asp Cys Thr Gly Cys Ala
            755                 760                 765

Ile Cys Val Asn Val Cys Pro Ala Lys Asn Lys Ser Glu Pro Ser Leu
        770                 775                 780

Lys Ala Ile Asn Met Ala Asn Gln Leu Pro Leu Arg Glu Gln Glu Arg
785                 790                 795                 800

Asp Asn Trp Asp Phe Phe Leu Asn Leu Pro Asn Pro Asp Arg Arg Asn
                805                 810                 815

Leu Lys Leu Asn Gln Ile Arg Gln Gln Leu Gln Glu Pro Leu Phe
            820                 825                 830

Glu Phe Ser Gly Ala Cys Ala Gly Cys Gly Glu Thr Pro Tyr Val Lys
        835                 840                 845

Leu Leu Thr Gln Leu Phe Gly Asp Arg Ser Val Ile Ala Asn Ala Thr
    850                 855                 860
```

```
Gly Cys Ser Ser Ile Tyr Gly Gly Asn Leu Pro Thr Thr Pro Trp Thr
865                 870                 875                 880

Lys Asn Asn Asp Gly Arg Gly Pro Ala Trp Ser Asn Ser Leu Phe Glu
            885                 890                 895

Asp Asn Ala Glu Phe Gly Phe Gly Tyr Arg Leu Ser Leu Asp Lys Gln
        900                 905                 910

Ala Glu Phe Ala Ala Glu Leu Leu Gln Gln Phe Ser Thr Glu Val Gly
    915                 920                 925

Asp Asn Leu Val Asp Ser Ile Leu Lys Ala Pro Gln Lys Thr Glu Ala
930                 935                 940

Asp Ile Trp Glu Gln Arg Gln Arg Ile Glu Leu Leu Lys Gln Gln Leu
945                 950                 955                 960

Asp Lys Ile Pro Thr Phe Asp Pro Asn Leu Lys Ser Lys Ile Gln Asn
            965                 970                 975

Leu Lys Ser Leu Ala Asp Tyr Leu Val Lys Lys Ser Val Trp Ile Ile
        980                 985                 990

Gly Gly Asp Gly Trp Ala Tyr Asp Ile Asp Phe Gly Gly Ile Asp His
    995                 1000                1005

Val Ile Ala Ser Gly Arg Asn Val Asn Ile Leu Val Met Asp Thr
    1010                1015                1020

Glu Val Tyr Ser Asn Thr Gly Gly Gln Ser Ser Lys Ala Thr Pro
    1025                1030                1035

Lys Ala Ala Val Ala Lys Phe Ala Ala Ser Gly Lys Pro Ala Gln
    1040                1045                1050

Lys Lys Asp Met Gly Leu Met Ala Met Asn Tyr Gly Asn Val Tyr
    1055                1060                1065

Val Ala Ser Val Ala Leu Gly Ala Lys Asp Asp Gln Thr Leu Lys
    1070                1075                1080

Ala Phe Leu Glu Ala Glu Ala Phe Asp Gly Pro Ser Ile Ile Ile
    1085                1090                1095

Ala Tyr Ser His Cys Ile Ala His Gly Ile Asn Met Thr Thr Gly
    1100                1105                1110

Met Asn Gln Gln Lys Ala Leu Val Glu Ser Gly Arg Trp Leu Leu
    1115                1120                1125

Tyr Arg Tyr Asn Pro Leu Leu Gln Glu Gln Gly Lys Asn Pro Leu
    1130                1135                1140

Gln Leu Asp Met Arg Ser Pro Thr Gln Ser Val Glu Gln Ser Met
    1145                1150                1155

Tyr Gln Glu Asn Arg Phe Lys Met Leu Thr Lys Ser Lys Pro Glu
    1160                1165                1170

Val Ala Lys Gln Leu Leu Glu Gln Ala Gln Ala Glu Val Asp Ala
    1175                1180                1185

Arg Trp Gln Met Tyr Gln Tyr Leu Ala Ser Arg
    1190                1195

<210> SEQ ID NO 33
<211> LENGTH: 700
<212> TYPE: PRT
<213> ORGANISM: E. coli

<400> SEQUENCE: 33

Met Ala Asn Gly Trp Thr Gly Asn Ile Leu Arg Val Asn Leu Thr Thr
1               5                   10                  15

Gly Asn Ile Thr Leu Glu Asp Ser Ser Lys Phe Lys Ser Phe Val Gly
            20                  25                  30
```

```
Gly Met Gly Phe Gly Tyr Lys Ile Met Tyr Asp Glu Val Pro Pro Gly
        35                  40                  45

Thr Lys Pro Phe Asp Glu Ala Asn Lys Leu Val Phe Ala Thr Gly Pro
 50                  55                  60

Leu Thr Gly Ser Gly Ala Pro Cys Ser Ser Arg Val Asn Ile Thr Ser
 65                  70                  75                  80

Leu Ser Thr Phe Thr Lys Gly Asn Leu Val Val Asp Ala His Met Gly
                 85                  90                  95

Gly Phe Phe Ala Ala Gln Met Lys Phe Ala Gly Tyr Asp Val Ile Ile
                100                 105                 110

Ile Glu Gly Lys Ala Lys Ser Pro Val Trp Leu Lys Ile Lys Asp Asp
            115                 120                 125

Lys Val Ser Leu Glu Lys Ala Asp Phe Leu Trp Gly Lys Gly Thr Arg
130                 135                 140

Ala Thr Thr Glu Glu Ile Cys Arg Leu Thr Ser Pro Glu Thr Cys Val
145                 150                 155                 160

Ala Ala Ile Gly Gln Ala Gly Glu Asn Leu Val Pro Leu Ser Gly Met
                165                 170                 175

Leu Asn Ser Arg Asn His Ser Gly Gly Ala Gly Thr Gly Ala Ile Met
                180                 185                 190

Gly Ser Lys Asn Leu Lys Ala Ile Ala Val Glu Gly Thr Lys Gly Val
            195                 200                 205

Asn Ile Ala Asp Arg Gln Glu Met Lys Arg Leu Asn Asp Tyr Met Met
210                 215                 220

Thr Glu Leu Ile Gly Ala Asn Asn Asn His Val Pro Ser Thr Pro
225                 230                 235                 240

Gln Ser Trp Ala Glu Tyr Ser Asp Pro Lys Ser Arg Trp Thr Ala Arg
                245                 250                 255

Lys Gly Leu Phe Trp Gly Ala Ala Glu Gly Gly Pro Ile Glu Thr Gly
                260                 265                 270

Glu Ile Pro Pro Gly Asn Gln Asn Thr Val Gly Phe Arg Thr Tyr Lys
            275                 280                 285

Ser Val Phe Asp Leu Gly Pro Ala Ala Glu Lys Tyr Thr Val Lys Met
290                 295                 300

Ser Gly Cys His Ser Cys Pro Ile Arg Cys Met Thr Gln Met Asn Ile
305                 310                 315                 320

Pro Arg Val Lys Glu Phe Gly Val Pro Ser Thr Gly Gly Asn Thr Cys
                325                 330                 335

Val Ala Asn Phe Val His Thr Thr Ile Phe Pro Asn Gly Pro Lys Asp
                340                 345                 350

Phe Glu Asp Lys Asp Asp Gly Arg Val Ile Gly Asn Leu Val Gly Leu
            355                 360                 365

Asn Leu Phe Asp Asp Tyr Gly Leu Trp Cys Asn Tyr Gly Gln Leu His
370                 375                 380

Arg Asp Phe Thr Tyr Cys Tyr Ser Lys Gly Val Phe Lys Arg Val Leu
385                 390                 395                 400

Pro Ala Glu Glu Tyr Ala Glu Ile Arg Trp Asp Gln Leu Glu Ala Gly
                405                 410                 415

Asp Val Asn Phe Ile Lys Asp Phe Tyr Tyr Arg Leu Ala His Arg Val
                420                 425                 430

Gly Glu Leu Ser His Leu Ala Asp Gly Ser Tyr Ala Ile Ala Glu Arg
            435                 440                 445
```

```
Trp Asn Leu Gly Glu Glu Tyr Trp Gly Tyr Ala Lys Asn Lys Leu Trp
            450                 455                 460

Ser Pro Phe Gly Tyr Pro Val His His Ala Asn Glu Ala Ser Ala Gln
465                 470                 475                 480

Val Gly Ser Ile Val Asn Cys Met Phe Asn Arg Asp Cys Met Thr His
                485                 490                 495

Thr His Ile Asn Phe Ile Gly Ser Gly Leu Pro Leu Lys Leu Gln Arg
            500                 505                 510

Glu Val Ala Lys Glu Leu Phe Gly Ser Glu Asp Ala Tyr Asp Glu Thr
            515                 520                 525

Lys Asn Tyr Thr Pro Ile Asn Asp Ala Lys Ile Lys Tyr Ala Lys Trp
530                 535                 540

Ser Leu Leu Arg Val Cys Leu His Asn Ala Val Thr Leu Cys Asn Trp
545                 550                 555                 560

Val Trp Pro Met Thr Val Ser Pro Leu Lys Ser Arg Asn Tyr Arg Gly
                565                 570                 575

Asp Leu Ala Leu Glu Ala Lys Phe Phe Lys Ala Ile Thr Gly Glu Glu
            580                 585                 590

Met Thr Gln Glu Lys Leu Asp Leu Ala Ala Glu Arg Ile Phe Thr Leu
            595                 600                 605

His Arg Ala Tyr Thr Val Lys Leu Met Gln Thr Lys Asp Met Arg Asn
610                 615                 620

Glu His Asp Leu Ile Cys Ser Trp Val Phe Asp Lys Asp Pro Gln Ile
625                 630                 635                 640

Pro Val Phe Thr Glu Gly Thr Asp Lys Met Asp Arg Asp Met His
                645                 650                 655

Ala Ser Leu Thr Met Phe Tyr Lys Glu Met Gly Trp Asp Pro Gln Leu
            660                 665                 670

Gly Cys Pro Thr Arg Glu Thr Leu Gln Arg Leu Gly Leu Glu Asp Ile
            675                 680                 685

Ala Ala Asp Leu Ala Ala His Asn Leu Leu Pro Ala
            690                 695                 700

<210> SEQ ID NO 34
<211> LENGTH: 208
<212> TYPE: PRT
<213> ORGANISM: E. coli

<400> SEQUENCE: 34

Met Asn Pro Val Asp Arg Pro Leu Leu Asp Ile Gly Leu Thr Arg Leu
1               5                   10                  15

Glu Phe Leu Arg Ile Ser Gly Lys Gly Leu Ala Gly Leu Thr Ile Ala
            20                  25                  30

Pro Ala Leu Leu Ser Leu Leu Gly Cys Lys Gln Glu Asp Ile Asp Ser
            35                  40                  45

Gly Thr Val Gly Leu Ile Asn Thr Pro Lys Gly Val Leu Val Thr Gln
        50                  55                  60

Arg Ala Arg Cys Thr Gly Cys His Arg Cys Glu Ile Ser Cys Thr Asn
65                  70                  75                  80

Phe Asn Asp Gly Ser Val Gly Thr Phe Phe Ser Arg Ile Lys Ile His
                85                  90                  95

Arg Asn Tyr Phe Phe Gly Asp Asn Gly Val Gly Ser Gly Gly Gly Leu
            100                 105                 110

Tyr Gly Asp Leu Asn Tyr Thr Ala Asp Thr Cys Arg Gln Cys Lys Glu
            115                 120                 125
```

```
Pro Gln Cys Met Asn Val Cys Pro Ile Gly Ala Ile Thr Trp Gln Gln
        130                 135                 140
Lys Glu Gly Cys Ile Thr Val Asp His Lys Arg Cys Ile Gly Cys Ser
145                 150                 155                 160
Ala Cys Thr Thr Ala Cys Pro Trp Met Met Ala Thr Val Asn Thr Glu
                165                 170                 175
Ser Lys Lys Ser Ser Lys Cys Val Leu Cys Gly Glu Cys Ala Asn Ala
                180                 185                 190
Cys Pro Thr Gly Ala Leu Lys Ile Ile Glu Trp Lys Asp Ile Thr Val
                195                 200                 205

<210> SEQ ID NO 35
<211> LENGTH: 1180
<212> TYPE: PRT
<213> ORGANISM: Gilliamella apicola

<400> SEQUENCE: 35

Met Ile Ile Ser Asp Ala Asn Ser Ala Val Ser Ser Val Ala Tyr Arg
1               5                   10                  15
Ala Asn Glu Val Ile Ala Ile Tyr Pro Ile Thr Pro Ser Ser Ser Met
                20                  25                  30
Ala Glu Gln Ala Ser Thr Trp Ala Glu Phe Asp Lys Pro Asn Val Phe
            35                  40                  45
Gly Asp Ile Pro Arg Val Val Glu Met Gln Ser Glu Ala Gly Ala Ile
        50                  55                  60
Ala Thr Val His Gly Ala Leu Met Thr Gly Ala Leu Ala Thr Ser Phe
65                  70                  75                  80
Thr Ser Ser Gln Gly Leu Leu Leu Met Ile Pro Ser Leu Tyr Lys Ile
                85                  90                  95
Ala Gly Glu Leu Thr Pro Phe Val Leu His Val Ala Ala Arg Thr Val
                100                 105                 110
Ala Thr His Ala Leu Ser Ile Phe Gly Asp His Ser Asp Val Met Ser
            115                 120                 125
Val Arg Gln Thr Gly Phe Ala Met Leu Cys Ser Ser Ser Val Gln Glu
        130                 135                 140
Ala Gln Asp Leu Ala Leu Ile Ser Gln Ile Ala Ser Phe Lys Ser Arg
145                 150                 155                 160
Ile Pro Phe Val His Phe Asp Gly Phe Arg Thr Ser His Glu Val
                165                 170                 175
Asn Lys Ile Tyr Pro Leu Ser Asp Glu Asp Ile His Asp Leu Leu Pro
                180                 185                 190
His Glu Ala Ile Lys Ala Tyr Arg Ser Arg Ala Leu Thr Pro Asp Lys
            195                 200                 205
Pro Met Ile Arg Gly Thr Ser Ala Asn Pro Asp Thr Tyr Phe Gln Cys
        210                 215                 220
Arg Glu Ala Ile Asn Ser Tyr Tyr Asp Asn Ala Tyr Gln His Val Val
225                 230                 235                 240
Asp Ala Met Thr Asp Phe Glu Lys Gln Thr Gly Arg Lys Tyr Gln Pro
                245                 250                 255
Phe Glu Tyr Tyr Gly Ala Ser Asp Ala Glu Arg Ile Ile Val Ile Met
                260                 265                 270
Gly Ser Gly Ala Ser Thr Ser Lys Glu Val Ile Asp Tyr Leu Leu Lys
            275                 280                 285
Glu Asn Gln Lys Val Gly Val Val Ile Val Arg Leu Phe Arg Pro Phe
```

```
            290                 295                 300
Ser Ala Gln His Leu Leu Ala Val Ile Pro Asp Ser Val Lys Lys Ile
305                 310                 315                 320

Ala Val Leu Asp Arg Thr Lys Glu Pro Gly Ala Gln Ala Glu Pro Leu
                325                 330                 335

Tyr Leu Asp Ile Met Thr Ala Phe Ala Glu Ser Leu Ser Arg Gly Glu
                340                 345                 350

Arg Asn Thr Ile Pro Gln Ile Val Gly Gly Arg Tyr Gly Leu Ser Ser
                355                 360                 365

Lys Glu Phe Asp Pro Arg Ser Val Leu Gly Ile Phe Asn Glu Leu Ser
        370                 375                 380

Leu Glu Lys Pro Arg Pro Arg Phe Thr Val Gly Ile Tyr Asp Asp Ile
385                 390                 395                 400

Thr Gly Leu Ser Leu Pro Leu Pro Asp Lys Thr Ile Pro Gln Lys Ser
                405                 410                 415

Ala Leu Glu Ala Leu Phe Tyr Gly Leu Gly Ser Asp Gly Thr Val Ser
                420                 425                 430

Ala Thr Lys Asn Asn Ile Lys Ile Gly Asp Ser Ser Pro Phe Tyr
        435                 440                 445

Val Gln Gly Tyr Phe Val Tyr Asp Ser Lys Lys Ala Gly Gly Leu Thr
        450                 455                 460

Thr Ser His Leu Arg Val Asn Leu Asp Pro Ile Asp Ser Pro Tyr Leu
465                 470                 475                 480

Ile Thr Ser Ala His Phe Ile Gly Cys His Gln Asp Gln Phe Ile Asp
                485                 490                 495

Lys Tyr Gln Ile Val Asp Lys Leu Lys Asn Asp Gly Ile Phe Leu Leu
                500                 505                 510

Asn Thr Pro Tyr Asn Lys Asp Glu Ile Trp His Arg Leu Pro Lys Glu
                515                 520                 525

Val Gln Val Gln Leu Ile Lys Lys Arg Ala His Phe Tyr Ile Ile Asn
        530                 535                 540

Ala Ala Lys Ile Ala Arg Glu Cys Asn Leu Gly Ala Arg Ile Asn Thr
545                 550                 555                 560

Val Met Gln Ala Ala Phe Phe His Leu Ser Asp Ile Phe Lys Asn Asp
                565                 570                 575

Phe Ser Ile Ser Gln Leu Lys Glu Val Ile Ala Lys Ser Tyr Ser Ser
                580                 585                 590

Lys Gly Gln Glu Leu Val Glu Asn Asn Trp Lys Ala Leu Asp Leu Ala
        595                 600                 605

Ile Thr Ser Leu Glu Gln Ile Pro Leu Asn Cys Val Asp Gln Ser Ser
        610                 615                 620

Pro Ser Met Pro Pro Ile Val Pro Asn Asn Ala Pro Asp Phe Val Lys
625                 630                 635                 640

Thr Val Thr Ala Thr Met Leu Ala Gly Leu Gly Asp Ser Leu Pro Val
                645                 650                 655

Ser Ala Phe Pro Pro Asp Gly Ala Trp Pro Thr Gly Thr Thr Lys Trp
                660                 665                 670

Glu Lys Arg Asn Ile Ala Glu Glu Ile Pro Ile Trp Lys Ser Glu Leu
        675                 680                 685

Cys Thr Gln Cys Asn His Cys Ala Val Ala Cys Pro His Ala Ala Ile
        690                 695                 700

Arg Ala Lys Val Val Glu Pro Asp Ala Met Leu Asn Ala Pro Asp Thr
705                 710                 715                 720
```

```
Leu Glu Ser Leu Glu Val Lys Ala Arg Asp Met Lys Gly Gln Arg Tyr
                725                 730                 735

Val Leu Gln Val Ala Pro Glu Asp Cys Thr Gly Cys Asn Leu Cys Val
            740                 745                 750

Glu Val Cys Pro Ser Arg Asp Arg Asn Asn Phe Asp Ile Lys Ala Ile
        755                 760                 765

Asn Met Gln Pro Arg Ile Asp Asn Leu Asp Thr Gln Arg Val Asn Phe
    770                 775                 780

Glu Phe Phe Ser Ala Leu Pro Asp Arg Asp Ile Lys Ser Leu Asp Arg
785                 790                 795                 800

Ile Asp Ile Arg Thr Ser Gln Leu Ile Thr Pro Leu Phe Glu Tyr Ser
                805                 810                 815

Gly Ala Cys Ala Gly Cys Gly Glu Thr Pro Tyr Ile Lys Leu Leu Thr
            820                 825                 830

Gln Leu Tyr Gly Asp His Leu Ala Ile Ala Asn Ala Thr Gly Cys Ser
        835                 840                 845

Ser Ile Tyr Gly Gly Asn Leu Pro Ser Thr Pro Tyr Thr Thr Asp Arg
    850                 855                 860

Ser Gly Arg Gly Pro Ala Trp Ala Asn Ser Leu Phe Glu Asp Asn Ala
865                 870                 875                 880

Glu Phe Ala Leu Gly Tyr Arg Ile Thr Tyr Asn Gln His Arg Lys Arg
                885                 890                 895

Ala Leu Arg Leu Leu Asp His Leu Ala Gly Glu Ile Ser Pro Glu Ile
            900                 905                 910

Val Ile Thr Leu Gln Ser Ser Asp Ala Thr Ile Ala Glu Lys Arg Thr
        915                 920                 925

Gln Val Asp Leu Leu Arg Glu Gln Leu Lys His Ile Asp Ser Ala Glu
    930                 935                 940

Ala Lys Glu Leu Leu Glu Asp Thr Asn Tyr Leu Ile Asp Lys Ser Val
945                 950                 955                 960

Trp Ala Ile Gly Gly Asp Gly Trp Ala Tyr Asp Ile Gly Phe Gly Gly
                965                 970                 975

Leu Asp His Val Met Ser Leu Thr Asp Asn Val Asn Ile Leu Val Leu
            980                 985                 990

Asp Thr Gln Cys Tyr Ser Asn Thr  Gly Gly Gln Gln Ser  Lys Ala Thr
        995                 1000                1005

Pro Met  Gly Ala Val Ser Lys  Phe Ala Asp Leu Gly  Lys His Lys
    1010                 1015                 1020

Ala Arg  Lys Asp Leu Gly Val  Ser Ile Met Met Tyr  Gly His Val
    1025                 1030                 1035

Tyr Val  Ala Gln Val Ala Leu  Gly Ser Gln Leu Asn  Gln Thr Leu
    1040                 1045                 1050

Lys Ala  Leu Gln Glu Ala Glu  Ala Tyr Asp Gly Pro  Ser Leu Val
    1055                 1060                 1065

Ile Ala  Tyr Ser Pro Cys Glu  Glu His Gly Tyr Asp  Leu Ala Lys
    1070                 1075                 1080

Ser His  Glu Gln Met Lys Asp  Leu Val Lys Ser Gly  Phe Trp Pro
    1085                 1090                 1095

Leu Tyr  Arg Tyr Asp Pro Arg  Arg Ser Ala Glu Gly  Lys Pro Gly
    1100                 1105                 1110

Leu Val  Leu Asp Ser Lys Ser  Pro Asn Ser Glu Ala  Leu Ser Ser
    1115                 1120                 1125
```

-continued

Ile Leu Leu Lys Glu Gln Arg Phe Arg Arg Leu Glu Thr Leu Glu
    1130                1135                1140

Pro Thr Val Ala Asn Ile Leu His Glu Arg Ser Thr Lys Met Val
    1145                1150                1155

Glu Ser Lys Tyr Arg Phe Leu Gln Met Leu Ser Ser Tyr Ser Asp
    1160                1165                1170

Ile Glu Thr Pro Pro Asp Ser
    1175            1180

<210> SEQ ID NO 36
<211> LENGTH: 440
<212> TYPE: PRT
<213> ORGANISM: Nostoc sp.

<400> SEQUENCE: 36

Met Ser Asn Gln Gly Ala Phe Asp Gly Ala Ala Asn Val Glu Ser Gly
 1               5                  10                  15

Ser Arg Val Phe Val Tyr Glu Val Val Gly Met Arg Gln Asn Glu Glu
            20                  25                  30

Thr Asp Gln Thr Asn Tyr Pro Ile Arg Lys Ser Gly Ser Val Phe Ile
        35                  40                  45

Arg Val Pro Tyr Asn Arg Met Asn Gln Glu Met Gln Arg Ile Thr Arg
    50                  55                  60

Leu Gly Gly Lys Ile Val Thr Ile Gln Thr Val Ser Ala Leu Gln Gln
65                  70                  75                  80

Leu Asn Gly Arg Thr Thr Ile Ala Thr Val Thr Asp Ala Ser Ser Glu
                85                  90                  95

Ile Ala Lys Ser Glu Gly Asn Gly Lys Ala Thr Pro Val Lys Thr Asp
            100                 105                 110

Ser Gly Ala Lys Ala Phe Ala Lys Pro Pro Ala Glu Gln Leu Lys
            115                 120                 125

Lys Lys Asp Asn Lys Gly Asn Thr Met Thr Gln Ala Lys Ala Lys His
130                 135                 140

Ala Asp Val Pro Val Asn Leu Tyr Arg Pro Asn Ala Pro Phe Ile Gly
145                 150                 155                 160

Lys Val Ile Ser Asn Glu Pro Leu Val Lys Glu Gly Ile Gly Ile
                165                 170                 175

Val Gln His Ile Lys Phe Asp Leu Thr Gly Gly Asn Leu Lys Tyr Ile
            180                 185                 190

Glu Gly Gln Ser Ile Gly Ile Ile Pro Pro Gly Val Asp Lys Asn Gly
            195                 200                 205

Lys Pro Glu Lys Leu Arg Leu Tyr Ser Ile Ala Ser Thr Arg His Gly
    210                 215                 220

Asp Asp Val Asp Asp Lys Thr Ile Ser Leu Cys Val Arg Gln Leu Glu
225                 230                 235                 240

Tyr Lys His Pro Glu Ser Gly Glu Thr Val Tyr Gly Val Cys Ser Thr
                245                 250                 255

Tyr Leu Thr His Ile Glu Pro Gly Ser Glu Val Lys Ile Thr Gly Pro
            260                 265                 270

Val Gly Lys Glu Met Leu Leu Pro Asp Asp Pro Glu Ala Asn Val Ile
        275                 280                 285

Met Leu Ala Thr Gly Thr Gly Ile Ala Pro Met Arg Thr Tyr Leu Trp
    290                 295                 300

Arg Met Phe Lys Asp Ala Glu Arg Ala Ala Asn Pro Glu Tyr Gln Phe
305                 310                 315                 320

```
Lys Gly Phe Ser Trp Leu Val Phe Gly Val Pro Thr Pro Asn Ile
            325                 330                 335

Leu Tyr Lys Glu Glu Leu Glu Glu Ile Gln Gln Lys Tyr Pro Asp Asn
        340                 345                 350

Phe Arg Leu Thr Tyr Ala Ile Ser Arg Glu Gln Lys Asn Pro Gln Gly
            355                 360                 365

Gly Arg Met Tyr Ile Gln Asp Arg Val Ala Glu His Ala Asp Glu Leu
        370                 375                 380

Trp Gln Leu Ile Lys Asn Gln Lys Thr His Thr Tyr Ile Cys Gly Leu
385                 390                 395                 400

Arg Gly Met Glu Glu Gly Ile Asp Ala Ala Leu Ser Ala Ala Ala
            405                 410                 415

Lys Glu Gly Val Thr Trp Ser Asp Tyr Gln Lys Asp Leu Lys Lys Ala
            420                 425                 430

Gly Arg Trp His Val Glu Thr Tyr
            435                 440

<210> SEQ ID NO 37
<211> LENGTH: 402
<212> TYPE: PRT
<213> ORGANISM: Synechococcus sp.

<400> SEQUENCE: 37

Met Tyr Gly Ile Thr Ser Thr Ala Asn Ser Thr Gly Asn Gln Ser Tyr
1               5                   10                  15

Ala Asn Arg Leu Phe Ile Tyr Glu Val Val Gly Leu Gly Gly Asp Gly
            20                  25                  30

Arg Asn Glu Asn Ser Leu Val Arg Lys Ser Gly Thr Thr Phe Ile Thr
        35                  40                  45

Val Pro Tyr Ala Arg Met Asn Gln Glu Met Gln Arg Ile Thr Lys Leu
    50                  55                  60

Gly Gly Lys Ile Val Ser Ile Arg Pro Ala Glu Asp Ala Ala Gln Ile
65                  70                  75                  80

Val Ser Glu Gly Gln Ser Ser Ala Gln Ala Ser Ala Gln Ser Pro Met
            85                  90                  95

Ala Ser Ser Thr Lys Ile Val His Pro Lys Thr Thr Asp Thr Ser Val
            100                 105                 110

Pro Val Asn Ile Tyr Arg Pro Lys Thr Pro Phe Leu Gly Lys Cys Ile
            115                 120                 125

Glu Asn Tyr Glu Leu Val Asp Glu Gly Ser Gly Thr Val Arg His
        130                 135                 140

Val Thr Phe Asp Ile Ser Glu Gly Asp Leu Arg Tyr Leu Glu Gly Gln
145                 150                 155                 160

Ser Ile Gly Ile Ile Pro Pro Gly Glu Asp Lys Asn Gly Lys Pro His
            165                 170                 175

Lys Leu Arg Leu Tyr Ser Ile Ala Ser Thr Arg His Gly Asp Met Glu
            180                 185                 190

Asp Asn Lys Thr Val Ser Leu Cys Val Arg Gln Leu Glu Tyr Gln Asp
        195                 200                 205

Pro Glu Ser Gly Glu Thr Val Tyr Gly Val Cys Ser Thr Tyr Leu Cys
    210                 215                 220

Asn Leu Pro Val Gly Thr Asp Asp Val Lys Ile Thr Gly Pro Val Gly
225                 230                 235                 240

Lys Glu Met Leu Leu Pro Asp Asp Glu Asp Ala Thr Val Val Met Leu
```

```
                    245                 250                 255
Ala Thr Gly Thr Gly Ile Ala Pro Phe Arg Ala Phe Leu Trp Arg Met
                260                 265                 270

Phe Lys Glu Gln His Glu Asp Tyr Lys Phe Lys Gly Lys Ala Trp Leu
            275                 280                 285

Ile Phe Gly Val Pro Tyr Thr Ala Asn Ile Leu Tyr Lys Asp Asp Phe
        290                 295                 300

Glu Lys Met Ala Ala Glu Asn Pro Asp Asn Phe Arg Leu Thr Tyr Ala
305                 310                 315                 320

Ile Ser Arg Glu Gln Lys Thr Ala Asp Gly Gly Lys Val Tyr Val Gln
                325                 330                 335

Ser Arg Val Ser Glu Tyr Ala Asp Glu Leu Phe Glu Met Ile Gln Lys
            340                 345                 350

Pro Asn Thr His Val Tyr Met Cys Gly Leu Lys Gly Met Gln Pro Pro
        355                 360                 365

Ile Asp Glu Thr Phe Thr Ala Glu Ala Glu Lys Arg Gly Leu Asn Trp
    370                 375                 380

Glu Glu Met Arg Arg Ser Met Lys Lys Glu His Arg Trp His Val Glu
385                 390                 395                 400

Val Tyr

<210> SEQ ID NO 38
<211> LENGTH: 248
<212> TYPE: PRT
<213> ORGANISM: E. coli

<400> SEQUENCE: 38

Met Ala Asp Trp Val Thr Gly Lys Val Thr Lys Val Gln Asn Trp Thr
1               5                   10                  15

Asp Ala Leu Phe Ser Leu Thr Val His Ala Pro Val Leu Pro Phe Thr
            20                  25                  30

Ala Gly Gln Phe Thr Lys Leu Gly Leu Glu Ile Asp Gly Glu Arg Val
        35                  40                  45

Gln Arg Ala Tyr Ser Tyr Val Asn Ser Pro Asp Asn Pro Asp Leu Glu
    50                  55                  60

Phe Tyr Leu Val Thr Val Pro Asp Gly Lys Leu Ser Pro Arg Leu Ala
65                  70                  75                  80

Ala Leu Lys Pro Gly Asp Glu Val Gln Val Ser Glu Ala Ala Gly
                85                  90                  95

Phe Phe Val Leu Asp Glu Val Pro His Cys Glu Thr Leu Trp Met Leu
            100                 105                 110

Ala Thr Gly Thr Ala Ile Gly Pro Tyr Leu Ser Ile Leu Gln Leu Gly
        115                 120                 125

Lys Asp Leu Asp Arg Phe Lys Asn Leu Val Leu Val His Ala Ala Arg
    130                 135                 140

Tyr Ala Ala Asp Leu Ser Tyr Leu Pro Leu Met Gln Glu Leu Glu Lys
145                 150                 155                 160

Arg Tyr Glu Gly Lys Leu Arg Ile Gln Thr Val Val Ser Arg Glu Thr
                165                 170                 175

Ala Ala Gly Ser Leu Thr Gly Arg Ile Pro Ala Leu Ile Glu Ser Gly
            180                 185                 190

Glu Leu Glu Ser Thr Ile Gly Leu Pro Met Asn Lys Glu Thr Ser His
        195                 200                 205

Val Met Leu Cys Gly Asn Pro Gln Met Val Arg Asp Thr Gln Gln Leu
```

```
              210                 215                 220
Leu Lys Glu Thr Arg Gln Met Thr Lys His Leu Arg Arg Arg Pro Gly
225                 230                 235                 240

His Met Thr Ala Glu His Tyr Trp
                245
```

METABOLIC ENGINEERING FOR MICROBIAL PRODUCTION OF TERPENOID PRODUCTS

CROSS REFERENCE TO RELATED APPLICATIONS

This application claims priority to U.S. Provisional Application No. 62/450,707 filed Jan. 26, 2017, the content of which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Jan. 26, 2018, is named MAN-009PC_ST25 and is 125,103 bytes in size.

BACKGROUND

The food and beverage industries as well as other industries such as the perfume, cosmetic and health care industries routinely use terpenes and/or terpenoid products, including for use as flavors and fragrances. However, factors such as: (i) the availability and high price of the plant raw material; (ii) the relatively low terpene content in plant; and (iii) the tedious and inefficient extraction processes to produce sufficient quantities of terpene products on an industrial scale all have stimulated research on the biosynthesis of terpenes using plant-independent systems. Consequently, effort has been expended in developing technologies to engineer microorganisms for converting renewable resources such as glucose into terpenoid products. By comparison with traditional methods, microorganisms have the advantage of fast growth without the need for land to sustain development.

There are two major biosynthetic routes for the essential isoprenoid precursors isopentenyl diphosphate (IPP) and dimethylallyl diphosphate (DMAPP), the mevalonate (MVA) pathway and the methylerythritol phosphate (MEP) pathway. The MVA pathway is found in most eukaryotes, archaea and a few eubacteria. The MEP pathway is found in eubacteria, the chloroplasts of plants, cyanobacteria, algae and apicomplexan parasites. *E. coli* and other Gram-negative bacteria utilize the MEP pathway to synthesize IPP and DMAPP metabolic precursors. While the MEP pathway provides a theoretically better stoichiometric yield over the MVA pathway, the MEP pathway in *E. coli* and in other bacteria has a variety of intrinsic regulation mechanisms that control and/or limit carbon flux through the pathway. See, Zhao et al., *Methylerythritol Phosphate Pathway of Isoprenoid Biosynthesis, Annu Rev. Biochem.* 2013; 82:497-530; Ajikumar P K, et al., *Isoprenoid pathway optimization for Taxol precursor overproduction in Escherichia coli. Science* 2010; 330-70-74.

Microbial strains and methods for improving carbon flux through the MEP pathway and through recombinant downstream terpene and terpenoid synthesis pathways are needed for industrial-scale production of terpenes and terpenoids in bacterial systems.

SUMMARY OF THE INVENTION

In various aspects, the invention relates to methods and bacterial strains for making terpene and terpenoid products. In certain aspects, the invention provides bacterial strains with improved carbon flux into the MEP pathway and to a downstream recombinant synthesis pathway, to thereby increase terpene and/or terpenoid production by fermentation with inexpensive carbon sources (e.g., glucose).

In some aspects, the invention relates to bacterial strains that overexpress IspG and IspH, so as to provide increased carbon flux to 1-hydroxy-2-methyl-2-(E)-butenyl 4-diphosphate (HMBPP) intermediate, but with balanced expression to prevent accumulation of HMBPP at an amount that reduces cell growth or viability, or at an amount that inhibits MEP pathway flux and/or terpenoid production. Increasing expression of both IspG and IspH significantly increases titers of terpene and terpenoid products. In contrast, overexpression of IspG alone results in growth defects, while overexpression of IspH alone does not significantly impact product titer. HMBPP metabolite can act as a regulator or inhibitor of the MEP pathway, and may be toxic to the bacterial cells at certain levels. For example, in some embodiments, HMBPP does not accumulate at more than about 10 mg/g dry cell weight (DCW), or in some embodiments does not accumulate at more than about 5 mg/g of DCW, or at more than about 2 mg/g DCW. Thus, the balanced overexpression of IspG and IspH (e.g., favoring more IspH activity) is important to pull MEP carbon downstream through HMBPP to IPP while preventing its imbalance and accumulation.

In various embodiments, the bacterial strain overexpresses a balanced MEP pathway to move MEP carbon to the MEcPP intermediate, the substrate for IspG, and includes one or more genetic modifications to support the activities of IspG and IspH enzymes, which are Fe-sulfur cluster enzymes. Exemplary modifications include those that enhance the supply and transfer of electrons through the MEP pathway, and/or to terpene or terpenoid products. These include recombinant expression of one or more oxidoreductase enzymes, including oxidoreductases that oxidize pyruvate and/or lead to reduction of ferredoxin (which supplies electrons to the MEP pathway). An exemplary oxidoreductase is *E. coli* YdbK and orthologs and derivatives thereof.

In various embodiments, the microbial strain comprises an overexpression of or complementation with one or more of a flavodoxin (fldA), flavodoxin reductase, ferredoxin (fdx), and ferredoxin reductase.

In other aspects, the invention provides bacterial strains that overexpress PgpB or NudB, which dephosphorylate FPP to farnesol, and IPP and DMAPP to isoprenol and prenol, respectively. In these embodiments, the cell contains an additional product pull on the MEP pathway, while draining excess MEP carbon from the pathway outside the cell, and thereby avoiding intrinsic feedback inhibition mechanisms. Further, since these products accumulate outside the cell, they can be used to track carbon flux through the MEP pathway, even without a downstream terpenoid synthesis pathway installed. Thus, bacteria strains overexpressing PgpB and/or NudB are convenient tools for balancing the expression of MEP pathway genes. Additionally, or alternatively, in some embodiments, the bacterial strain overexpresses one or more strong synthases with sufficient product pull on the MEP pathway to avoid intrinsic feedback inhibition mechanisms. By way of example, in some embodiments, the synthase is *Artemisia annua* farnesene synthase.

For production of terpene or terpenoid product, the bacterial cell will contain a recombinant downstream pathway that produces the terpenoid from IPP and DMAPP precursors. In certain embodiments, the bacterial cell produces one or more terpenoid compounds, such as monoterpenoids, sesquiterpenoids, triterpenoids, and diterpenoids, among others. Such terpenoid compounds find use in perfumery (e.g. patchoulol), in the flavor industry (e.g., nootkatone), as sweeteners (e.g., steviol glycosides), as colorants, or as therapeutic agents (e.g., taxol).

The recovered terpene or terpenoid may be incorporated into a product (e.g., a consumer or industrial product). For example, the product may be a flavor product, a fragrance product, a sweetener, a cosmetic, a cleaning product, a detergent or soap, or a pest control product. The higher yields produced in embodiments of the invention can provide significant cost advantages as well as sustainability and quality control of the terpene or terpenoid ingredient.

Other aspects and embodiments of the invention will be apparent from the following detailed description of the invention.

BRIEF DESCRIPTION OF THE FIGURES

FIG. 16A shows the fold change in bacterial strains that produce terpenoid Product B. FIG. 16B shows the fold change in bacterial strains that produce terpenoid Product C. FIG. 16C shows the fold change in bacterial strains that produce terpenoid Product D. FIG. 16D shows the fold change in bacterial strains that produce terpenoid Product E.

FIG. 17A shows the fold change in bacterial strains that produce terpenoid Product B. FIG. 17B shows the fold change in bacterial strains that produce terpenoid Product C. FIG. 17C shows the fold change in bacterial strains that produce terpenoid Product D.

DETAILED DESCRIPTION OF THE INVENTION

Figure 1:
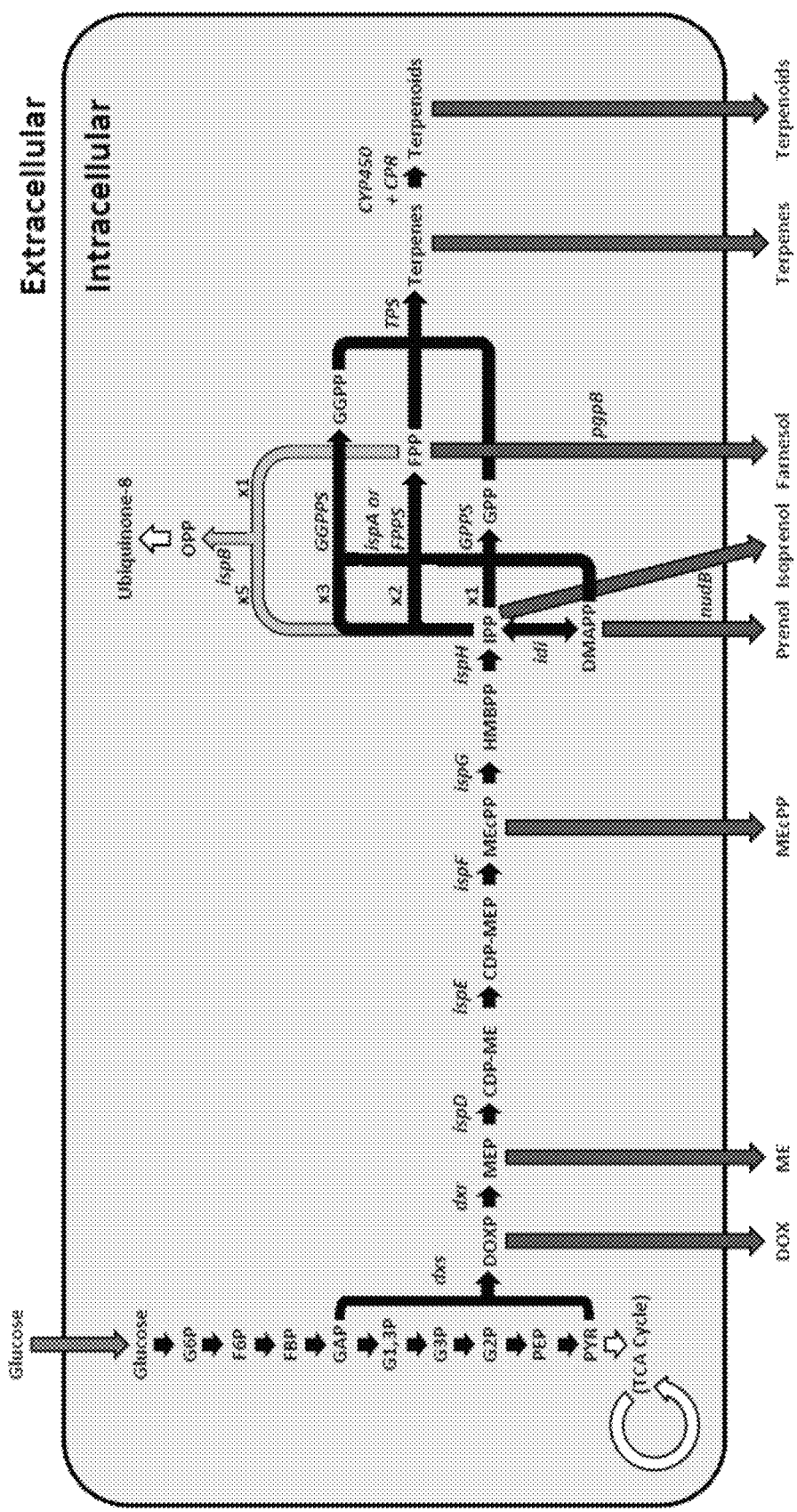
FIG. 1 is a schematic for terpenoid production through the MEP pathway. A bacterial cell is represented, taking in glucose as a carbon source. Glucose is converted to biomass through the TCA cycle or funneled through the MEP pathway to the desired terpenoid products. Glucose comes into the cell and is converted to pyruvate (PYR) with glyceraldehyde 3-phosphate as an intermediate (GAP). PYR and GAP are combined to make DOXP, which is converted to MEP and commits the pathway to FPP (going through MEcPP). DOX and ME are dephosphorylated products of DOXP and MEP, respectively. DOX, ME, and MEcPP are found outside the cell. The more flux that is forced into the MEP pathway, the more these products are found extracellularly. These side products can be used as markers of bottlenecks in the MEP pathway, and to identify targets for engineering. By overexpressing nudB or pgpB, IPP and DMAPP or FPP are dephosphorylated to prenol and isoprenol or farnesol, respectively, which accumulate outside the cell and can be used to alleviate intermediate accumulation and the activation of feedback inhibition of the MEP pathway. Black arrows show enzyme-mediated biochemical reactions towards terpenoids, light grey arrows show a competing side product, dark grey arrows show transport of a product outside of the cell, and white arrows show condensed pathways for simplicity.

In various aspects, the invention relates to bacterial strains and methods for making terpene and terpenoid products, the bacterial strains having improved carbon flux through the MEP pathway and to a downstream recombinant synthesis pathway. In various embodiments, the invention provides for increased terpene and/or terpenoid product yield by fermentation of the bacterial strains with carbon sources such as glucose, glycerol, sucrose, and others.

For example, in some aspects the invention provides a bacterial strain that produces isopentenyl diphosphate (IPP) and dimethylallyl diphosphate (DMAPP) through the MEP pathway, and converts the IPP and DMAPP to a terpene or terpenoid product through a downstream synthesis pathway. In the bacterial strain, IspG and IspH are overexpressed such that IspG activity and IspH activity are enhanced to provide increased carbon flux to 1-hydroxy-2-methyl-2-(E)-butenyl 4-diphosphate (HMBPP) intermediate, but balanced to prevent accumulation of HMBPP at an amount that significantly reduces cell growth, viability, MEP pathway flux, or product titer.

Increasing expression of both IspG and IspH can significantly increase titers of terpene and terpenoid products. Increasing expression of just IspG or IspH alone does not significantly improve titer. Further, overexpression of IspG alone can result in growth defects, which may relate to the observation that HMBPP (the intermediate in the MEP pathway produced by IspG, and consumed by IspH) is not found extracellularly, but is found 100% intracellularly. HMBPP metabolite appears to act as an inhibitor of the MEP pathway, and appears to be toxic to the bacterial cell at certain levels. Thus, the balance of activity between IspG and IspH is important to prevent HMBPP imbalance and accumulation.

HMBPP accumulation can be determined as an amount per dry cell weight (DCW). For example, in some embodiments, HMBPP does not accumulate at more than about 10 mg/g DCW, or in some embodiments does not accumulate at more than about 8 mg/g of DCW, or in some embodiments does not accumulate at more than about 5 mg/g of DCW, or in some embodiments does not accumulate at more than about 4 mg/g DCW, or in some embodiments does not accumulate at more than about 2 mg/g DCW. In some embodiments, HMBPP does not accumulate at more than about 1 mg/g DCW, or does not accumulate at more than about 0.5 mg/g DCW, or more than about 0.2 mg/g DCW, or more than about 0.1 mg/g DCW. The balanced overexpression of IspG and IspH (e.g., favoring more IspH activity) is important to pull MEP carbon downstream through HMBPP to IPP while preventing its imbalance and accumulation.

In some embodiments, IspG and IspH are overexpressed by introducing recombinant ispG and ispH genes into the bacterial strain. In other embodiments, the endogenous genes can be overexpressed by modifying, for example, the endogenous promoter or ribosomal binding site. When introducing recombinant ispG and/or ispH genes, the genes may optionally comprise one or more beneficial mutations.

In some embodiments, the additional gene may be substantially identical to the wild-type enzyme (e.g., the *E. coli* wild-type enzyme), or may be modified to increase activity or may be an IspG or IspH ortholog having similar, higher, or lower activity than the native bacterial (e.g., *E. coli*) enzyme. For example, with respect to IspG, the amino acid sequence may have 50% or more sequence identity with SEQ ID NO: 1, or at least about 60% sequence identity, or at least about 70% sequence identity, or at least about 80% sequence identity, or at least about 90% sequence identity, or at least about 95% sequence identity, or at least about 98% sequence identity with the amino acid sequence of SEQ ID NO:1. In some embodiments, from 1 to about 10, or from 1 to about 5 amino acid substitutions, deletions, and/or insertions are made to the IspG amino acid sequence (SEQ ID NO: 1) to alter the activity of the protein, including substitutions to one or more of the substrate binding site or active site. Modifications to E. coli or other IspG can be informed by construction of a homology model. For example, a suitable homolog for construction of an E. coli IspG homology model is disclosed in: Lee M, et al. *Biosynthesis of isoprenoids: crystal structure of the [4Fe-4S] cluster protein IspG. J Mol Biol.* 2010 Dec. 10; 404(4):600-10. An exemplary IspG mutant with improvements in activity has four amino acid substitutions with respect to the wild type E. coli enzyme (referred to herein as IspG').

Further, with respect to IspH, the amino acid sequence may have 50% or more sequence identity with SEQ ID NO:2, or at least about 60% sequence identity, or at least about 70% sequence identity, or at least about 80% sequence identity, or at least about 90% sequence identity, or at least about 95% sequence identity, or at least about 98% sequence identity with the amino acid sequence of SEQ ID NO:2. In some embodiments, from 1 to about 10, or from 1 to about 5, amino acid substitutions, deletions, and/or insertions are made to the IspH amino acid sequence (SEQ ID NO:2) to alter the activity of the protein, including substitutions to one or more of the substrate binding site or active site. Modifications to the IspH enzyme can be informed by available IspH structures, including Grawert, T., et al. *Structure of active IspH enzyme from Escherichia coli provides mechanistic insights into substrate reduction* 2009 Angew. Chem. Int. Ed. Engl. 48: 5756-5759.

Table 1 provides a list of alternative enzymes useful for constructing bacterial strains and/or modifying IspG or IspH enzymes for enhanced expression in bacterial cells or enhanced physical properties, each of which can be modified by amino acid substitution, deletion, and/or insertion. For example, the amino acid sequence may have 50% or more sequence identity, or at least about 60% sequence identity, or at least about 70% sequence identity, or at least about 80% sequence identity, or at least about 90% sequence identity, or at least about 95% sequence identity, or at least about 98% sequence identity with an amino acid sequence described in Table 1. In some embodiments, from 1 to about 10, or from 1 to about 5, amino acid substitutions, deletions, and/or insertions are made to a sequence of Table 1 to alter the activity of the protein, including substitutions to one or more of the substrate binding site or active site. In some embodiments, the IspG and/or IspH enzyme is an ortholog of the E. coli enzyme having improved properties or activity under conditions used for culturing.

TABLE 1

| Gene | Species | Accession number |
| --- | --- | --- |
| ispG | Bacillus subtilis | NP_390386.1 |
| ispG | Chloroboculum tepidum | NP_661053.1 |
| ispG | Synechocystis sp. PCC 6803 | WP_010872347.1 |
| ispH | Bacillus subtilis | NP_390395.2 |
| ispH | Burkholderia sp. MSh1 | WP_031398482.1 |
| ispH | Chloroboculum tepidum | NP_661187.1 |
| ispH | Stevia rebaudiana | ABB88836.2 |

TABLE 1-continued

| Gene | Species | Accession number |
| --- | --- | --- |
| ispH | Stevia rebaudiana | ALJ30091.1 |
| ispH | Synechocystis sp. PCC 6803 | WP_010873388.1 |

The expression of the recombinant IspG and IspH enzymes can be balanced, for example, by modifying the promoter strength, gene copy number, position of the genes in an operon, and/or modifying the ribosome binding site sequence of the ispG and/or ispH recombinant genes. When the expression and/or activity of IspG and IspH are balanced, HMBPP intermediate does not accumulate in cells substantially more than in a parent strain that does not comprise the recombinant or modified ispG and ispH genes. This is despite the substantial increase in carbon flux through the MEP pathway that is required for commercial production of terpenes and terpenoids by fermentation. This result is shown in FIG. 3, where strains overexpressing ispG and ispH, which can produce close to a 4-fold increase in product titer as compared to a control strain that does not overexpress ispG and ispH (FIG. 2), nevertheless do not accumulate HMBPP intermediate above that in the control.

In some embodiments, the activity and/or expression of recombinant IspH is higher than the activity and/or expression of the recombinant IspG. An IspG/IspH ratio that favors more H enzyme results in high flux through the MEP pathway relative to a strain favoring the IspG side of the ratio. IspG and IspH work sequentially to convert MEcPP to HMBPP, then to IPP. Increasing IspG accumulates a larger HMBPP pool (which can show inhibitory effects on strain growth), while increasing IspH shrinks the HMBPP pool as it is converted to IPP. Thus, the ideal balance between IspG and IspH enhances the rate of both HMBPP formation and consumption, while avoiding HMBPP accumulation, which significantly improves flux through the MEP pathway to the target terpenoid. A slight favoring of IspH over IspG can further improve productivity by 25%, to nearly 4 times the titers of the parent strain. See FIG. 2.

Thus, in some embodiments, the expression of the recombinant IspH is higher than the expression of the recombinant IspG. For example, the recombinant IspH and IspG enzymes can be expressed from an operon, with ispH positioned before ispG in the operon. The gene positioned first in the operon will be slightly favored for expression, providing an elegant balancing mechanism for IspH and IspG. In some embodiments, ispG can be positioned first, optionally together with other modifications, such as mutations to the RBS to reduce expression, or point mutations to one or both of IspG and IspH that balance activity at the level of enzyme productivity. In some embodiments, ispG and ispH are expressed in separate operons (e.g., monocistronic) and expression balanced using promoters or RBSs of different strengths.

In some embodiments, IspH and IspG are expressed together from an operon (with the ispH gene positioned before the ispG gene), and with the operon expressed under control of a strong promoter. While increasing promoter strength has a positive impact on productivity when ispH is positioned before ispG in the operon, increasing promoter strength can have a negative impact when ispG is positioned before ispH. See FIG. 7, using farnesol production as a surrogate for product.

Recombinant IspG and IspH enzymes can be expressed from a plasmid or the encoding genes may be integrated into the chromosome, and can be present in single or multiple copies, in some embodiments, for example, about 2 copies, about 5 copies, or about 10 copies per cell. Copy number can be controlled by use of plasmids with different copy number (as is well known in the art), or by incorporating multiple copies into the genome, e.g., by tandem gene duplication.

In some embodiments, the microbial strain has high flux through the MEP pathway, including for example, by overexpression of one or more MEP enzymes (e.g., in addition to IspG and IspH). With glucose as carbon source, the theoretical maximum for carbon entering the MEP pathway is about 30% in *E. coli*. Prior yields of MEP carbon reported in the literature are less than 1%. See, Zhou K, Zou R, Stephanopoulos G, Too H-P (2012) *Metabolite Profiling Identified Methylerythritol Cyclodiphosphate Efflux as a Limiting Step in Microbial Isoprenoid Production*. PLoS ONE 7(11): e47513. doi:10.1371/journal.pone.0047513. Overexpression and balancing of MEP pathway genes, in addition to other modifications described herein can pull carbon through the MEP pathway and into a downstream synthesis pathway to improve carbon flux through to terpene and/or terpenoid products.

The host cell (the bacterial strain) expresses an MEP pathway producing isopentenyl diphosphate (IPP) and dimethylallyl diphosphate (DMAPP). Specifically, glucose comes into the cell and is converted to pyruvate (PYR) with glyceraldehyde-3-phosphate as an intermediate (G3P or GAP). G3P and PYR are combined to make 1-deoxy-D-xylulose-5-phosphate (DOXP), which is converted to 2-C-methyl-D-erythritol 4-phosphate (MEP) and commits the pathway to IPP and DMAPP. DOX, ME, and MEcPP are found outside the cell. The more flux into the MEP pathway, the more these products are found extracellularly in strains with unbalanced pathways. See FIG. 1.

The MEP (2-C-methyl-D-erythritol 4-phosphate) pathway is also called the MEP/DOXP (2-C-methyl-D-erythritol 4-phosphate/1-deoxy-D-xylulose 5-phosphate) pathway or the non-mevalonate pathway or the mevalonic acid-independent pathway. The pathway typically involves action of the following enzymes: 1-deoxy-D-xylulose-5-phosphate synthase (Dxs), 1-deoxy-D-xylulose-5-phosphate reductoisomerase (Dxr, or IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), 1-hydroxy-2-methyl-2-(E)-butenyl 4-diphosphate reductase (IspH) and isopentenyl diphosphate isomerase (Idi). The MEP pathway, and the genes and enzymes that make up the MEP pathway, are described in U.S. Pat. No. 8,512,988, which is hereby incorporated by reference in its entirety. Thus, genes that make up the MEP pathway include dxs, dxr (or ispC), ispD, ispE, ispF, ispG, ispH, idi, and ispA. The amino acid sequences for MEP pathway enzymes are shown in the attached listing of Sequences.

IPP and DMAPP (the products of the MEP pathway) are the precursors of terpenes and terpenoids, including monoterpenoids, sesquiterpenoids, triterpenoids, and diterpenoids, which have particular utility in the flavor, fragrance, cosmetics, and food sectors. Synthesis of terpenes and terpenoids proceeds via conversion of IPP and DMAPP precursors to geranyl diphosphate (GPP), farnesyl diphosphate (FPP), or geranylgeranyl diphosphate (GGPP), through the action of a prenyl transferase enzyme (e.g., GPPS, FPPS, or GGPPS). Such enzymes are known, and are described for example in U.S. Pat. No. 8,927,241, WO 2016/073740, and WO 2016/029153, which are hereby incorporated by reference in their entireties.

In various embodiments, the invention results in substantial improvements in MEP carbon. As used herein, the term "MEP carbon" refers to the total carbon present as an input, intermediate, metabolite, or product of the MEP pathway. Metabolites include derivatives such as breakdown products, and products of phosphorylation and dephosphorylation. MEP carbon includes products and intermediates of downstream pathways including terpenoid synthesis pathways. For purposes of this disclosure, MEP carbon includes the following inputs, intermediates, and metabolites of the MEP pathway: D-glyceraldehyde 3-phosphate, pyruvate, 1-deoxy-D-xylulose-5-phosphate, 1-deoxy-D-xylulose, 2-C-methyl-D-erythritol-5-phosphate, 2-C-methyl-D-erythritol, 4-diphosphocytidyl-2-C-methyl-D-erythritol, 2-phospho-4-diphosphocytidyl-2-C-methyl-D-erythritol, 2C-methyl-D-erythritol 2,4-cyclodiphosphate, 1-hydroxy-2-methyl-2-(E)-butenyl 4-diphosphate, isopentenyl diphosphate, and dimethylallyl diphosphate. MEP carbon further includes intermediates and key metabolites in the downstream terpenoid synthesis pathway expressed by the cell. While the identity will vary based upon pathway and enzymes employed, such products include: geranyl diphosphate (GPP), farnesyl diphosphate (FPP), geranylgeranyl diphosphate (GGPP), or geranylfarnesyl diphosphate (FGPP); their monophosphorylated versions geranyl phosphate, farnesyl phosphate, geranylgeranyl phosphate, or geranylfarnesyl phosphate; their alcohols geraniol, farnesol, geranylgeraniol, or geranylfarnesol; as well as downstream terpene and terpenoid products. MEP carbon further includes compounds derived from FPP or pathways that use FPP, including squalene, undecaprenyl diphosphate (UPP), undecaprenyl phosphate, octaprenyl diphosphate (OPP), 4-hydroxybenzoate, 3-octaprenyl-4-hydroxybenzoate, 2-octaprenylphenol, 3-octaprenylbenzene-1,2-diol, 2-methoxy-6-octaprenyl-2-methoxy-1,4-benzoquinol, 6-methoxy-3-methyloctaprenyl-1,4-benzoquinol, 3-demethyluibquinol-8, ubiquinol-8, ubiquinone, 2-carboxy-1,4-naphthoquinol, demethylmenaquinol-8, menaquinol-8, and menaquinone. MEP carbon further includes isoprenol, prenol, isopentenyl phosphate, and dimethylallyl phosphate metabolites. MEP carbon (the intermediates and metabolites above) can be quantified by mass spectrometry (MS), such as tandem mass spectrometry (MS/MS) via triple quadrupole (QQQ) mass detector. An exemplary system is Agilent 6460 QQQ; alternatively, with quantitative time-of-flight (QTOF), time-of-flight (TOF), or ion trap mass detectors.

In some embodiments, the microbial strain has at least one additional copy of dxs, ispD, ispF, and/or idi genes, which can be rate limiting, and which can be expressed from an operon or module, either on a plasmid or integrated into the bacterial chromosome. In some embodiments, the bacterial strain has at least one additional copy of dxs and idi expressed as an operon/module; or dxs, ispD, ispF, and idi expressed as an operon or module. In some embodiments, the bacterial strain expresses dxs, dxr, ispD, ispE, ispF, and idi as recombinant genes, which are optionally expressed as 1, 2, or 3 individual operons or modules. The recombinant genes of the MEP pathway are expressed from one or more plasmids or are integrated into the chromosome. In these embodiments, the strain provides increased flux through the MEP pathway as compared to wild type.

Amino acid sequences for wild type *E. coli* enzymes Dxs, Dxr, IspD, IspE, IspF, and Idi are shown herein as SEQ ID NOS: 3 to 8. In various embodiments, enzymes having structural or sequence homology, and comparable functionality, can be employed (including bacterial homologs). For example, the amino acid sequence may have 50% or more sequence identity with any one of SEQ ID NOS:3-8, or at least about 60% sequence identity, or at least about 70% sequence identity, or at least about 80% sequence identity, or at least about 90% sequence identity, or at least about 95% sequence identity, or at least about 98% sequence identity with the amino acid sequence of any one of SEQ ID NO:3-8. In some embodiments, from 1 to about 10, or from 1 to about 5, amino acid substitutions, deletions, and/or insertions are made to the amino acid sequence (SEQ ID NO:3-8) to alter the activity of the protein, including substitutions to one or more of the substrate binding site or active site. Modifications to enzymes can be informed by construction of a homology model. Such mutants can be informed by enzyme structures available in the art, including Yajima S, et al., *Structure of 1-deoxy-D-xylulose 5-phosphate reductoisomerase in a quaternary complex with a magnesium ion, NADPH and the antimalarial drug fosmidomycin*, Acta Cryst. F63, 466-470 (2007).

In some embodiments, the MEP complementation enhances conversion of DOXP and MEP pools to MEcPP, the substrate for IspG. See FIG. 1. Bottlenecks in the MEP pathway from dxs to ispF can be determined with regard to DOX, ME, and MEcPP levels, which can be detected extracellularly. Complementation and expression of MEP pathway enzymes can be balanced to move carbon flux to MEcPP intermediate, as determined by metabolite profiling. In some embodiments, the expression or activity of IspG and IspH is balanced with respect to the expression or activity of Dxr, Dxs, IspD, IspE and IspF to pull MEcPP metabolite to IPP and DMAPP precursors. MEcPP can be transported to the extracellular medium, and thus large MEcPP pools can result in lost MEP carbon.

Figure 9:
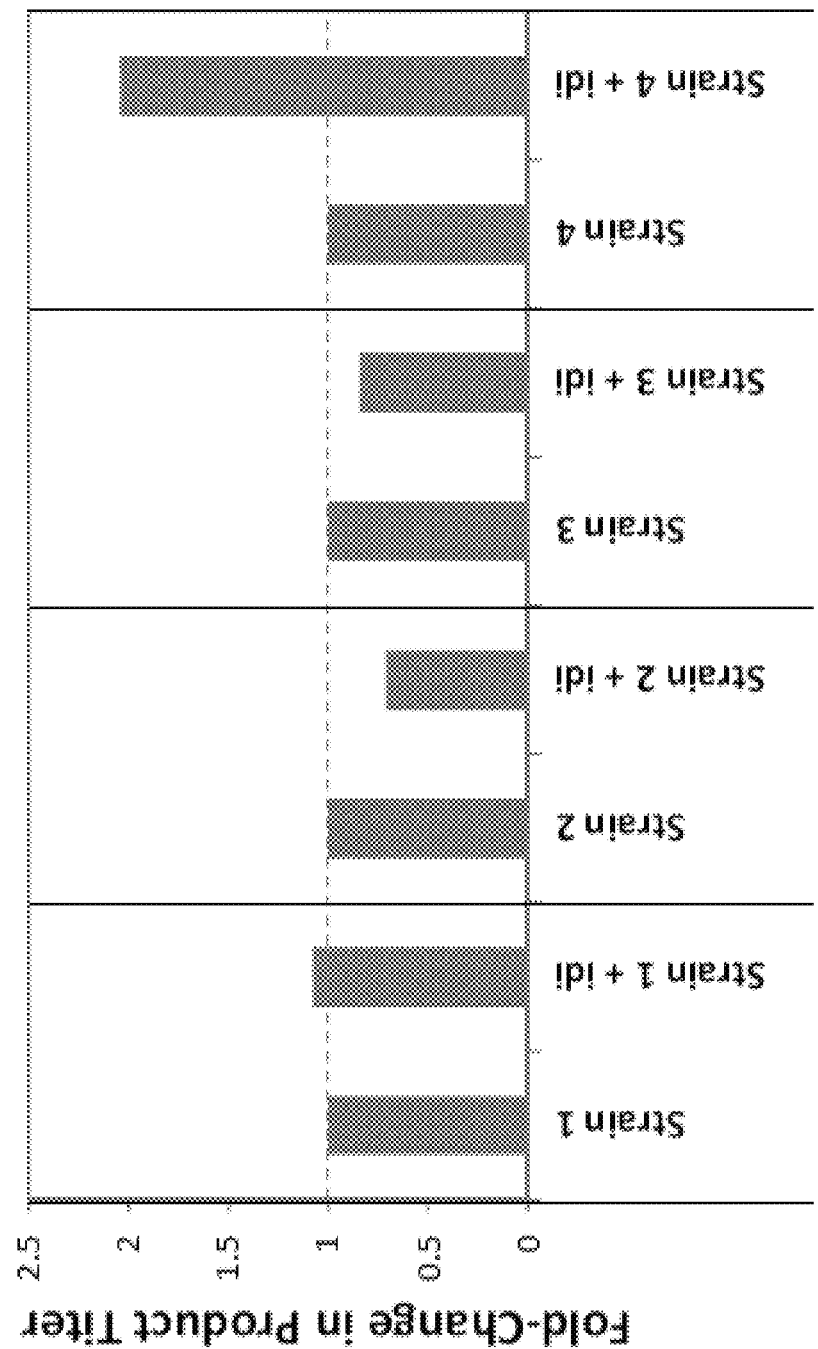
FIG. 9 shows that idi overexpression increases product titer in a strain that does not overexpress ispGH, and decreases titer in two strains that do overexpress ispGH, indicating that the balance between IPP and DMAPP controlled by Idi activity can be tuned up or down depending on the needs of the downstream pathway.

In some embodiments, the expression or activity of a recombinant idi gene is tuned to increase terpene or terpenoid production. The Idi enzyme catalyzes the reversible isomerization of IPP to DMAPP. Since every desired terpenoid product or undesired MEP side-product (e.g., UPP) uses one DMAPP and varying numbers of IPP, the ratio between the two precursors can have an impact on strain productivity. Varying the ratio of IPP:DMAPP available, e.g., by varying Idi expression or activity, can have an impact on the production of the desired terpenoid relative to other undesired products from the MEP pathway. For example, as shown in FIG. 9, while Idi overexpression slightly increases product titer in a strain that does not overexpress IspGH (Strain 1), it decreases titer in two strains that do (Strains 2 and 3), indicating that the balance between IPP and DMAPP controlled by Idi can be tuned up or down depending on the needs of the downstream pathway. However, Strain 4 (FIG. 9), which has a different balance of MEP pathway enzyme expression, more than doubles titer with Idi complementation. The expression of the recombinant idi gene can be tuned in various embodiments by modifying the promoter strength, gene copy number, position in an operon, or ribosome binding site, in addition to point mutations to increase or decrease enzyme productivity.

The microbial strain provides substantial increases in MEP carbon, including substantial increases in IPP and DMAPP precursor flux, without substantial impact on strain growth and viability, for example, as determined by optical density (O.D.) in culture, peak O.D., and/or growth rate. For example, despite increased flux through the MEP pathway, which is tightly controlled in bacterial cells, the microbial strain does not have a drop in peak O.D. of more than about 20%0, or in some embodiments, does not have a drop in peak O.D. of more than about 15%, or more than about 10%, or more than about 5%. In some embodiments, the strain does not exhibit a measurable impact on strain growth or viability, as determined for example by measuring growth rate or peak O.D.

In some embodiments, the bacterial strain contains one or more genetic modifications that enhance the supply and transfer of electrons through the MEP pathway, and/or to terpene or terpenoid products. In some embodiments, the enhanced supply and transfer of electrons through the MEP pathway is by recombinant expression of one or more oxidoreductase enzymes, including oxidoreductases that oxidize pyruvate and/or lead to reduction of ferredoxin. Ferredoxin supplies electrons to the MEP pathway and supports activity of IspG and IspH (which are Fe—S cluster enzymes). See FIG. 10. In various embodiments, the microbial strain comprises an overexpression of or complementation with one or more of a flavodoxin (fldA), flavodoxin reductase, ferredoxin (fdx), and ferredoxin reductase.

By way of example, in some embodiments, the oxidoreductase is a pyruvate:flavodoxin oxidoreductase (PFOR). In some embodiments, the PFOR is YdbK. In some embodiments, the YdbK is *E. coli* YdbK, or orthologs and derivatives thereof.

In some embodiments, the strain contains a complementation or overexpression of YdbK. YdbK is predicted to function as a pyruvate:flavodoxin oxidoreductase and/or pyruvate synthase. The oxidoreductase is thought to oxidize pyruvate to acetyl-CoA, reducing ferredoxin, which can then supply electrons to the MEP pathway, especially to support the strongly upregulated IspG and IspH enzymes that contain Fe—S clusters. In some embodiments, the expression of a recombinant YdbK is balanced with the expression of IspG and IspH, which can be determined by product titer (or farnesol titer as described below). In some embodiments, the YdbK gene is under the control of a weak or intermediate strength promoter. Additionally, extra electron-carrying or transferring cofactors can be expressed on top of YdbK overexpression. See, e.g., Akhtar, et al., *Metabolic Engineering*, 11(3): 139-147 (2009). In some experiments, YdbK is overexpressed with fdx (ferredoxin) from *Clostridium pasteurianum* (SEQ ID NO:10) and/or *E. Coli* (Ec.ydhY) (SEQ ID NO: 34), or enzyme having at least 80% or at least 90% sequence identity therewith. The bacterial strain may comprise a recombinant YdbK gene, which may be integrated into the chromosome or expressed from a plasmid. The amino acid sequence of the *E. coli* YdbK enzyme is shown herein as SEQ ID NO:9. In various embodiments, enzymes having structural or sequence homology, and comparable functionality, can be employed. For example, the amino acid sequence may have 50% or more sequence identity with any one of SEQ ID NO:9, or at least about 60%, sequence identity, or at least about 70% sequence identity, or at least about 80% sequence identity, or at least about 90% sequence identity, or at least about 95% sequence identity, or at least about 97% sequence identity, or at least about 98% sequence identity with the amino acid sequence of SEQ ID NO:9. In some embodiments, from 1 to about 10, or from 1 to about 5 amino acid substitutions, deletions, and/or insertions are made to the amino acid sequence (SEQ ID NO:9) to alter the activity of the protein.

In some embodiments, the strain comprises one or more P450 enzymes for the production of a terpenoid compound. The overexpression of YdbK and potentially other oxidoreductases, might support higher levels of P450 oxidative chemistry.

In some embodiments, including in embodiments where the bacterial strain overexpresses or has higher activity of pyruvate:flavodoxin oxidoreductase (PFOR), the strain exhibits reduced conversion of pyruvate to acetyl-COA by pyruvate dehydrogenase (PDH). In some embodiments, the conversion of pyruvate to acetyl-COA by PDH is reduced by deleting or inactivating PDH, or by reducing expression or activity of PDH. In some embodiments, PDH is deleted. Alternatively, activity of PDH may be reduced by one or more amino acid modifications. An exemplary mutation to reduce PDH activity is a G267C mutation in aceE.

In some embodiments, the conversion of pyruvate to acetyl-COA by PDH is reduced by modifying the aceE-aceF-lpd complex of PDH. In some embodiments, the aceE-aceF-lpd complex is modified by the deletion, inactivation, or reduced expression or activity of aceE, aceF, lpd, or a combination thereof. By way of example, in some embodiments, aceE is deleted (e.g., by knockout). Alternatively, in some embodiments, the aceE-aceF-lpd complex is modified by one or more mutations of aceE, aceF, lpd, or a combination thereof.

Figure 15:
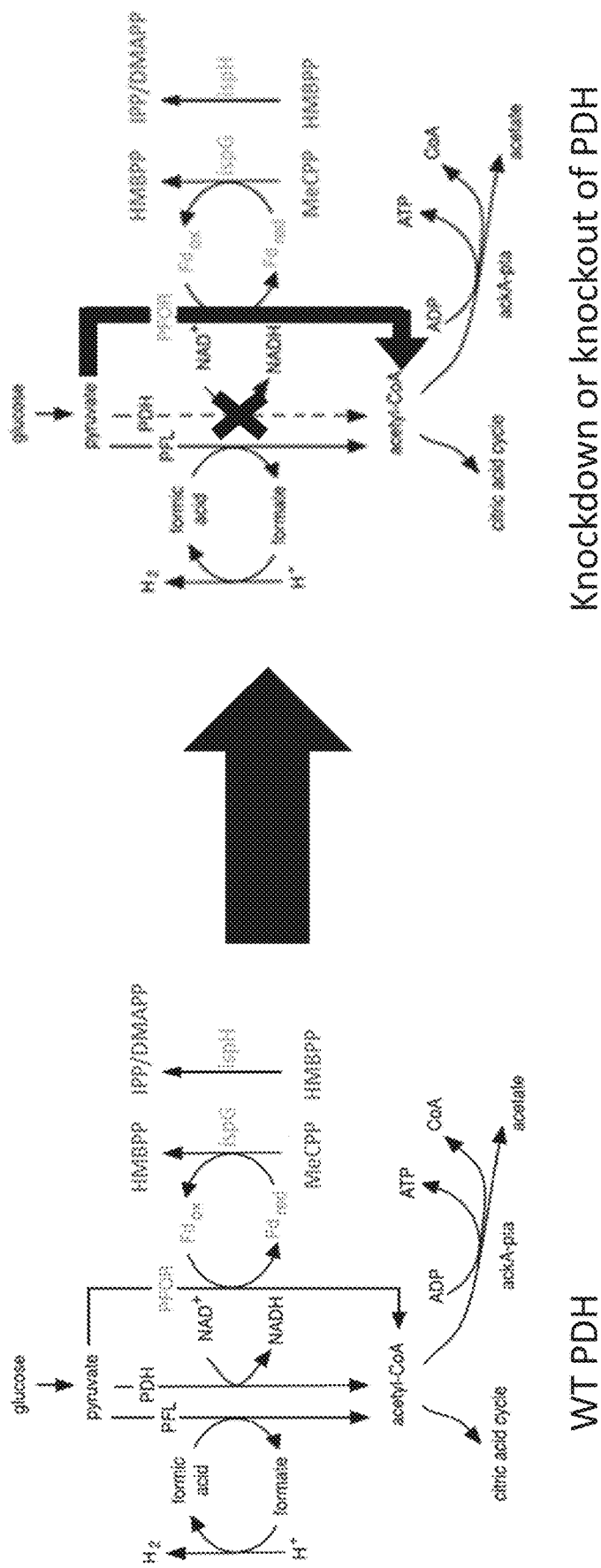
FIG. 15 is a diagram illustrating the three known reactions in *E. coli* to convert pyruvate (PYR) to acetyl-CoA (AcCoA) and illustrates how reducing or eliminating PDH mediated conversion of PYR to AcCoA results in the increase of PFOR-mediated conversion of PYR to AcCoA.

By reducing conversion of pyruvate to acetyl-COA by PDH, the bacterial strain will rely more on PFOR (e.g., YdbK) for the conversion of pyruvate to acetyl-COA. See FIG. 15. This reliance enhances IspG and IspH activity.

In some embodiments, supply and transfer of electrons to IspG and IspH is improved by overexpression or complementation with one or more oxidoreductases, such as, e.g., PFOR. By way of example, in some embodiments, the PFOR, or a homolog thereof, is selected from YdbK (SEQ ID NO: 9), Scy.pfor (*Synechocystis* sp.) (SEQ ID NO: 29), Ki.pfor (*Kluyvera intermedia*) (SEQ ID NO: 30), Da.pfor (*Desulfovibrio africanus*) (SEQ ID NO: 31), Ns.pfor (*Nostoc* sp.) (SEQ ID NO: 32), Ec.ydhV (*E. Coli*) (SEQ ID NO: 33), Ga.pfor (*Gilliamella apicola*) (SEQ ID NO: 35), and Sco.pfor (*Synechococcus* sp.). In some embodiments, the PFOR is YdbK.

In some embodiments, the PFOR comprise a sequence that is at least 60% identical to any one of SEQ ID NOs. 29-35. For example, the PFOR can comprise a sequence that is at least about 60%, at least about 70%, at least about 80%, at least about 90%, at least about 95%, at least about 97%, at least about 98%, at least about 99%, or 100% identical to any of one of SEQ ID NOs. 29-35.

In some embodiments, the overexpression or complementation with PFOR such as, e.g., YdbK, can result in improved performance through expression of electron carriers having a redox potential of about 400 to 550 mV, or in some embodiments, in the range of about 400 to 500 mV, or in the range of about 400 to 475 mV. In some embodiment, the electron carrier is ferrodoxin, flavodoxin, or NADPH. By way of example, in some embodiments, the electron carrier is Cv.fdx (*Allochromatinum vinosum*).

In some embodiments, the bacterial strain has overexpression or complementation with one or more fpr homologs. By way of example, in some embodiments, the fpr homolog is selected from Ns.fpr (*Nostoc* sp.) (SEQ ID NO: 36), Sco.fpr (*Synechococcus* sp.) (SEQ ID NO: 37), and Ec.fpr (*E. Coli*) (SEQ ID NO: 38).

In some embodiments, the fpr comprise a sequence that is at least 60% identical to any one of SEQ ID NOs. 36-38. For example, the fpr can comprise a sequence that is at least about 60%, at least about 70, at least about 80%, at least about 90%, at least about 95%, at least about 97%, at least about 98%, at least about 99%, or 100% identical to any of one of SEQ ID NOs: 36-38.

In some embodiments, the bacterial strain overexpressing YdbK or homolog or derivative thereof, further expresses a non-native electron acceptor/donor, such as one or more non-native fdx and/or fldA homologs. By way of example, the fdx homolog may be selected from Hm.fdx1 (*Heliobacterium modesticaldum*) (SEQ ID NO: 15), Pa.fdx (*Pseudomonas aeruginosa*) (SEQ ID NO: 16), Cv.fdx (*Allochromatium vinosum*) (SEQ ID NO: 17), Cv.fdx_C57A (synthetic) (SEQ ID NO: 18), Ec.yfhL (*E. Coli*) (SEQ ID NO: 19), Ca.fdx (*Clostridium acetobutylicum*) (SEQ ID NO: 20), Cp.fdx (*Clostridium pasteurianum*) (SEQ ID NO: 10), Ec.fdx (*E. Coli*) (SEQ ID NO: 21), Ev2.fdx (*Ectothiorhodospira shaposhnikovii*) (SEQ ID NO: 22), Pp1.fdx (*Pseudomonas putida*) (SEQ ID NO: 23), and Pp2.fdx (*Pseudomonas putida*) (SEQ ID NO: 24). In some embodiments, the fldA homolog includes one or more selected from Ec.fldA (*E. coli*) (SEQ ID NO: 27), Ac.fldA2 (*Azotobacter chroococcum*) (SEQ ID NO: 26), Av.fldA2 (*Azotobacter vinelandii*) (SEQ ID NO: 25), and Bs.fldA (*B. subtilis*) (SEQ ID NO: 28). Expression of a non-native fdx homolog and/or fldA homolog results in an increased supply of electrons to IspG and/or IspH, an increase in IspG/H activity, and an increase in terpenoid production. See FIGS. 19A-C.

In some embodiments, the non-native fdx homologs comprise a sequence that is at least 60% identical to any one of SEQ ID NOs. 10 and 15-24. For example, the non-native fdx homologs can comprise a sequence that is at least about 60%, at least about 70%, at least about 80%, at least about 90%, at least about 95%, at least about 97%, at least about 98%, at least about 99%, or 100% identical to any of one of SEQ ID NOs. 10 and 15-24.

In some embodiments, the non-native fldA homologs comprise a sequence that is at least 60% identical to any one of SEQ ID NOs. 25-28. For example, the non-native fldA homologs can comprise a sequence that is at least about 60%, at least about 70%, at least about 80%, at least about 90%, at least about 95%, at least about 97%, at least about 98%, at least about 99%, or 100% identical to any of one of SEQ ID NOs. 25-28.

In some embodiments, the bacterial strain has overexpression or complementation with one or more PFOR and/or fpr and, optionally, one or more of a flavodoxin (fldA), flavodoxin reductase, ferredoxin (fdx), and ferredoxin reductase. By way of example, in some embodiments the bacterial strain includes Ec.ydhV (*E. Coli*) (SEQ ID NO: 33) and Ec.ydhY (*E. Coli*) (SEQ ID NO: 34); Ec.ydbK (*E. Coli*) (SEQ ID NO: 9) and Cp.fdx (*Clostridium pasteurianum*) (SEQ ID NO: 10); Ec.fpr (*E. Coli*) (SEQ ID NO: 38) and Ec.fdx (*E. Coli*) (SEQ ID NO: 21); or Ec.fpr (*E. Coli*) (SEQ ID NO: 38) and Ec.fldA (*E. coli*) (SEQ ID NO: 27).

In other aspects, the invention provides bacterial strains that overexpress PgpB or NudB enzymes, for increasing MEP carbon pull. Installing this alternate 'product' pull by overexpressing genes such as pgpB and nudB pulls even more flux through the MEP pathway (though to non-target products) and minimizes the accumulation of potentially toxic or feedback inhibitory intermediates (e.g., IPP, DMAPP, FPP). In some embodiments, the PgpB or NudB overexpression is in the absence of a downstream terpenoid pathway, thereby creating a 'universal chassis'; that is, a strain that can have any terpenoid downstream transformed into it and be quickly optimized for commercial production.

More specifically, carbon can be pulled through the MEP pathway to create alternate products that will pool outside the cell. PgpB dephosphorylates FPP to farnesol (FOH), and NudB dephosphorylates IPP and DMAPP to isoprenol (3-methyl-3-buten-1-ol) and prenol (3-methyl-2-buten-1-ol), respectively (See FIG. 1). Enhancing transport of these products outside the cell prevents buildup of IPP, DMAPP, and FPP; which like HMBPP, can feedback and exert control on the MEP pathway. IPP inhibits growth and feedback inhibits Dxs. See Cordoba, Salmi & Leon (2009) *J. Exp. Bot.* 60, 10, 2933-2943. FPP inhibits growth and feedback inhibits ispF-MEP complex, which itself is formed when MEP binds and enhances IspF activity in a feed-forward manner. Bitok & Meyers (2012) *ACS Chem. Biol.* 2012, 7, 1702-1710. Farnesol, isoprenol, and prenol accumulate outside the cell and, like the intermediates in the MEP pathway, can be used to track carbon flux through the MEP pathway via LC/MS or GC/MS quantitation.

In various embodiments, enzymes having structural or sequence homology, and comparable functionality, can be employed. For example, the amino acid sequence may have 50% or more sequence identity with either SEQ ID NOS: 11 (PgpB) or 12 (NudB), or at least about 60% sequence identity, or at least about 70% sequence identity, or at least about 80% sequence identity, or at least about 90% sequence identity, or at least about 95% sequence identity with the amino acid sequence of SEQ ID NO: 1 or 12. In some embodiments, from 1 to about 10, or from 1 to about 5 amino acid substitutions, deletions, and/or insertions are made to the amino acid sequence (SEQ ID NO: 11 or 12) to alter the activity of the protein, including substitutions to one or more of the substrate binding site or active site.

Figure 7:
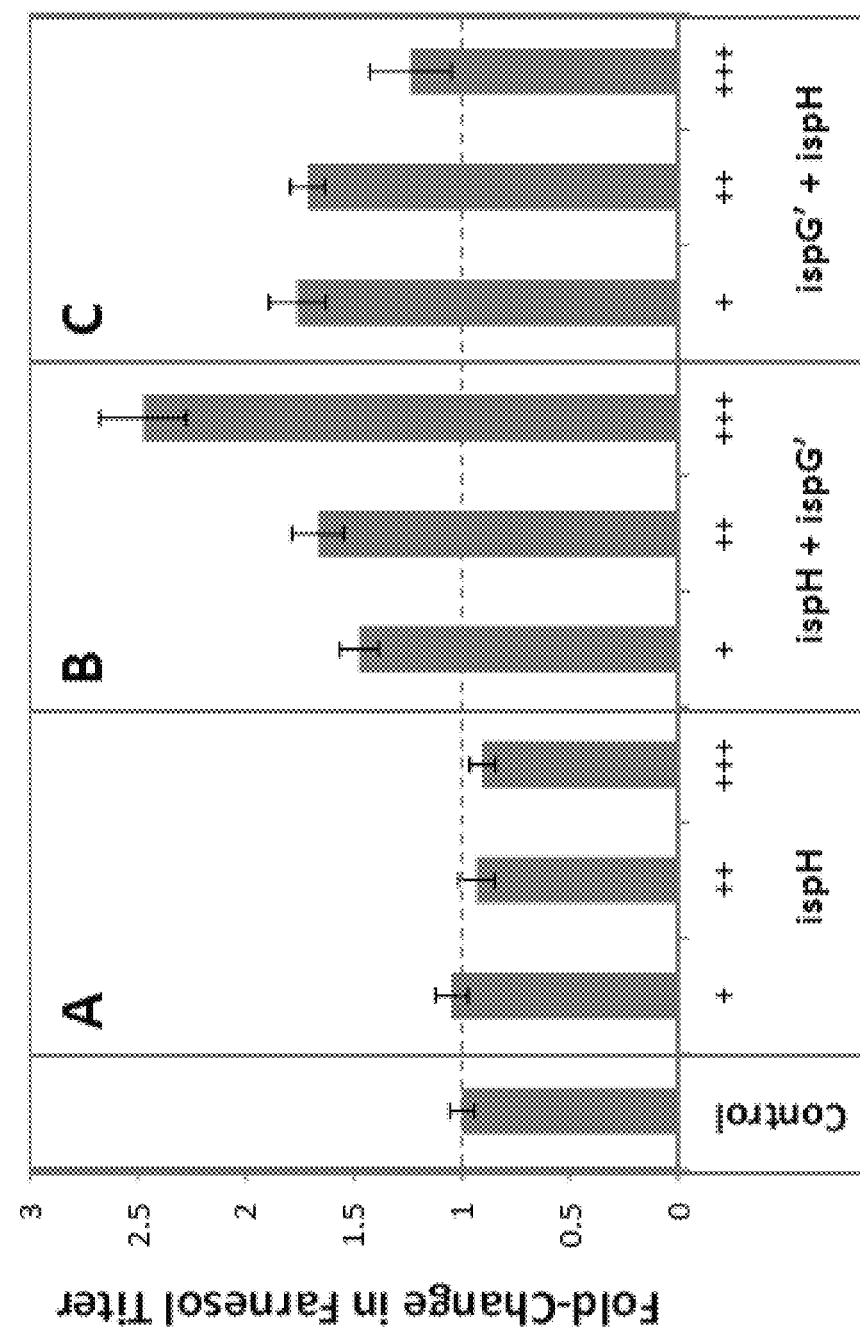
FIG. 7 shows that increasing and tuning expression of ispG' and/or ispH in a strain that produces farnesol can improve product titer. The control strain has additional copies of dxs, dxr, ispD, ispF, ispE, ispG, ispH, and idi, as well as additional copies of ydbK and pgpB. Additional copies of ispH and/or ispG' are integrated into the strains under increasing promoter strength (+, ++, +++).
Figure 8:
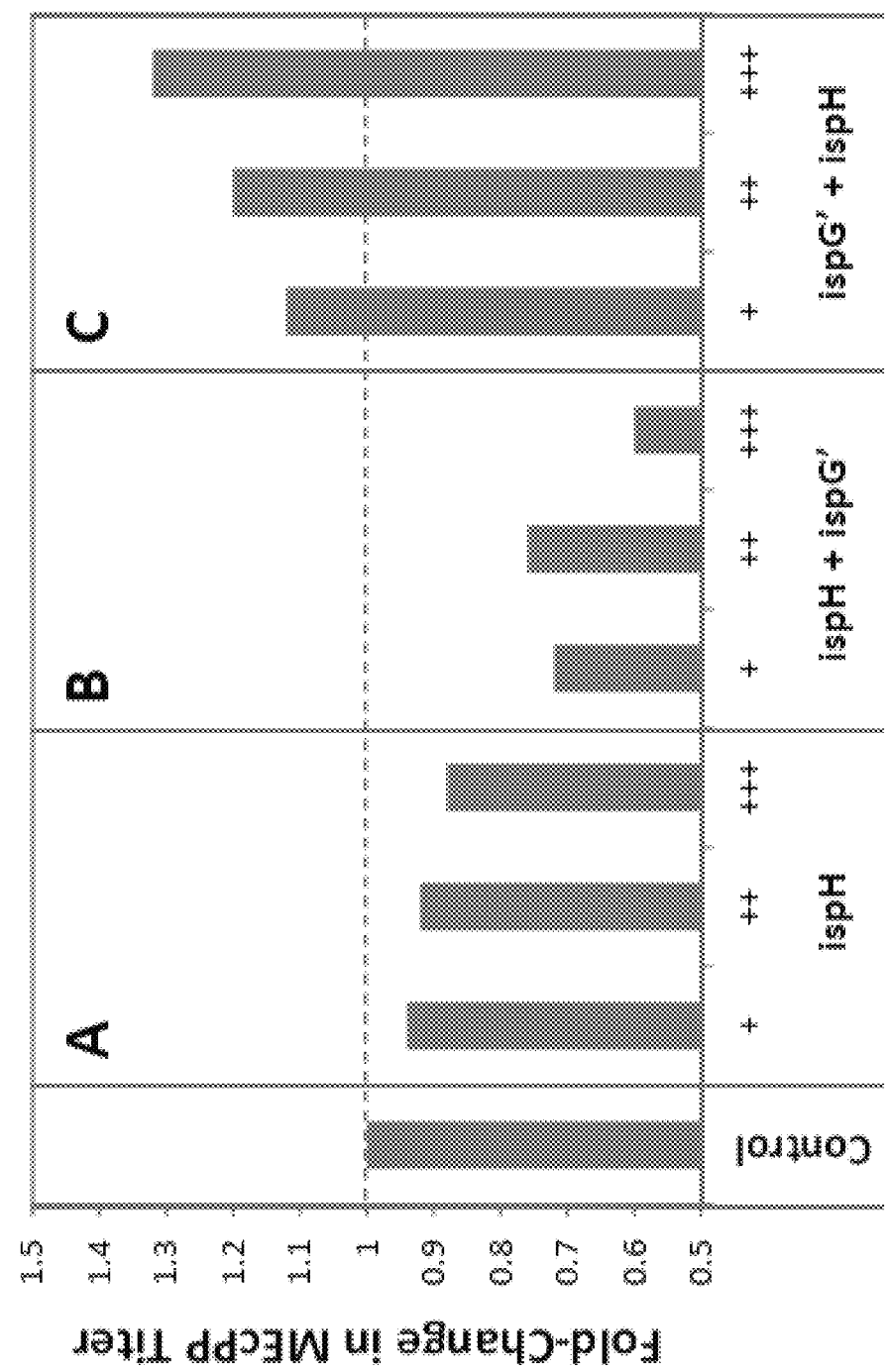
FIG. 8 shows that increase in farnesol product titer (shown in FIG. 7) is accompanied by a decrease in MEcPP pool size, and depends on the ratio of ispG and ispH.

Thus, by constitutively expressing an additional copy of pgpB or nudB, carbon flux through the MEP pathway can be improved, and a slow growth phenotype ameliorated. In cases where ispG and ispH are balanced and pgpB or nudB are overexpressed, the increase or decrease in farnesol product is inversely correlated with MEcPP level (FIGS. 7 and 8).

However, too much PgpB or NudB expression might negatively impact the total flux through to farnesol, with lower titer and smaller fold-change. See FIG. 6. Thus, in various embodiments, the expression of the recombinant PgpB and/or NudB is tuned to provide higher terpene or terpenoid product titer, optionally by varying promoter strength, gene copy number, position in an operon, and/or ribosome binding site. In some embodiments, the recombinant pgpB and/or nudB genes are expressed under control of a weak or intermediate strength promoter. The recombinant pgpB or nudB can be integrated into the chromosome or expressed from a plasmid.

In some embodiments, the bacterial strains overexpress one or more synthases for increasing MEP carbon pull. By way of example, in some embodiments, the synthase is selected from *Artemisia annua* farnesene synthase and valencene synthase.

Figure 14:
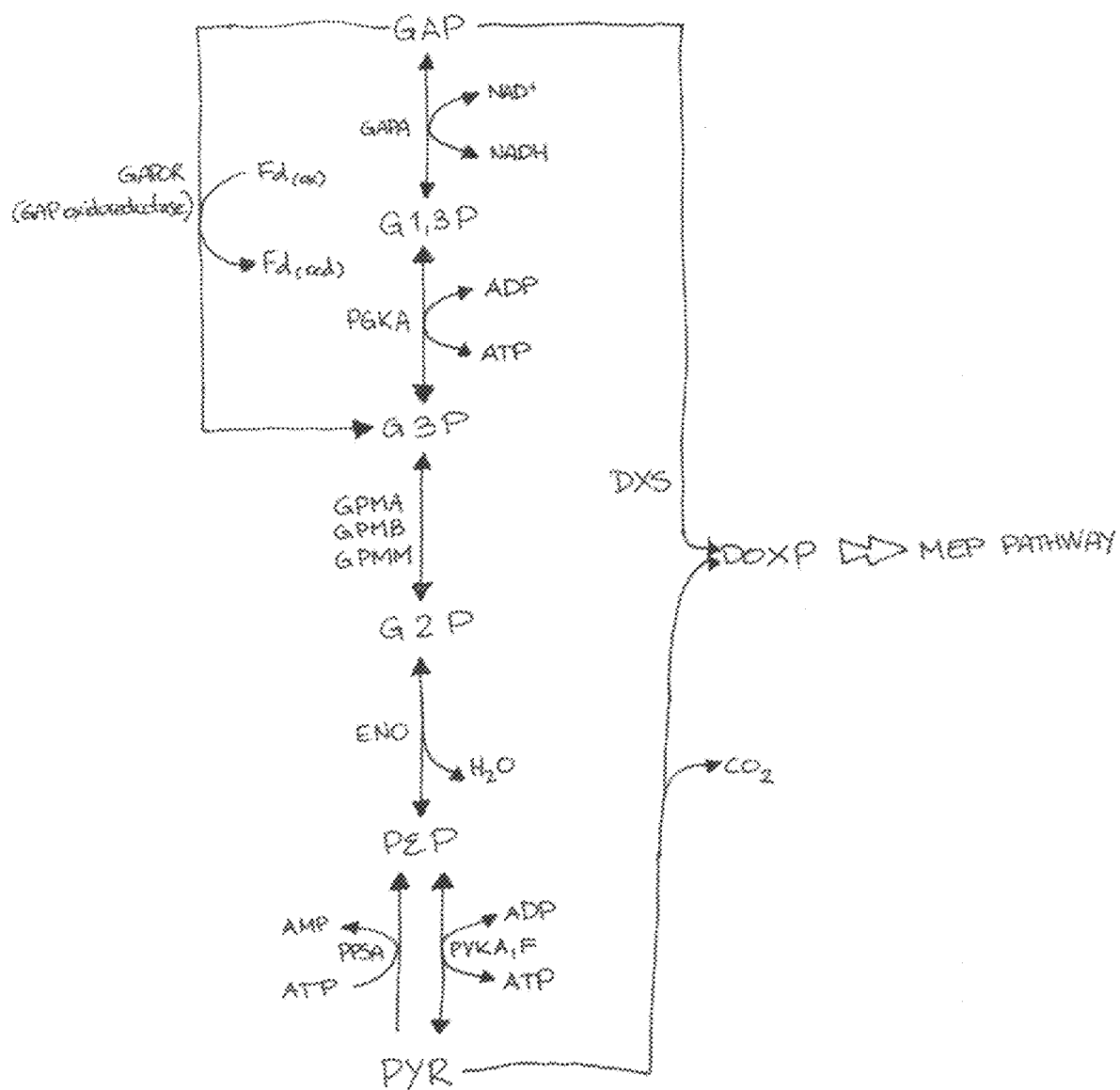
FIG. 14 illustrates the interface between glycolysis and the MEP pathway, and illustrates opportunities to tune co-factor availability by altering expression of oxidoreductase enzymes.

In some embodiments, the bacterial strain has one or more additional modifications to increase co-factor availability or turnover, including NADH and NADPH cofactor, thereby leading to increases in MEP carbon. See FIG. 14. In some embodiments, the bacterial strain expresses a glyceraldehyde 3-phosphate ferredoxin oxidoreductase (GAPOR), for example, from *Methanococcus maripaludis* (SEQ ID NO: 14) or other mesophilic organism. Expression of a GAPOR would provide electrons to ferredoxins in central carbon metabolism, and could provide electrons for IspG, IspH or P450 enzymes. In some embodiments, the bacterial strain overexpresses one or more genes of the ydh operon, such as ydhV or ydhY (e.g., by complementing the wild-type gene or enhancing expression of the endogenous bacterial gene). YdhV or other bacterial genes having GAPOR-like activity can increase co-factor availability to further enhance MEP carbon. Other genetic modifications include downregulation, inactivation, or deletion of gshA or expression of CHAC1 and/or CHAC2 (e.g., from *Homo sapiens*). These modifications can alter glutathione levels, thereby indirectly increasing NADPH availability.

While various bacterial species can be modified in accordance with the disclosure, in some embodiments, the bacterial strain is a bacteria selected from *Escherichia* spp., *Bacillus* spp., *Corynebacterium* spp., *Rhodobacter* spp., *Zymomonas* spp., *Vibrio* spp., and *Pseudomonas* spp. In some embodiments, the bacterial strain is a species selected from *Escherichia coli, Bacillus subtilis, Corynebacterium glutamicum, Rhodobacter capsulatus, Rhodobacter sphaeroides, Zymomonas mobilis, Vibrio natriegens,* or *Pseudomonas putida.* In some embodiments, the bacterial strain is *E. coli*.

In accordance with embodiments described herein, various strategies can be employed for engineering the expression or activity of recombinant genes and enzymes, including, for example, modifications or replacement of promoters of different strengths, modifications to the ribosome binding sequence, modifications to the order of genes in an operon or module, gene codon usage, RNA or protein stability, RNA secondary structure, and gene copy number, among others.

In some embodiments, the ribosome binding site sequence can be altered, to tune translation of the mRNA. The Shine-Dalgarno (SD) sequence is the ribosomal binding site in bacteria and is generally located around 8 bases upstream of the start codon AUG. The RNA sequence helps recruit the ribosome to the messenger RNA (mRNA) to initiate protein synthesis by aligning the ribosome with the start codon. The six-base consensus sequence is AGGAGG (SEQ ID NO: 13) in *Escherichia coli*. Mutations in the consensus sequence can be screened for improvements in product titer (including farnesol titer in some embodiments), or screened by metabolomic analysis of MEP carbon.

For complementation of genes, wild type genes can be employed, and in some embodiments, the gene is a wild-type *E. coli* gene. Alternatively, various orthologs can be employed, which may show nucleotide or amino acid homology to the *E. coli* gene. Exemplary genes can be derived from the orthologs of *Bacillus* spp., *Corynebacterium* spp., *Rhodobacter* spp., *Zymomonas* spp., *Vibrio* spp., *Pseudomonas* spp., *Chloroboculum* spp., *Synechocystis* sp., *Burkholderia* spp., and *Stevia rebaudiana*, for example.

The similarity of nucleotide and amino acid sequences, i.e. the percentage of sequence identity, can be determined via sequence alignments. Such alignments can be carried out with several art-known algorithms, such as with the mathematical algorithm of Karlin and Altschul (Karlin & Altschul (1993) *Proc. Natl. Acad. Sci. USA* 90: 5873-5877), with hmmalign (HMMER package, http://hmmer.wustl.edu/) or with the CLUSTAL algorithm (Thompson, J. D., Higgins, D. G. & Gibson, T. J. (1994) *Nucleic Acids Res.* 22, 4673-80). The grade of sequence identity (sequence matching) may be calculated using e.g. BLAST, BLAT or BlastZ (or BlastX). A similar algorithm is incorporated into the BLASTN and BLASTP programs of Altschul et al (1990) *J. Mol. Biol.* 215: 403-410. BLAST polynucleotide searches can be performed with the BLASTN program, score=100, word length=12.

BLAST protein searches may be performed with the BLASTP program, score=50, word length=3. To obtain gapped alignments for comparative purposes, Gapped BLAST is utilized as described in Altschul et al (1997) *Nucleic Acids Res.* 25: 3389-3402. When utilizing BLAST and Gapped BLAST programs, the default parameters of the respective programs are used. Sequence matching analysis may be supplemented by established homology mapping techniques like Shuffle-LAGAN (Brudno M., *Bioinformatics* 2003b, 19 Suppl 1:154-162) or Markov random fields.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups:

(1) hydrophobic: Met, Ala, Val, Leu, Ile;
(2) neutral hydrophilic: Cys, Ser, Thr; Asn, Gin;
(3) acidic: Asp, Glu;
(4) basic: His, Lys, Arg;
(5) residues that influence chain orientation: Gly, Pro; and
(6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. Some preferred conservative substitutions within the above six groups are exchanges within the following sub-groups: (i) Ala, Val, Leu and Ile; (ii) Ser and Thr; (ii) Asn and Gin; (iv) Lys and Arg; and (v) Tyr and Phe.

As used herein, "non-conservative substitutions" are defined as exchanges of an amino acid by another amino acid listed in a different group of the six standard amino acid groups (1) to (6) shown above.

Modifications of enzymes as described herein can include conservative and/or non-conservative mutations.

In some embodiments "rational design" is involved in constructing specific mutations in enzymes. Rational design refers to incorporating knowledge of the enzyme, or related enzymes, such as its reaction thermodynamics and kinetics, its three dimensional structure, its active site(s), its substrate(s) and/or the interaction between the enzyme and substrate, into the design of the specific mutation. Based on a rational design approach, mutations can be created in an enzyme which can then be screened for increased production of a terpene or terpenoid relative to parent strain levels, or metabolite profile that corresponds with improvements in MEP carbon. In some embodiments, mutations can be rationally designed based on homology modeling. "Homology modeling" refers to the process of constructing an atomic resolution model of a protein from its amino acid sequence, using the three-dimensional structure of a related homologous protein.

Amino acid modifications can be made to enzymes to increase or decrease activity of the enzyme or enzyme complex. Gene mutations can be performed using any genetic mutation method known in the art. In some embodiment, a gene knockout eliminates a gene product in whole or in part. Gene knockouts can be performed using any knockout method known in the art.

Manipulation of the expression of genes and/or proteins, including gene modules, can be achieved through various methods. For example, expression of the genes or operons can be regulated through selection of promoters, such as inducible or constitutive promoters, with different strengths (e.g., strong, intermediate, or weak). Several non-limiting examples of promoters include Trc, T5 and T7. Additionally, expression of genes or operons can be regulated through manipulation of the copy number of the gene or operon in the cell. In some embodiments, expression of genes or operons can be regulated through manipulating the order of the genes within a module, where the genes transcribed first are generally expressed at a higher level. In some embodiments, expression of genes or operons is regulated through integration of one or more genes or operons into the chromosome.

In some embodiments, balancing gene expression includes the selection of high-copy number plasmids, or single-, low- or medium-copy number plasmids. In still other embodiments, the step of transcription termination can also be targeted for regulation of gene expression, through the introduction or elimination of structures such as stem-loops.

Expression vectors containing all the necessary elements for expression are commercially available and known to those skilled in the art. See, e.g., Sambrook et al., Molecular Cloning: A Laboratory Manual, Second Edition, Cold Spring Harbor Laboratory Press, 1989. Cells are genetically engineered by the introduction into the cells of heterologous DNA. The heterologous DNA is placed under operable control of transcriptional elements to permit the expression of the heterologous DNA in the host cell.

In some embodiments, endogenous genes are edited, as opposed to gene complementation. Editing can modify endogenous promoters, ribosomal binding sequences, or other expression control sequences, and/or in some embodiments modifies trans-acting and/or cis-acting factors in gene regulation. Genome editing can take place using CRISPR/Cas genome editing techniques, or similar techniques employing zinc finger nucleases and TALENs. In some embodiments, the endogenous genes are replaced by homologous recombination.

In some embodiments, genes are overexpressed at least in part by controlling gene copy number. While gene copy number can be conveniently controlled using plasmids with varying copy number, gene duplication and chromosomal integration can also be employed. For example, a process for genetically stable tandem gene duplication is described in US 2011/0236927, which is hereby incorporated by reference in its entirety.

In certain embodiments, the bacterial cell produces one or more terpene or terpenoid compounds. A terpenoid, also referred to as an isoprenoid, is an organic chemical derived from a five-carbon isoprene unit (C5). Several non-limiting examples of terpenoids, classified based on the number of isoprene units that they contain, include: hemiterpenoids (1 isoprene unit), monoterpenoids (2 isoprene units), sesquiterpenoids (3 isoprene units), diterpenoids (4 isoprene units), sesterterpenoids (5 isoprene units), triterpenoids (6 isoprene units), tetraterpenoids (8 isoprene units), and polyterpenoids with a larger number of isoprene units. In an embodiment, the bacterial host cell produces a terpenoid selected from a monoterpenoid, a sesquiterpenoid, diterpenoid, a sesterpenoid, or a triterpenoid. Terpenoids represent a diverse class of molecules that provide numerous commercial applications, including in the food and beverage industries as well as the perfume, cosmetic and health care industries. By way of example, terpenoid compounds find use in perfumery (e.g. patchoulol), in the flavor industry (e.g., nootkatone), as sweeteners (e.g., steviol), colorants, or therapeutic agents (e.g., taxol) and many are conventionally extracted from plants. Nevertheless, terpenoid molecules are found in ppm levels in nature, and therefore require massive harvesting to obtain sufficient amounts for commercial applications.

The bacterial cell will generally contain a recombinant downstream pathway that produces the terpenoid from IPP and DMAPP precursors. Terpenes such as Monoterpenes (C10), Sesquiterpenes (C15), Diterpenes (C20), Sesterterpenes (C25), and Triterpenes (C30) are derived from the prenyl diphosphate substrates, geranyl diphosphate (GPP), farnesyl diphosphate (FPP) geranylgeranyl diphosphate (GGPP), geranylfarnesyl diphosphate (FGPP), and two FPP, respectively, through the action of a very large group of enzymes called the terpene (terpenoid) synthases. These enzymes are often referred to as terpene cyclases since the product of the reactions are cyclized to various monoterpene, sesquiterpene, diterpene, sesterterpene and triterpene carbon skeleton products. Many of the resulting carbon skeletons undergo subsequence oxygenation by cytochrome P450 enzymes to give rise to large families of derivatives.

Exemplary terpene or terpenoid products that may be produced in accordance with the invention are described in U.S. Pat. No. 8,927,241, which is hereby incorporated by reference, and include: farnesene, amorphadiene, artemisinic acid, artemisinin, bisabolol, bisabolene, alpha-Sinensal, beta-Thujone, Camphor, Carveol, Carvone, Cineole, Citral, Citronellal, Cubebol, Geraniol, Limonene, Menthol, Menthone, Myrcene, Nootkatone, Nootkatol, Patchouli, Piperitone, Rose oxide, Sabinene, Steviol, Steviol glycoside (including Rebaudioside D or Rebaudioside M), Taxadiene, Thymol, and Valencene. Enzymes for recombinantly constructing the pathways in E. coli are described in U.S. Pat. No. 8,927,241, WO 2016/073740, and WO 2016/029153, which are hereby incorporated by reference.

Exemplary P450 enzymes that are operative on sesquiterpene scaffolds to produce oxygenated terpenoids are described in WO 2016/029153, which is hereby incorporated by reference. In addition, P450 reductase proteins that find use in the bacterial strains described herein are described in WO 2016/029153 as well as WO 2016/073740.

As used herein, the term "oxygenated terpenoid" refers to a terpene scaffold having one or more oxygenation events, producing a corresponding alcohol, aldehyde, carboxylic acid and/or ketone. In some embodiments, the bacterial cell produces at least one terpenoid selected from Abietadiene, Abietic Acid, alpha-Sinensal, beta-Thujone, Camphor, Carveol, Carvone, Celastrol, Ceroplastol, Cineole, Citral, Citronellal, Cubebol, Cucurbitane, Forskolin, Gascardic Acid, Geraniol, Haslene, Levopimaric Acid, Limonene, Lupeol, Menthol, Menthone, Mogroside, Nootkatone, Nootkatol, Ophiobolin A, Patchouli, Piperitone, Rebaudioside D, Rebaudioside M, Sabinene, Steviol, Steviol glycoside, Taxadiene, Thymol, and Ursolic Acid.

In some embodiments, the terpenoid synthase enzyme is upgraded to enhance the kinetics, stability, product profile, and/or temperature tolerance of the enzyme, as disclosed, for example, in WO 2016/029153 and WO 2016/073740, which are hereby incorporated by reference.

In another embodiment, the bacterial cell produces valencene and/or nootkatone. In such an embodiment, the bacterial cell may express a biosynthetic pathway that further includes a farnesyl diphosphate synthase, a Valencene Synthase, and a Valencene Oxidase. Farnesyl diphosphate synthases (FPPS) produce farnesyl diphosphates from isopentenyl diphosphate (IPP) and dimethylallyl diphosphate (DMAPP). An exemplary farnesyl diphosphate synthase is ERG20 of Saccharomyces cerevisiae (NCBI accession P08524) and E. coli ispA. Valencene synthase produces sesquiterpene scaffolds and are described in, for example, US 2012/0107893, US 2012/0246767, and U.S. Pat. No. 7,273,735, which are hereby incorporated by reference in their entireties. Genes and host cells for the production of terpenoid product comprising valencene and/or nootkatone are described in WO 2016/029153, which is hereby incorporated by reference.

In an embodiment, the bacterial cell produces steviol or steviol glycoside (e.g., RebD or RebM). Steviol is produced from kaurene by the action of two P450 enzymes, kaurene oxidase (KO) and kaurenoic acid hydroxylase (KAH). After production of steviol, various steviol glycoside products may be produced through a series of glycosylation reactions, which can take place in vitro or in vivo. Pathways and enzymes for production of steviol and steviol glycosides are disclosed in US 2013/0171328, US 2012/0107893, WO 2012/075030, WO 2014/122328, which are hereby incorporated by reference in their entireties. WO 2016/073740 further discloses enzymes and bacterial host cells for production of RebM.

Other biosynthetic pathways for production of terpene or terpenoid compounds are disclosed in U.S. Pat. No. 8,927,241, which is hereby incorporated by reference in its entirety.

The bacterial strain may be cultured in batch culture, continuous culture, or semi-continuous culture. In some embodiments, the bacterial strain is cultured using a fed-batch process comprising a first phase where bacterial biomass is created, followed by a terpene or terpenoid production phase. Fed-batch culture is a process where nutrients are fed to the bioreactor during cultivation and in which the product(s) remain in the bioreactor until the end of the run. Generally, a base medium supports initial cell culture and a feed medium is added to prevent nutrient depletion. The controlled addition of the nutrient directly affects the growth rate of the culture and helps to avoid overflow metabolism and formation of side metabolites.

An exemplary batch media for growing the bacterial strain (producing biomass) comprises, without limitation, yeast extract. In some embodiments, carbon substrates such C1, C2, C3, C4, C5, and/or C6 carbon substrates are fed to the culture for production of the terpene or terpenoid product. In exemplary embodiments, the carbon source is glucose, sucrose, fructose, xylose, and/or glycerol. Culture conditions are generally selected from aerobic, microaerobic, and anaerobic.

In some embodiments, the culture is maintained under aerobic conditions, or microaerobic conditions. For example, when using a fed-batch process, the biomass production phase can take place under aerobic conditions, followed by reducing the oxygen levels for the product production phase. For example, the culture can be shifted to microaerobic conditions after from about 10 to about 20 hours. In this context, the term "microaerobic conditions" means that cultures are maintained just below detectable dissolved oxygen. See, Partridge J D, et al., *Transition of Escherichia coli from Aerobic to Micro-aerobic Conditions Involves Fast and Slow Reacting Regulatory Components*, J. Biol. Chem. 282(15): 11230-11237 (2007).

The production phase includes feeding a nitrogen source and a carbon source. For example, the nitrogen source can comprise ammonium (e.g., ammonium hydroxide). The carbon source may contain C1, C2, C3, C4, C5, and/or C6 carbon sources, such as, in some embodiments, glucose, sucrose, or glycerol. The nitrogen and carbon feeding can be initiated when a predetermined amount of batch media is consumed, a process that provides for ease of scaling. In some embodiments, the nitrogen feed rate is from about 8 L per hour to about 20 L per hour, but will depend in-part on the product, strain, and scale.

In various embodiments, the bacterial host cell may be cultured at a temperature between 22° C. and 37° C. While commercial biosynthesis in bacteria such as E. coli can be limited by the temperature at which overexpressed and/or foreign enzymes are stable, recombinant enzymes (including the terpenoid synthase) may be engineered to allow for cultures to be maintained at higher temperatures, resulting in higher yields and higher overall productivity. In some embodiments, the culturing is conducted at about 22° C. or greater, about 23° C. or greater, about 24° C. or greater, about 25° C. or greater, about 26° C. or greater, about 27° C. or greater, about 28° C. or greater, about 29° C. or greater, about 30° C. or greater, about 31° C. or greater, about 32° C. or greater, about 33° C. or greater, about 34° C. or greater, about 35° C. or greater, about 36° C. or greater, or about 37° C. In some embodiments, the culture is maintained at a temperature of from 22 to 37° C., or a temperature of from 25 to 37° C., or a temperature of from 27 to 37° C., or a temperature of from 30 to 37° C.

In some embodiments, the bacterial strain is cultured at commercial scale. In some embodiments, the size of the culture is at least about 100 L, or at least about 200 L, or at least about 500 L, or at least about 1,000 L, or at least about 10,000 L, or at least about 100,000 L, or at least about 500,000 L. In some embodiments, the culture is from about 300 L to about 1,000,000 L.

In various embodiments, methods further include recovering the terpene or terpenoid product from the cell culture or from cell lysates. In some embodiments, the culture produces at least about 100 mg/L, at least about 150 mg/L, or at least about 200 mg/L, or at least about 500 mg/L, or at least about 1 g/L, or at least about 5 g/L, or at least about 10 g/L, or at least about 15 g/L of the terpene or terpenoid product.

In some embodiments, the production of indole is used as a surrogate marker for terpenoid production, and/or the accumulation of indole in the culture is controlled to increase production. For example, in various embodiments, accumulation of indole in the culture is controlled to below about 100 mg/L, or below about 75 mg/L, or below about 50 mg/L, or below about 25 mg/L, or below about 10 mg/L. The accumulation of indole can be controlled by balancing enzyme expression (and in particular, balancing the upstream and downstream pathways) and activity using the multivariate modular approach as described in U.S. Pat. No. 8,927,241 (which is hereby incorporated by reference). In some embodiments, the accumulation of indole is controlled by chemical means.

Other markers for efficient production of terpene and terpenoids, include accumulation of DOX or ME in the culture media. Generally, the bacterial strains described herein do not accumulate large amounts of these chemical species, which accumulate in the culture at less than about 5 g/L, or less than about 4 g/L, or less than about 3 g/L, or less than about 2 g/L, or less than about 1 g/L, or less than about 500 mg/L, or less than about 100 mg/L.

In some embodiments, MEcPP is the predominant MEP metabolite in the culture media, although its accumulation is limited by the genetic modifications to the bacterial strain, which pull MEP carbon downstream to IPP and DMAPP precursors. In various embodiments, MEcPP accumulates in the culture at less than about 30 g/L, or less than about 20 g/L, or less than about 2 g/L, or less than about 1 g/L, or less than about 500 mg/L, or less than about 100 mg/L.

The optimization of terpene or terpenoid production by manipulation of MEP pathway genes, as well as manipulation of the upstream and downstream pathways, is not expected to be a simple linear or additive process. Rather, through combinatorial analysis, optimization is achieved through balancing components of the MEP pathway, as well as upstream and downstream pathways. Indole accumulation (including prenylated indole) and MEP metabolite accumulation (e.g., DOX, ME, MEcPP, HMBPP, farnesol, prenol and isoprenol) in the culture or cells can be used as surrogate markers to guide this process.

The terpene or terpenoid product can be recovered by any suitable process. Generally, recovery includes separation of material comprising product from the culture or cells, followed by extraction and purification. For example recovery can include partitioning the desired product into an organic phase or hydrophobic phase. Alternatively, the aqueous phase can be recovered, or the whole cell biomass can be recovered, for further processing.

For example, in some embodiments, the product is a volatile terpene or terpenoid product. In such embodiments, the terpene or terpenoid product can be recovered from an organic or hydrophobic phase that is mechanically separated from the culture. Alternatively or in addition, the terpene or terpenoid product is harvested from the liquid and/or solid phase. In some embodiments, the product is purified by sequential extraction and purification. For example, the product may be purified by chromatography-based separation and recovery, such as supercritical fluid chromatography. The product may be purified by distillation, including simple distillation, steam distillation, fractional distillation, wipe-film distillation, or continuous distillation.

In some embodiments, the product is a non-volatile terpene or terpenoid product, which in some embodiments is an extracellular product recovered from the culture medium. Alternatively, the product is an intracellular product recovered from harvested cell material. Where the product is poorly soluble, it may be recovered by filtration, and optionally with solvent extraction (e.g., extraction with ethanol). Alternatively, or in addition, the product is recovered by chromatography-based separation, such as liquid chromatography. In some embodiments, the product is recovered by sequential extraction and purification. In still other embodiments, the product is crystallized out of solution.

The production of the desired product can be determined and/or quantified, for example, by gas chromatography (e.g., GC-MS). Production of product, recovery, and/or analysis of the product can be done as described in US 2012/0246767, which is hereby incorporated by reference in its entirety. For example, in some embodiments, product oil is extracted from aqueous reaction medium using an organic solvent, such as an alkane such as heptane or dodecane, followed by fractional distillation. In other embodiments, product oil is extracted from aqueous reaction medium using a hydrophobic phase, such as a vegetable oil, followed by organic solvent extraction and fractional distillation. Terpene and terpenoid components of fractions may be measured quantitatively by GC/MS, followed by blending of fractions to generate a desired product profile.

In various embodiments, the recovered terpene or terpenoid is incorporated into a product (e.g., a consumer or industrial product). For example, the product may be a flavor product, a fragrance product, a sweetener, a cosmetic, a cleaning product, a detergent or soap, or a pest control product. For example, in some embodiments, the product recovered comprises nootkatone, and the product is a flavor product selected from a beverage, a chewing gum, a candy, or a flavor additive, or the product is an insect repellant. In some embodiments, the oxygenated product is steviol or a steviol glycoside (e.g., RebM), which is provided as a sweetener, or is incorporated into ingredients, flavors, beverages or food products.

The invention further provides methods of making products such as foods, beverages, texturants (e.g., starches, fibers, gums, fats and fat mimetics, and emulsifiers), pharmaceutical products, tobacco products, nutraceutical products, oral hygiene products, and cosmetic products, by incorporating the terpene or terpenoids produced herein. The higher yields of such species produced in embodiments of the invention can provide significant cost advantages as well as sustainability.

In other aspects, the invention provides bacterial cells, such as *E. coli*, having one or more genetic modifications that increase products of IPP and DMAPP precursors. In various embodiments, the bacterial cells produce isopentenyl diphosphate (IPP) and dimethylallyl diphosphate (DMAPP) through the MEP pathway, and convert the IPP and DMAPP to a terpene or terpenoid product through a downstream synthesis pathway. The downstream synthesis pathway is generally a recombinant pathway, and may comprise a prenyl transferase, one or more terpene synthases, and optionally one or more P450 enzymes and P450 reductase enzymes (for example, each as described above). For example, the product may be a diterpene or diterpenoid, with the sequential action of a recombinant Type II diterpene synthase (DiTPS) on GGPP followed by a recombinant Type I DiTPS, or alternatively, a single recombinant synthase performs both steps.

Further, to improve MEP carbon available for product biosynthesis, the bacterial strain has one or more of the following genetic modifications:

(a) overexpression of IspG and IspH enzymes, the IspG and IspH enzymes having balanced expression to prevent accumulation of HMBPP intermediate, (b) a recombinant or modified gene encoding an enzyme that enhances supply and/or transfer of electrons through the MEP pathway and/or to terpene or terpenoid products, which is optionally an overexpression of a YdbK gene and optionally with a non-native fdx and/or fldA homolog, (c) an inactivation or deletion, or reduced expression or activity, of aceE or aceE enzyme complex, and optionally (d) a recombinant or modified idi gene to tune activity for higher terpene or terpenoid production.

Genes can be overepxressed by complementation with recombinant genes, or the endogenous genes can be modified to alter expression, as disclosed elsewhere herein.

The bacterial strain is a bacteria selected from *Escherichia* spp., *Bacillus* spp., *Corynebacterium* spp., *Rhodobacter* spp., *Zymomonas* spp., *Vibrio* spp., and *Pseudomonas* spp. For example, the bacterial strain is a species selected from *Escherichia coli, Bacillus subtilis, Corynebacterium glutamicum, Rhodobacter capsulatus, Rhodobacter sphaeroides, Zymomonas mobilis, Vibrio natriegens,* or *Pseudomonas putida*. In some embodiments, the bacterial strain is *E. coli*.

In various embodiments, upon culturing, HMBPP does not accumulate at more than about 10 mg/g DCW, or in some embodiments does not accumulate at more than about 8 mg/g of DCW, or in some embodiments does not accumulate at more than about 5 mg/g of DCW, or in some embodiments does not accumulate at more than about 4 mg/g DCW, or in some embodiments does not accumulate at more than about 2 mg/g DCW. In some embodiments, HMBPP does not accumulate at more than about 1 mg/g DCW, or does not accumulate at more than about 0.5 mg/g DCW, or more than about 0.2 mg/g DCW, or more than about 0.1 mg/g DCW.

In some embodiments, the bacterial strain expresses dxs, ispD, ispF, and idi as recombinant genes (e.g., as a complementation to wild-type MEP pathway enzymes), and which are optionally expressed as an operon. In some embodiments, the bacterial strain expresses dxs, dxr, ispD, ispE, ispF, and idi as recombinant genes, which are optionally expressed as 1, 2, or 3 individual operons. The recombinant genes of the MEP pathway are expressed from one or more plasmids or are integrated into the chromosome, and the expressions are balanced to improve MEP carbon flux. Specifically, the bacterial cell may produce MEcPP as the predominant MEP metabolite in the extracellular medium.

The recombinant IspG and IspH genes may comprise one or more beneficial mutations, or may be an IspG or ispH ortholog having improved properties or activity, as described herein. Further, in various embodiments, the expression of recombinant IspH is higher than the expression of the recombinant IspG, which can optionally be accomplished, at least in-part, by positioning ispH before ispG in an operon. Thus, the bacterial strain may express ispH and ispG from the same operon (with ispH positioned first), and under control of a strong promoter. The recombinant IspG and IspH genes are expressed from a plasmid or are integrated into the chromosome.

In some embodiments, the bacterial strain expresses a recombinant idi gene, which is tuned to increase product, optionally by modifying the promoter strength, gene copy number, position in an operon, or ribosome binding site.

In some embodiments, the bacterial strain expresses a recombinant YdbK gene, which is integrated into the chromosome or expressed from a plasmid. The bacterial strain may further comprise an overexpression of one or more of a flavodoxin, flavodoxin reductase, ferredoxin, and ferredoxin reductase, such as *Clostridium pasteurianum* ferredoxin (Cp.fdx). In some embodiments, the strain expresses one or more non-native fdx and/or fldA homologs. By way of example, the fdx homolog may be selected from Hm.fdx1 (*Heliobacterium modesticaldum*), Pa.fdx (*Pseudomonas aeruginosa*), Cv.fdx (*Allochromatium vinosum*), Ca.fdx (*Clostridium acetobutylicum*), Cp.fdx (*Clostridium pasteurianum*), Ev2.fdx (*Ectothiorhodospira shaposhnikovii*), Pp1.fdx (*Pseudomonas putida*) and Pp2.fdx (*Pseudomonas putida*). In some embodiments, the fldA homolog includes one or more selected from Ec.fldA (*E. coli*), Ac.fldA2 (*Azotobacter chroococcum*), Av.fldA2 (*Azotobacter vinelandii*), and Bs.fldA (*B. subtilis*).

In some embodiments, the fdx homologs comprise a sequence that is at least 60% identical to any one of SEQ ID NOs. 10 and 15-24. For example, the non-native fdx homologs can comprise a sequence that is at least about 60%, at least about 70%, at least about 80%, at least about 90%, at least about 95%, at least about 97%, at least about 98%, at least about 99%, or 100% identical to any of one of SEQ ID NOs. 10 and 15-24.

In some embodiments, the fldA homologs comprise a sequence that is at least 60% identical to any one of SEQ ID NOs. 25-28. For example, the non-native fldA homologs can comprise a sequence that is at least about 60%, at least about 70%, at least about 80%, at least about 90%, at least about 95%, at least about 97%, at least about 98%, at least about 99%, or 100% identical to any of one of SEQ ID NOs. 25-28.

In some embodiments, the bacterial strain has overexpression or complementation with one or more PFOR and/or fpr and, optionally, one or more of a flavodoxin (fldA), flavodoxin reductase, ferredoxin (fdx), and ferredoxin reductase. By way of example, in some embodiments the bacterial strain includes Ec.ydhV (*E. Coli*) (SEQ ID NO: 33) and Ec.ydhY (*E. Coli*) (SEQ ID NO: 34); Ec.ydbK (*E. Coli*) (SEQ ID NO: 9) and Cp.fdx (*Clostridium pasteurianum*) (SEQ ID NO: 10); Ec.fpr (*E. Coli*) (SEQ ID NO: 38) and Ec.fdx (*E. Coli*) (SEQ ID NO: 21); or Ec.fpr (*E. Coli*) (SEQ ID NO: 38) and Ec.fldA (*E. coli*) (SEQ ID NO: 27).

In some embodiments, the bacterial strain has overexpression or complementation with one or more PFOR, or a homolog thereof. By way of example, in some embodiments, the PFOR is selected from YdbK (SEQ ID NO: 9), Scy.pfor (*Synechocystis* sp.) (SEQ ID NO: 29), Ki.pfor (*Kluyvera intermedia*) (SEQ ID NO: 30), Da.pfor (*Desulfovibrio africanus*) (SEQ ID NO: 31), Ns.pfor (*Nostoc* sp.) (SEQ ID NO: 32), Ec.ydhV (*E. Coli*) (SEQ ID NO: 33), Ga.pfor (*Gilliamella apicola*) (SEQ ID NO: 35), and Sco.pfor (*Synechococcus* sp.). In some embodiments, the PFOR is YdbK.

In some embodiments, the PFOR comprise a sequence that is at least 60% identical to any one of SEQ ID NOs. 29-35. For example, the PFOR can comprise a sequence that is at least about 60%, at least about 70%, at least about 80%, at least about 90%, at least about 95%, at least about 97%, at least about 98%, at least about 99%, or 100% identical to any of one of SEQ ID NOs. 29-35.

In some embodiments, the overexpression or complementation with PFOR such as, e.g., YdbK, can result in improved performance through expression of electron carriers having a redox potential of about 400 to 550 mV, or in some embodiments, in the range of about 400 to 500 mV, or in the range of about 400 to 475 mV. In some embodiment, the electron carrier is ferrodoxin, flavodoxin, or NADPH. By way of example, in some embodiments, the electron carrier is Cv.fdx (*Allochromatium vinosum*).

In some embodiments, the bacterial strain has overexpression or complementation with one or more fpr homologs. By way of example, in some embodiments, the fpr homolog is selected from Ns.fpr (*Nostoc* sp.) (SEQ ID NO: 36), Sco.fpr (*Synechococcus* sp.) (SEQ ID NO: 37), and Ec.fpr (*E. Coli*) (SEQ ID NO: 38).

In some embodiments, the fpr comprise a sequence that is at least 60% identical to any one of SEQ ID NOs. 36-38. For example, the fpr can comprise a sequence that is at least about 60%, at least about 70%, at least about 80%, at least about 90%, at least about 95%, at least about 97%, at least about 98%, at least about 99%, or 100% identical to any of one of SEQ ID NOs: 36-38.

In some embodiments, the *E. coli* contains a deletion of one or more genes selected from: pgrR, mppA, ynaI, insH-4, ynaJ, uspE, fnr, ogt, abgT, abgB, abgA, abgR, mcaS, isrA, smrA, ydaM, ydaN, fnrS, C0343, dbpA, REP115, ttcA, intR, ydaQ, ydaC, ralA, ralR, recT, recE, racC, ydaE, and kilR.

The expression of the recombinant pgpB and/or nudB can be tuned to provide higher product titer, optionally by varying the promoter strength, gene copy number, position in an operon, and/or ribosome binding site. In some embodiments, the recombinant pgpB and/or nudB is expressed under control of a weak or intermediate strength promoter. The recombinant pgpB or nudB is integrated into the chromosome or expressed from a plasmid.

In various embodiments, the bacterial strain produces a terpene or terpenoid product that comprises at least one of Amorphadiene, Artemisinic acid, Artemisinin, Bisabolol, Bisabolene, alpha-Sinensal, beta-Thujone, Camphor, Carveol, Carvone, Cineole, Citral, Citronellal, Cubebol, Farnesene, Geraniol, Limonene, Menthol, Menthone, Myrcene, Nootkatone, Nootkatol, Patchouli, Piperitone, Rose oxide, Sabinene, Steviol, Steviol glycoside (including Rebaudioside D or Rebaudioside M), Taxadiene, Thymol, and Valencene.

Aspects and embodiments of the invention are further demonstrated below with reference to the following Examples.

EXAMPLES

Example 1: IspG/IspH Expression Tuning

Conclusions

Overexpression and balancing of MEP pathway genes can result in more carbon entering the MEP pathway, and can shift that carbon 'downstream' from DOXP and MEP to MEcPP. Modifying the expression of ispG and/or ispH might further convert MEcPP to HMBPP to IPP.

In fact, increasing expression of both ispG and ispH significantly increased titers of terpene and terpenoid products. However, increasing expression of just ispG or ispH alone did not improve titer. Overexpression of ispG alone resulted in growth defects, and overexpression of ispH alone didn't significantly improve titer, but did convert HMBPP to IPP. The effects of ispG overexpression could be related to the observation that HMBPP is not found extracellularly, but is found 100% intracellularly. Since the molecule does not appear to be transported out of the cell, it may act as a feedback molecule, providing a hard stop on the MEP pathway. For example, if the pool of HMBPP gets above a certain size, the pathway shuts down. Alternatively, or additional, HMBPP may be toxic at certain levels, which is consistent with the observation of the impact on IspG overexpression on cell growth.

Thus, the balance of activity between ispG and ispH is important to prevent HMBPP imbalance and accumulation. In some situations, less is more; that is, strongest overexpression of MEP genes can start to hurt productivity.

In summary, overexpressing ispG and ispH together, where one or both of ispG or ispH are wild-type or mutated/engineered, in a properly balanced configuration, prevents HMBPP accumulation from becoming toxic and pushes carbon through the MEP pathway to IPP, DMAPP, and the downstream terpene and terpenoid products.

Description of Experimental Results

Figure 2:
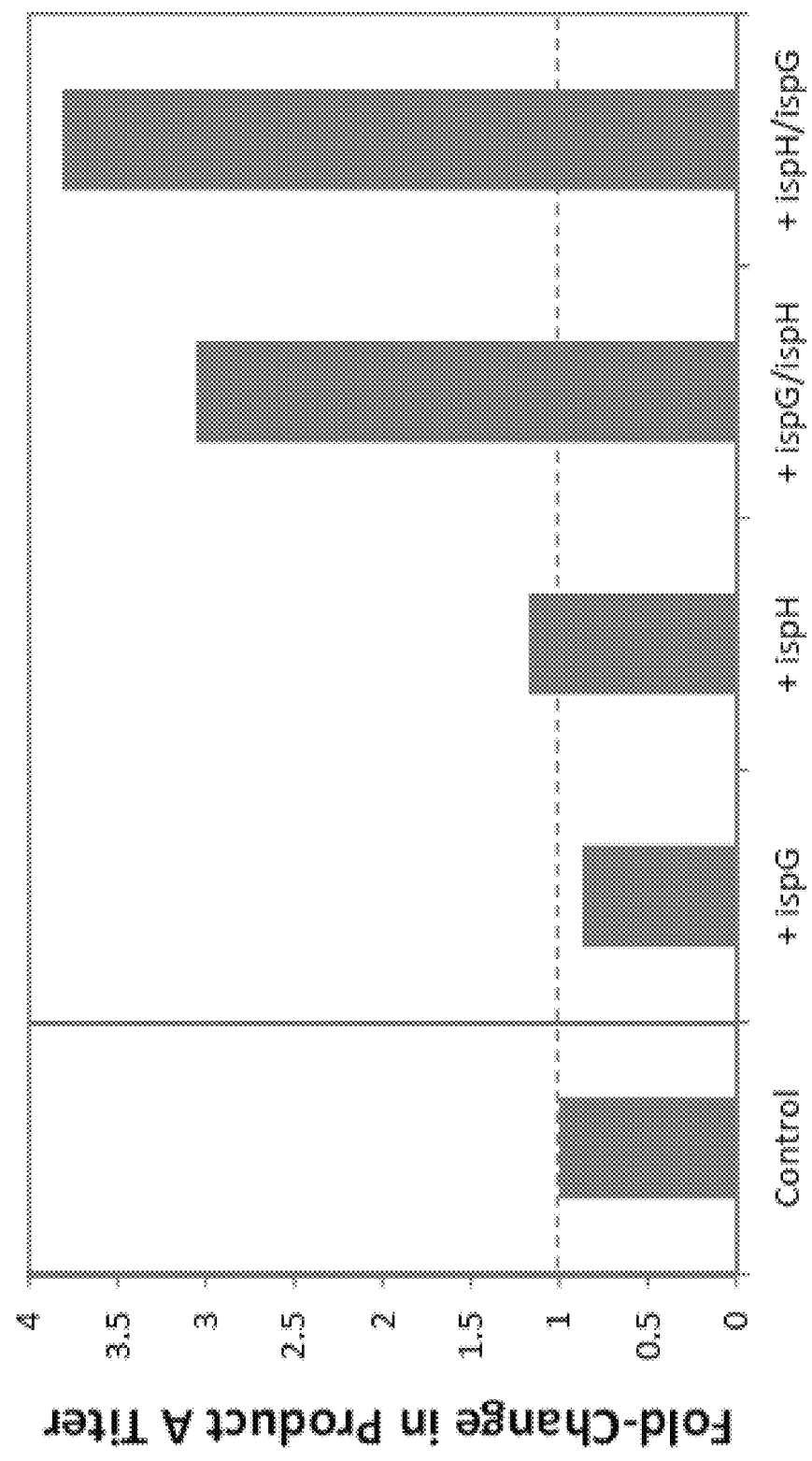
FIG. 2 shows that increasing expression of ispH alone or ispH and ispG together improve terpenoid product titers in strains engineered to increase the amount of carbon entering the MEP pathway, but ispG alone decreases productivity. The control strain is an *E. coli* strain with additional copies of dxs, dxr, ispD, ispE, ispF, and idi (no additional copies of ispG or ispH), among other changes to improve MEP pathway flux. Strains include a 20 kb deletion, which was not engineered.
Figure 3:
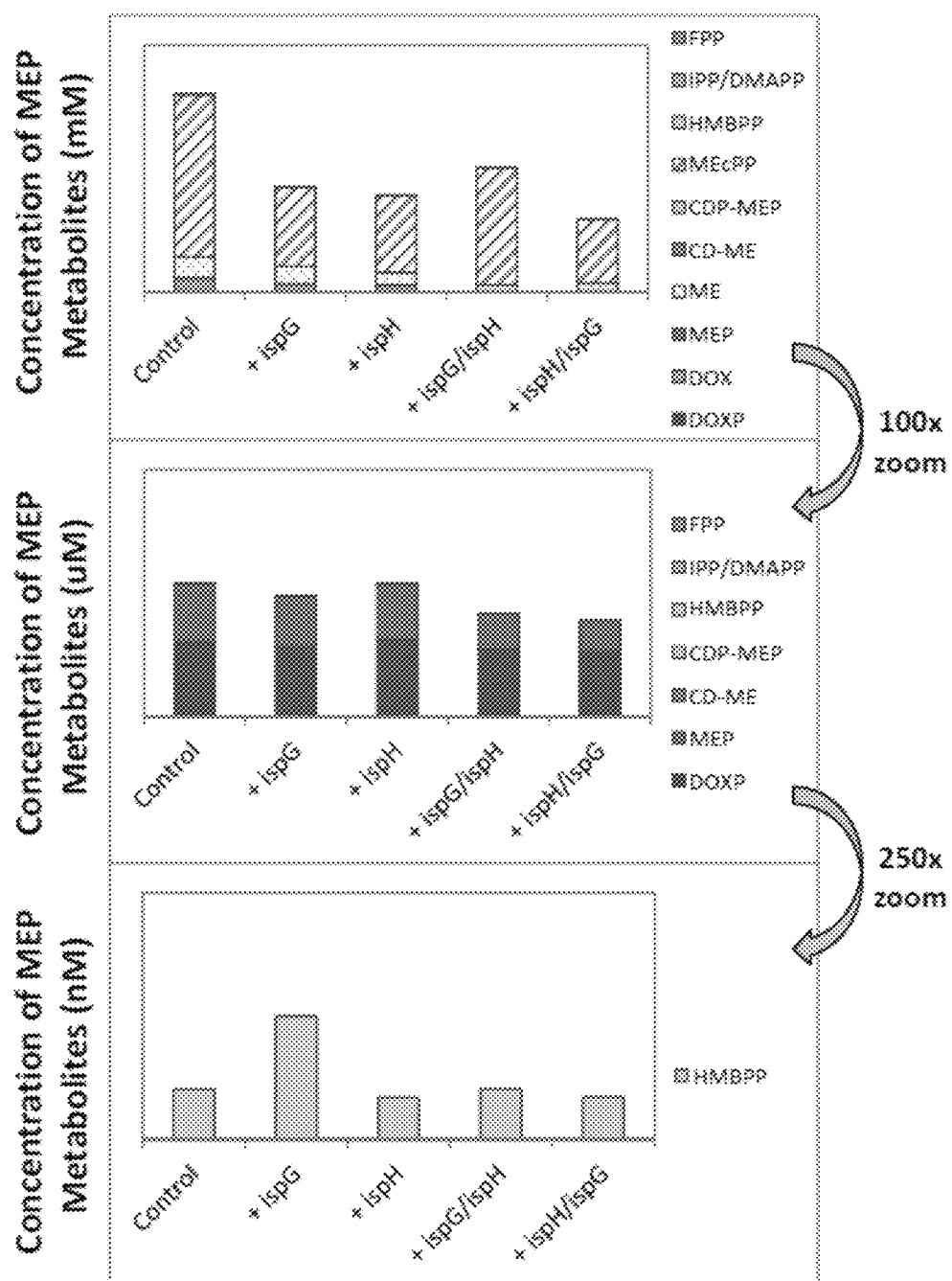
FIG. 3 shows that increasing ispG and/or ispH expression in modified production strains with enhanced MEP pathways impacts the MEP product distribution pattern. Upper panel (lx scale) shows all MEP pathway metabolites, with the majority of products being DOX, ME, and MEcPP. Middle panel (100× scale), shows MEP pathway metabolites with DOX, ME, and MEcPP not reported; in this case, DOXP and MEP are the most represented. Lower panel (25000× scale) shows only HMBPP concentration. In these panels, total extracellular and intracellular metabolites are shown from extracted cultures (broth plus cells), such that the reported concentration is relative to volume of extract.

FIG. 2 shows that increasing expression of IspH alone or IspH and IspG together improve terpenoid product titers in production strains that are already engineered to increase the amount of carbon entering the MEP pathway, but ispG alone decreases productivity. In this example, the control strain is an *E. coli* strain with balanced overexpression of MEP pathway genes (but no additional copies of ispG or ispH), increasing the amount of carbon entering the MEP pathway. As shown, overexpression of IspG decreases product titer about 15%, while overexpression of IspH at the same expression strength increases product titer 17%. Overexpression of both IspG and IspH more than triples product titer.

The data also shows that a ispG/ispH ratio that favors more H enzyme results in even more improved flux through the MEP pathway relative to a strain favoring the ispG side of the ratio. IspG and ispH are expressed here in operon format, and thus the second gene in the operon will have a lower expression level than the first. Thus, ispH/ispG operon showed significantly more product titer than ispG/ispH.

IspG and ispH work sequentially to convert MEcPP to HMBPP, then to IPP. Increasing ispG will accumulate a larger HMBPP pool, while increasing ispH will shrink the HMBPP pool as it is converted to IPP. The fact that IspG alone decreases productivity, while ispH alone increases it, strongly suggests that accumulation of HMBPP has a negative feedback effect on the MEP pathway. When both IspG and IspH are overexpressed, we enhance the rate of both HMBPP formation and consumption, which significantly improves flux through the MEP pathway to the target terpenoid. However, even in this enhanced flux regime, the balance of IspG to IspH is critical, since a slight favoring of ispH over ispG can further improve productivity by 25%, to nearly 4× the titers of a parent strain having wild-type expression of IspG and IspH.

Increasing IspG and/or IspH expression in the modified production strains with enhanced MEP pathways impacts on the MEP product distribution pattern (FIG. 3). The majority of products are DOX, ME, and MEcPP (FIG. 3, upper panel), followed by DOXP and MEP (FIG. 3, middle panel), and HMBPP (FIG. 3, lower panel). In these panels, total extracellular and intracellular metabolites are extracted from cultures (broth plus cells), such that the reported concentration is relative to volume of extract.

Increasing IspG or IspH alone increases the conversion rate of MEcPP and decreases the pool size (upper panel), even though IspH increases product titer and IspG loses product titer. A significant difference between the two variants is however apparent with the HMBPP concentration (lower panel), where IspG alone increases it 2.5× over the control, while IspH alone decreases it 20%. This accumulation of HMBPP could be feeding back on the MEP pathway and shutting down the enhancement of flux. HMBPP accumulates to very low levels (nM concentration), and 100% of it is found intracellularly.

Increasing ispG and ispH expression together, in either operon order, can be seen to enable complete conversion of the remaining DOX, and decreases the ME pool size. Moreover, a IspG/IspH ratio that favors more IspH is capable of improved conversion of MEcPP (and improved product titer) compared to a strain favoring IspG.

Figure 4:
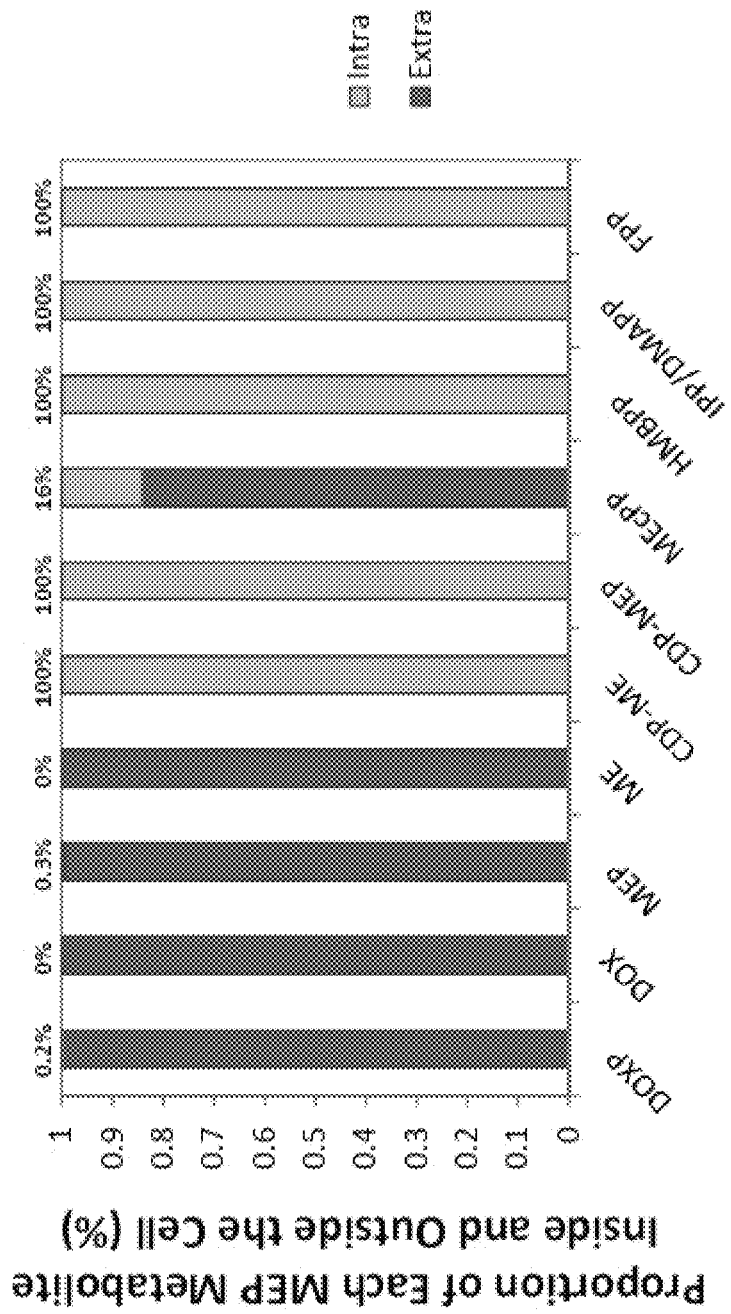
FIG. 4 shows the proportion of each individual MEP metabolite found inside or outside the cell ('Intra' vs 'Extra'). These values do not reflect absolute abundance, e.g. there is far more DOX in total than there is HMBPP. While DOX is 100% extracellular, HMBPP is 100% intracellular. The strain profiled in FIG. 4 is the 'Control+ispH/ispG' top performing strain. DOXP/DOX, MEP/ME, and MEcPP accumulate almost entirely, if not entirely, in the extracellular medium, while CDP-ME, CDP-MEP, HMBPP, IPP/DMAPP, and FPP are observed 100% intracellularly. The percentage of each metabolite found intracellularly is shown at the top of the graph.

The proportion of each individual MEP metabolite found inside or outside the cell ('Intra' vs 'Extra') is shown in FIG. 4. These values do not reflect absolute abundance, as shown in FIG. 3, there is far more DOX in total that there is HMBPP. While DOX is 100% extracellular, HMBPP is 100% intracellular. The strain profiled here is the 'Control+ ispH/ispG' top performing strain from FIGS. 2 and 3. DOXP/DOX, MEP/ME, and MEcPP accumulate almost entirely in the extracellular medium, while CDP-ME, CDP-MEP, HMBPP, IPP/DMAPP, and FPP are observed 100% intracelluarly. The percentage of each metabolite found intracellularly is shown at the top of the graph.

Figure 5:
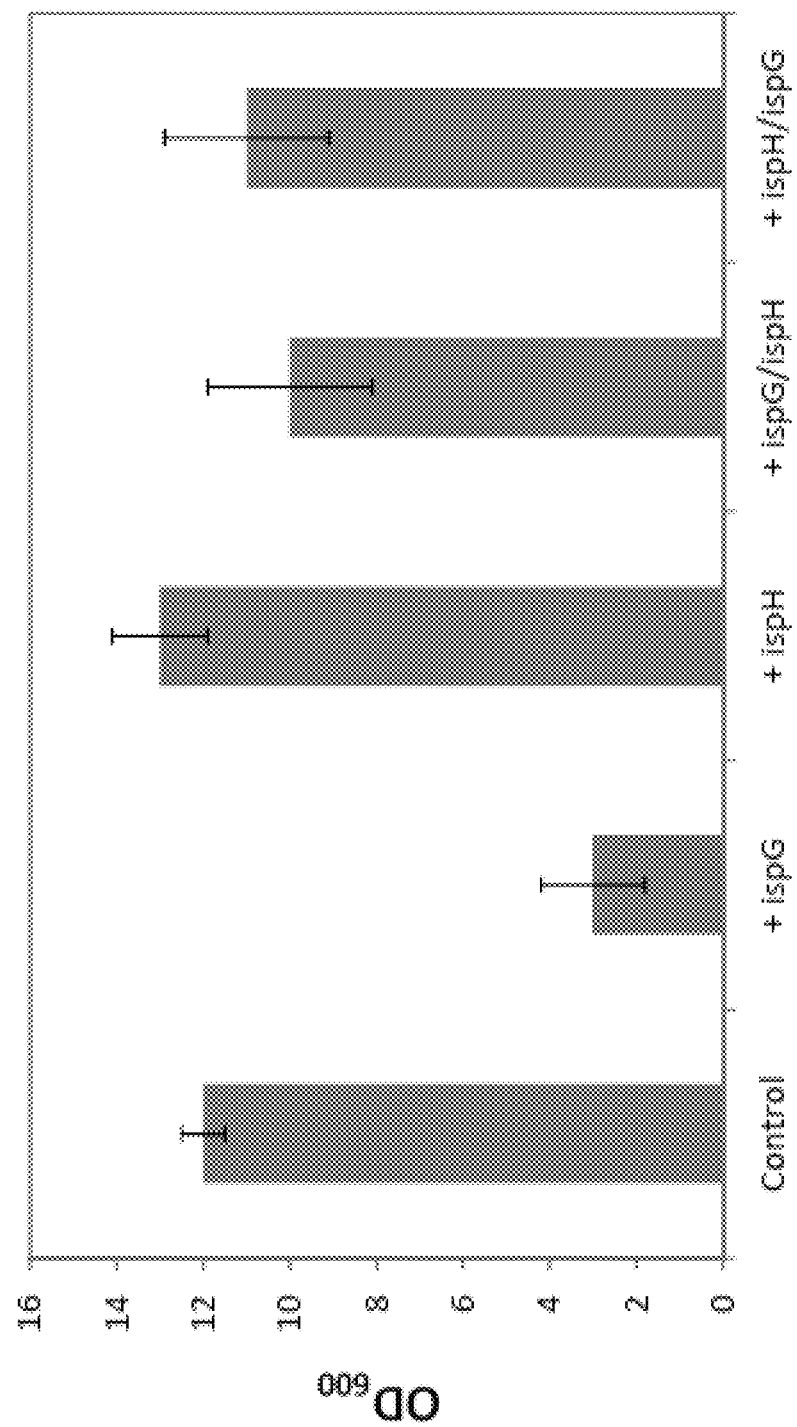
FIG. 5 shows that uncompensated ispG upregulation causes a significant drop in cell growth, as determined by UV absorbance at 600 nm. While some changes to final cell density is observed in strains compensated with ispH or ispH and ispG together, the variation is not significant.

Uncompensated ispG upregulation causes a significant drop in cell growth, as determined by UV absorbance at 600 nm (FIG. 5). While some changes to final cell density are observed in a strain compensated with ispH or ispH and ispG together, the variation is not significant.

To determine HMBPP accumulation, HMBPP can be expressed in terms of dry cell weight (DCW). For example, using a strain with balanced ispGH expression:

[HMBPP]=0.42 ug/mL in 0.35 mL sampled culture

[OD600]=12.69

Assumption: 1 OD600=0.4 g-DCW/L=0.4 mg-DCW/mL $$\text{HMBPP yield}=[(0.42\ \text{ug/mL})*(0.35\ \text{mL})]/[(12.69*0.4\ \text{mg-DCW/mL})*0.35\ \text{mL})]$$

In this example, HMBPP=0.0827 ug/mg DCW or 0.0827 mg/g DCW.

Example 2: pgpB and nudB Overexpression

Conclusions

Installing an alternate 'product' pull by overexpressing genes such as pgpB and nudB can pull even more flux through the MEP pathway (though to non-target products), or could even replace the various downstream terpenoid pathways to create a tool to engineer a 'universal chassis' (i.e., a strain that can have any terpenoid downstream transformed into it and be quickly optimized for commercial production).

Carbon can be pulled through the MEP pathway to create alternate products that will pool outside the cell. PgpB dephosphorylates FPP to farnesol (FOH), and nudB dephosphorylates IPP and DMAPP to isoprenol (3-methyl-3-buten-1-ol) and prenol (3-methyl-2-buten-1-ol), respectively. Enhancing transport of these products outside the cell prevents buildup of IPP, DMAPP, and FPP; which like HMBPP, can feedback and exert control on the MEP pathway. IPP inhibits growth and feedback inhibits Dxs. See Cordoba, Salmi & Leon (2009) *J. Exp. Bot.* 60, 10, 2933-2943. FPP feedback inhibits IspF-MEP complex, which itself is formed when MEP binds and enhances IspF activity in a feed-forward manner. Bitok & Meyers (2012) *ACS Chem. Biol.* 2012, 7, 1702-1710. These products accumulate outside the cell and, like the intermediates in the MEP pathway, can be used to track C-flux through the MEP pathway via LC/MS metabolomics quantitation.

By constitutively expressing an additional copy of pgpB, carbon flux through the MEP pathway can be improved, and a slow growth phenotype ameliorated in a strain that has MEP genes overexpressed but no additional downstream pathway to pull all that carbon through to product. In effect, the downstream 'pull' becomes the conversion of FPP to farnesol, which is exported outside the cell. Similarly, constitutive expression of nudB should result in IPP and DMAPP pools being increasingly redirected to isoprenol and prenol extracellular products.

Further modulating the expression levels of MEP pathway genes in the presence of overexpressed pgpB or nudB can significantly impact the MEP flux and carbon distribution through the pathway. The increase or decrease in farnesol, prenol, or isoprenol product can be inversely correlated with MEcPP level.

Description of Experimental Results

Figure 6:
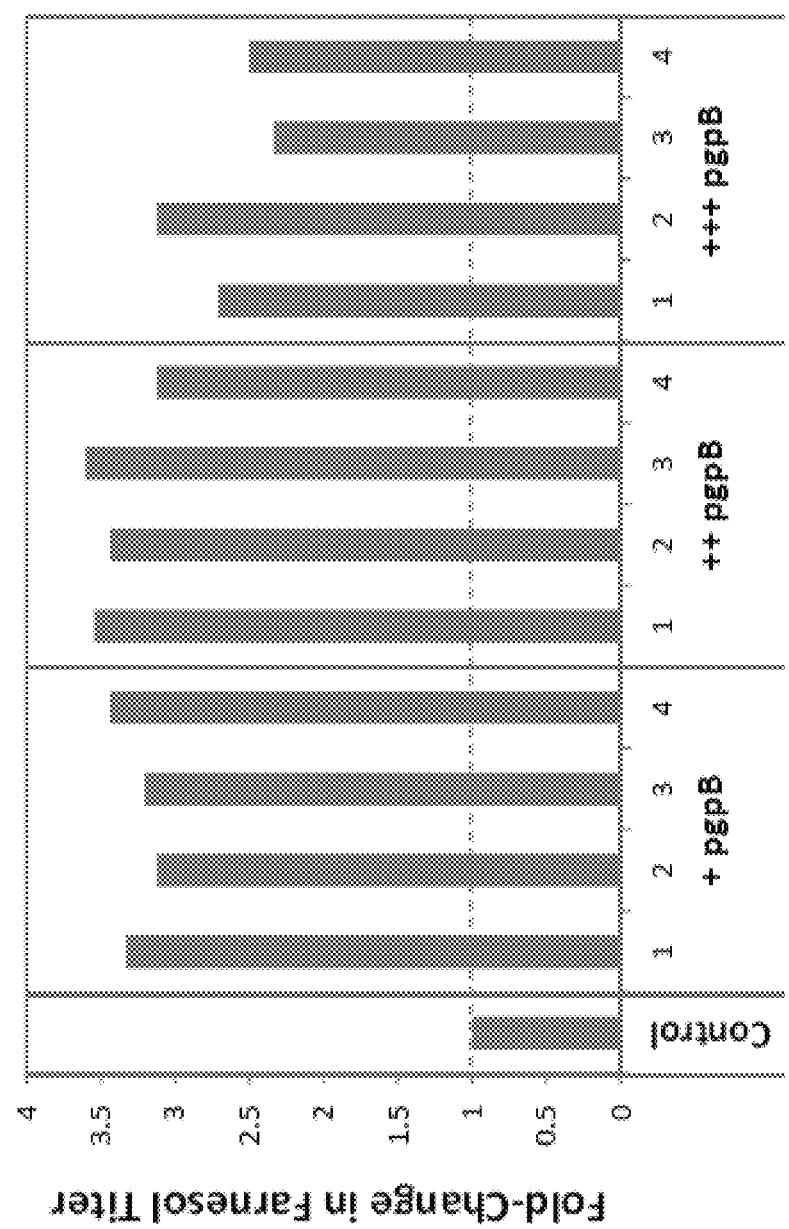
FIG. 6 shows that overexpression of pgpB can triple farnesol titers in strains engineered to enhance flux through MEP pathway, but without a downstream terpenoid product pathway installed. The control strain has additional copies of dxs, dxr, ispD, ispF, ispE, ispG, ispH, and idi under varying levels of constitutive expression, and also has ydbK overexpressed. The strain accumulates moderate amounts of farnesol, presumably as 'spill-over' from too much FPP accumulation, which feeds back on the pathway, and suffers from markedly slower growth compared to wild-type. When pgpB is overexpressed in this strain, the excess FPP is more efficiently converted to farnesol (preventing feedback control) and the flux is effectively pulled through the MEP pathway.

Overexpression of PgpB can triple farnesol titers in strains engineered to enhance flux through the MEP pathway, but without a downstream terpenoid product pathway installed (FIG. 6). The control strain has additional copies of dxs, dxr, ispD, ispF, ispE, ispG, ispH, and idi under varying levels of constitutive expression, and also has YdbK overexpressed (Example 4). The control accumulates moderate amounts of farnesol, presumably as 'spill-over' from too much FPP accumulation, which feeds back on the pathway, and suffers from markedly slower growth compared to wild-type. When PgpB is overexpressed in this strain, the excess FPP is more efficiently converted to farnesol (preventing feedback control) and the flux is effectively pulled through the MEP pathway.

However, too much PgpB expression (the '+++' condition) seems to negatively impact the total flux through to farnesol, with lower titer and smaller fold-change observed, on average. Some potential reasons for this result include: (1) too hard a pull from the PgpB is straining the MEP pathway's ability to keep up with FPP demand, especially from required competing products; or (2) since PgpB is known to dephosphorylate multiple targets in vivo, including an essential membrane phospholipid, a high expression level for PgpB could be having unintended negative consequences on cell health.

Increasing and tuning expression of IspG' and/or IspH in a strain that produces farnesol can improve product titer (FIG. 7). In this example, the IspG' enzyme is an engineered version with higher activity than wild-type. The control strain has additional copies of dxs, dxr, ispD, ispF, ispE, ispG, ispH, and idi, as well as additional copies of YdbK and pgpB. Additional copies of ispH and/or ispG' are integrated into the strains under increasing promoter strength (+, ++, +++).

When IspH is overexpressed (FIG. 7, panel A), no significant change in product titer is observed. While increasing the amount of IspH is going to improve conversion of HMBPP to IPP, there is no additional IspG' to provide that additional HMBPP. The MEcPP pool mediated by IspG activity becomes the rate-limiting step in the pathway. However, when IspG' is overexpressed in addition to IspH (FIG. 7, Panel B), we see a significant increase in the farnesol product titer. In this situation, the additional HMBPP enabled by the additional copy of IspG' is rapidly converted by the increased IspH level to IPP, preventing HMBPP from accumulating and feeding back on the pathway.

It is clear that the balance between IspG and IspH is critical. The data shows IspG/H being expressed in operon format, such that the second gene in the operon will have a lower expression level than the first. When the gene order in the operon for ispG' and ispH is switched (i.e., ispH+ispG' versus ispG'+ispH) and thus changing the expression ratio of IspG'/IspH, we see opposite trends in the data. When the ratio favors IspH over IspG' (B), an increasing promoter strength results in steadily increasing product titer. However, when the ratio favors IspG' over IspH (C), the excess HMBPP that can be created by this imbalanced pathway steadily accumulates as promoter strength increases, resulting in less and less product improvement and slower growth.

Increase in farnesol product titer can be accompanied by a decrease in MEcPP pool size, though it depends on the ratio of IspG and IspH (FIG. 8). As seen in FIG. 7, additional copies of IspG' and IspH in farnesol producing strains can improve farnesol product titer up to 2.5-fold. When only IspH is upregulated without additional IspG (FIG. 8, Panel A), titer did not change significantly, nor did MEcPP. MEcPP does decrease moderately, likely due to MEcPP being pulled downstream as HMBPP is more efficiently converted to IPP by the extra IspH enzyme. When relatively more IspH was expressed than IspG' (FIG. 8, Panel B), as promoter strength increases, farnesol product titer increased. MEcPP conversely decreases as it is consumed by a balanced pathway that distributes the flux to the desired end product.

However, even though a non-optimal ratio favoring IspG' over IspH can improve MEcPP conversion through HMBPP to IPP and improve farnesol product titer, eventually the imbalance is too severe for the *E. coli* strain to tolerate and the product improvement disappears, while even more MEcPP accumulates and is trapped in the MEP pathway intermediate carbon pool.

Example 3: Idi Expression Tuning

Conclusions

Idi enzyme catalyzes the reversible isomerization of IPP to DMAPP. Since every desired terpenoid product or undesired MEP side-product (e.g., UPP) uses one DMAPP and varying numbers of IPP, the ratio between the two precursors could have a fundamental impact on strain productivity. For example, 1 FPP=1 DMAPP+2 IPP, whereas 1 UPP=1 FPP+8 IPP (or 1 DMAPP+10 IPP). Therefore, an optimal ratio for FPPS to produce FPP is 2:1 IPP:DMAPP, but 10:1 for UPP. Thus, varying the ratio of IPP:DMAPP by varying idi expression will have an impact on the production of the desired terpenoid relative to other undesired products from the MEP pathway.

Description of Experimental Results

Idi was complemented in different strains producing product A or B. Cells were cultured in 96-round-well culture plates at 37° C. for 48 hrs at 280 RPM in custom media with glucose as carbon source. Idi was expressed from a pBAC under an IPTG-inducible promoter. Strain 1 already has dxs, dxr, ispD, ispF, ispE, idi, FPPS, and YdbK overexpressed, while Strains 2 and 3 further have ispH and a mutant version of IspG overexpressed in addition. Conversely, Strain 4 has the same enzymes overexpressed but under a very different expression regime.

While Idi overexpression increases product titer in a strain that does not overexpress ispGH, it decreases titer in two strains that do, indicating that the balance between IPP and DMAPP controlled by Idi can be tuned up or down depending on the needs of the downstream pathway (FIG. 9). However, Strain 4 more than doubles titer with idi complementation. The same genes are overexpressed in this strain, but the balance between the expression of the MEP genes is very different.

Example 4: YdbK Overexpression

Conclusions

YdbK is predicted to function as a pyruvate:flavodoxin oxidoreductase and/or pyruvate synthase. The oxidoreductase is thought to oxidize pyruvate to acetyl-CoA, reducing ferredoxin, which can then supply electrons to the MEP pathway, especially to support the strongly upregulated IspG and IspH enzymes that contain Fe—S clusters. YdbK overexpression has been shown for hydrogen (H2) production (Akhtar M K & Jones P R (2014), Cofactor engineering for enhancing the flux of metabolic pathways." *Frontiers in Bioeng. and Biotech.*), but not for terpenoid production.

The product titer of terpene Product A doubled in these strains. The Fe—S clusters are better supported by the extra YdbK cofactor, and their activity improves. Product titer goes up, and when the MEP metabolites are profiled, we see an increased conversion of MEcPP, similar to what is observed when the control strain further adds another copy of ispH-ispG' operon.

On the other hand, when a Product B strain that didn't have IspG/H overexpressed relative to WT, was complemented with YdbK, the Product B titer went down. When IspG/H was increased in this strain, YdbK complementation did improve Product B titer, suggesting that YdbK expression has to be carefully balanced with IspG/H expression (which, in turn must be carefully balanced for H/G ratio).

Additionally, extra electron-carrying or transferring cofactors were added on top of the YdbK overexpression to see if we can further improve titers. In some experiments, YdbK plus fdx (ferredoxin) from *Clostridium pasteurianum* improved productivity somewhat.

Description of Experimental Results

An additional copy of *E. coli* YdbK gene is integrated into chromosome or expressed on a plasmid (specifically a single-copy pBAC, or multi-copy plasmids), under control of constitutive or inducible promoters. Additionally, copies of native or non-native recombinant electron acceptor/donors can also be overexpressed with YdbK, to capitalize on and utilize most efficiently the additional electrons made available for biosynthesis.

Expressing an additional copy of YdbK under increasing promoter strength can improve terpenoid production. In this example, the control strain produces terpenoid product A, and has additional copies of genes dxs, dxr, ispD, ispE, ispF, ispG', ispH, and idi of the MEP pathway under defined constitutive expression.

Figure 10:
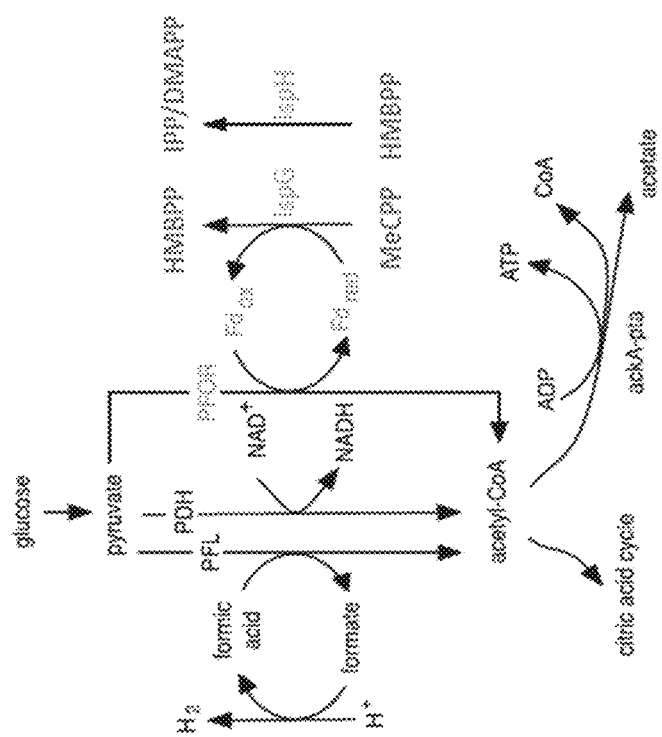
FIG. 10 illustrates the role of YdbK as a pyruvate: flavodoxin oxidoreductase and/or pyruvate synthase in enhancing terpenoid biosynthesis.
Figure 10:
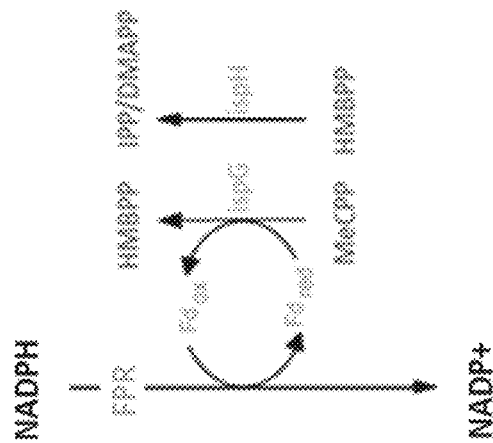

In this strain, adding an extra copy of ispH and ispG' in operon format (such that the H/G' ratio favors H) further increases the Product A titer, indicating that these steps are limiting (FIG. 10, Panel A). Increasing these Fe—S cluster-containing genes clearly increases the conversion of MEcPP and lowers the concentration observed in culture (FIG. 10, Panel C).

When YdbK is complemented in the control strain, we see a graded response to upregulation, where increasing expression sees increasing terpenoid production, up to a point—moving to stronger expression results in 50% less Product A in the +++ YdbK strain (FIG. 10, Panel B). We see the same conversion of MEcPP occurring for these strains (FIG. 10, Panel D), suggesting that YdbK is supporting enhanced IspG and/or IspH activity. Of note, the MEP metabolite profile of ++ vs +++ strains doesn't change significantly, but has ~3× less product titer, suggesting that some kind of feedback mechanisms has been activated. Given the observations of work with IspG and IspH, it is possible that this feedback is due to HMBPP accumulation.

Figure 11:
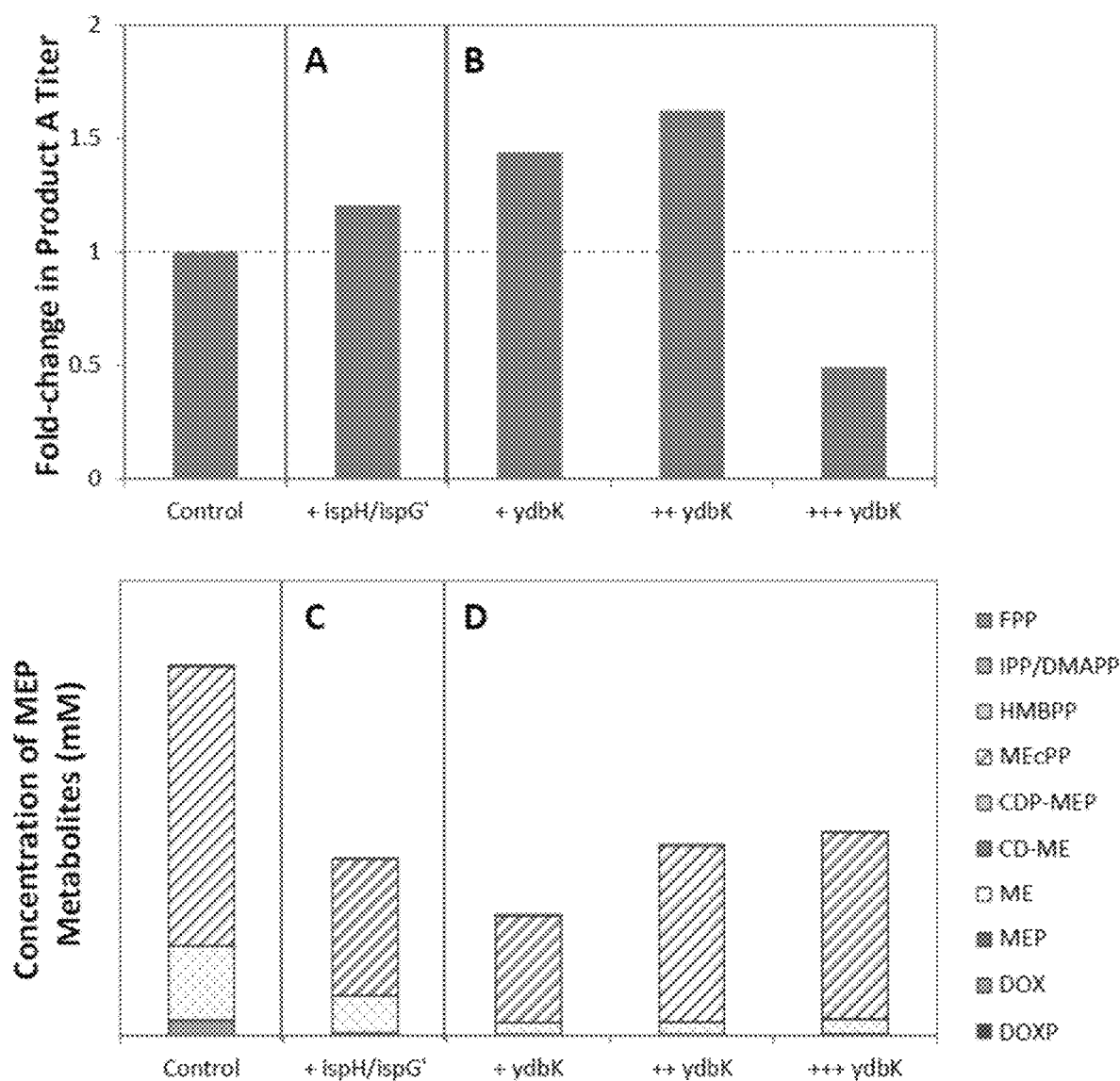
FIG. 11 shows that expressing an additional copy of ydbK under increasing promoter strength can improve terpenoid production. The control strain produces terpenoid product A, and has additional copies of genes dxs, dxr, ispD, ispE, ispF, ispG', ispH, and idi of the MEP pathway under defined constitutive expression.

The improvement in terpenoid product titer from increasing YdbK expression requires sufficient IspG and/or IspH to be manifested (FIG. 11). In this example, Control A has additional copies of dxs, ispD, ispF, and idi of the MEP pathway, as well as rhyB deletion and isc operon changes. Control B is Control A plus an additional integrated copy of ispG' and ispH in operon configuration (G' first, such that the H/G ratio favors G), while Control C is Control A plus an additional integrated copy of ispH and ispG' in operon configuration (H first, such that the H/G ratio favors H).

In Panel A, we see that complementing YdbK in the absence of IspG/H upregulation decreases terpenoid Product B titer by about 25%. However, when you complement YdbK in strains with additional copies of ispG'-ispH or ispH-ispG', we observed 18% and 27% improvement in terpenoid titers. Clearly, IspG and IspH must be overexpressed relative to WT MEP pathway to see the benefit of YdbK.

Moreover, this data again highlights how important the expression balance between IspG and IspH can be for MEP pathway flux and terpenoid productivity. In control B vs. C, the same enzymes are upregulated under the same promoter strength—the difference lies in the order of genes in the operon. The genes closest to the promoter will be expressed more strongly than subsequent genes in the operon, such that the H/G enzymes ratio favors IspG in Control B or IspH in Control C. Given this, we observe that a ratio favoring H improves titer more so than one favoring G. Moreover, the improvement made possible by YdbK is enhanced in a strain favoring H. Thus, the balance between IspH and IspG is very important to strain productivity.

Figure 12:
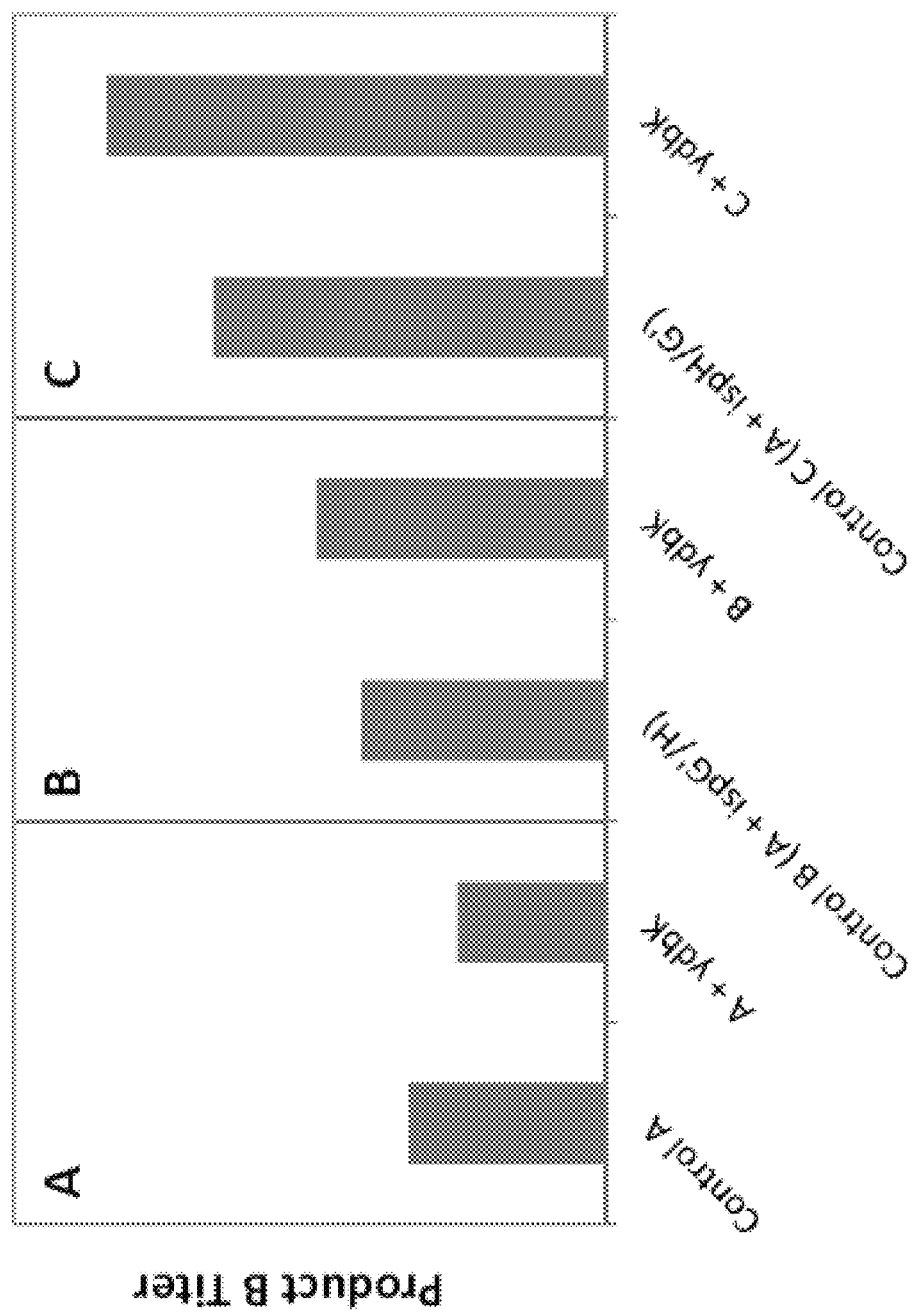
FIG. 12 shows that improvements in terpenoid product titer from ydbK overexpression requires sufficient ispG and/or ispH. Control A has additional copies of dxs, ispD, ispF, and idi of the MEP pathway, a non-engineered 20 kb deletion, as well as other modifications to improve performance of iron-sulfur cluster proteins. Control B is Control A plus an additional integrated copy of ispG' and ispH in operon configuration (G' first, such that the H/G ratio favors G), while Control C is Control A plus an additional integrated copy of ispH and ispG' in operon configuration (H first, such that the H/G ratio favors H).
Figure 13:
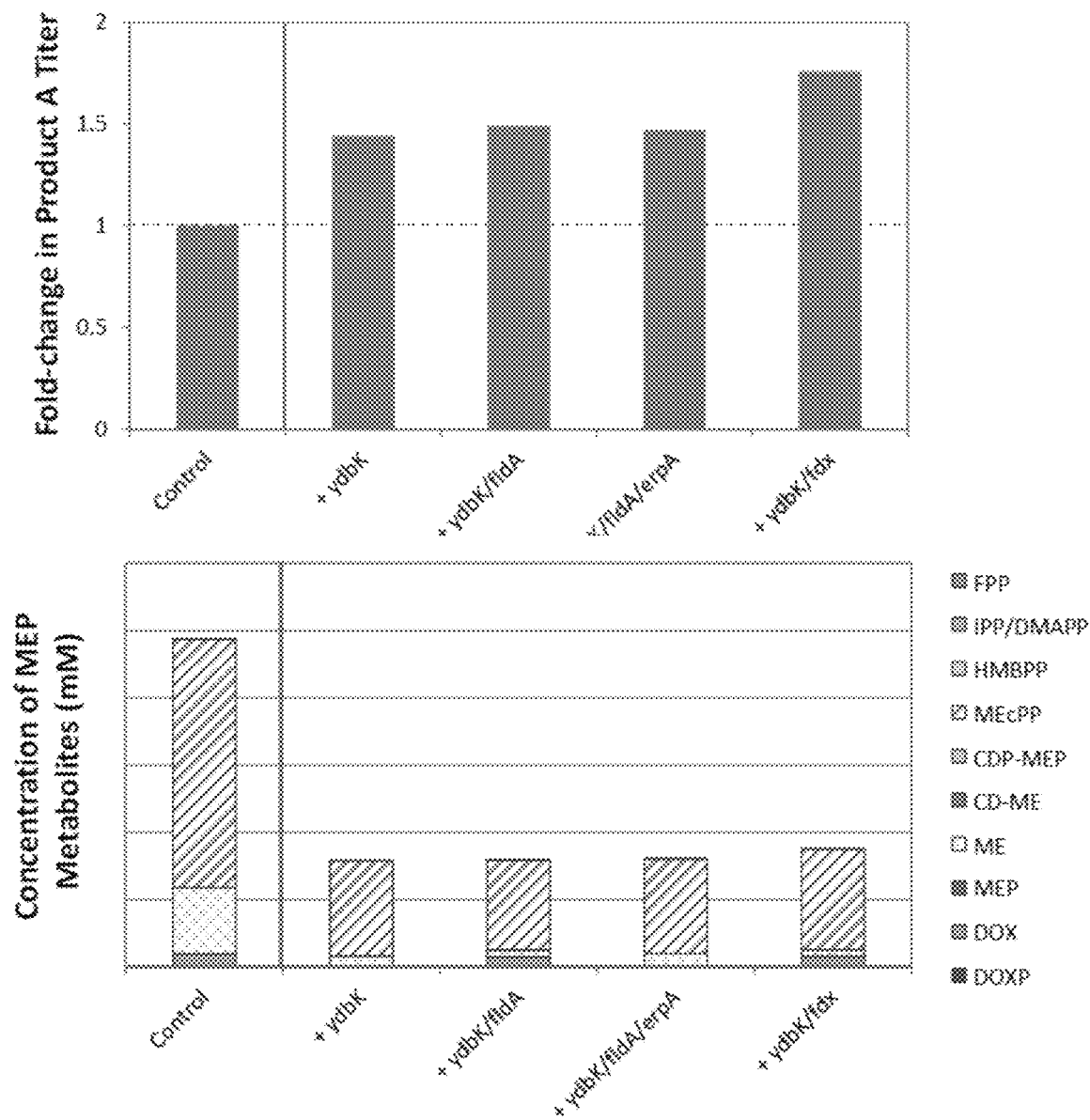
FIG. 13 shows that expressing fdx in addition to ydbK can improve terpenoid titers. The control strain produces terpenoid product A, and has additional copies of genes dxs, dxr, ispD, ispE, ispF, ispG', ispH, and idi of the MEP pathway under defined constitutive expression. The strain also has a non-engineered 20 kb deletion and other modifications to improve performance of iron-sulfur cluster proteins.

Expressing fdx in addition to YdbK can further improve terpenoid titers (FIG. 12). In this example, the control strain produces terpenoid product A, and has additional copies of genes dxs, dxr, ispD, ispE, ispF, ispG', ispH, and idi of the MEP pathway under defined constitutive expression.

As shown in FIG. 10, expressing an additional copy of YdbK under constitutive expression increases the production of Product A. Complementing was attempted with three additional electron acceptors/donors, fldA, fldA and erpA (each from *E. coli*), or fdx from *Clostridium pasteurianum* (which may support 4Fe-4S clusters, as are found in IspG and IspH, rather that 2Fe-2S clusters).

Adding another copy of fldA (flavodoxin) or fldA and erpA (essential respiratory protein A) in addition to YdbK did not further improve Product A titer, but adding *Clostridium pasteurianum* fdx did improve titers of Product A. Interestingly, while addition of YdbK results in complete conversion of DOX/DOXP downstream to ME/MEP, further adding fldA causes some carbon to pool upstream in the MEP pathway as DOX/DOXP. Adding erpA to the mix restores the profile. However, the MEP metabolite profile for the further enhanced ydbK+fdx strain is most similar to ydbK+fldA, suggesting that optimum MEP flux will result from coordinated balancing of the MEP pathway gene expression as well as expression of critical electron donor/acceptors.

Example 5: Reducing PDH Conversion of Pyruvate to Acetyl-COA Enhances YdbK Conversion of Pyruvate to Acetyl-COA Increasing the reliance on YdbK for the conversion of pyruvate to acetyl-COA can improve the production of terpenes and/or terpenoid products by the engineered microbial strain because YdbK has a lower redox potential (larger absolute number in Table 4) than the FMN hydroquinone/semiquinone couple in fldA. As such, YdbK is the preferred source of electrons (not fpr/NADPH) by IspG and IspH.

Iron sulfur clusters (e.g., $Fe_4S_4$) in enzymes (such as IspG and IspH) utilize a wide range of reduction potentials, e.g., −200 to −800 mV. Blachly, et al., *Inorganic Chemistry*, 54(13): 6439-6461 (2015).

Reduction potentials for charging electron carriers YdbK and fpr are disclosed in Tables 2 and 3, respectively, and reduction potentials for discharging electron carries (e.g., YdbK and fpr) to IspG and IspH are disclosed in Table 4. See McIver, et al., *FEBS J*, 257(3):577-85 (1998) and Lupton, et al., *J Bacteriol*, 159: 843-9 (1984).

TABLE 2

| Charging Electron Carrier YdbK | | |
|---|---|---|
| | $\epsilon^0$ (mV) | $\Delta G^0$ (kcal/mol pyruvate) |
| YdbK oxidation half reaction: | | |
| pyruvate + CoA → acetyl-CoA + $CO_2$ + $2H^+$ + $2e^-$ | 540 (*D. africanus*) | |
| Potential electron carrier reduction half reactions: | | |
| 2 oxidized fldA + $2e^-$ + $2H^+$ → 2 semiquinone fldA | −254 | −13.2 |
| 2 fdx $2Fe(III)^{2+}$ + $2e^-$ → 2 fdx $Fe(III)^{2+}Fe(II)^{1+}$ | −380 | −7.4 |
| 2 semiquinone fldA + $2e^-$ + $2H^+$ → 2 hydroquinone fldA | −433 | −4.9 |

TABLE 3

Charging Electron Carrier fpr

| | | $\varepsilon^0$ (mV) | $\Delta G^0$ (kcal/mol NADPH) |
|---|---|---|---|
| Step 1 | NADPH oxidation half reaction: | | |
| | NADPH→ NADP$^+$ + 2e$^-$ + H$^+$ | 320 (370 for NADPH/ NADP+ = 60) | |
| | Potential fpr reduction half reactions: | | |
| | 2 oxidized fpr + 2e$^-$ + 2H$^+$ → 2 semiquinone fpr | −308 | −0.6 |
| | 2 semiquinone fpr + 2e$^-$ + 2H$^+$→ 2 hydroquinone fpr | −268 | −2.4 |
| Step 2 | Potential fpr oxidation half reaction: | | |
| | semiquinone fpr → oxidized fpr + e$^-$ + H$^+$ | 308 | |
| | hydroquinone fpr→ semiquinone fpr + e$^-$ + H$^+$ | 268 | |
| | Potential electron carrier reduction half reactions: | | |
| | oxidized fldA + e$^-$ + HP$^+$→ semiquinone fldA | −254 | −2.5 or −0.6 |

TABLE 4

Discharging Electron Carriers to IspG and IspH

| Potential electron carrier oxidation half reactions: | $\varepsilon^0$ (mV) | Source |
|---|---|---|
| 2 semiquinone fldA → 2 oxidized fldA + 2e$^-$ + 2H$^+$ | 254 | Fpr, YdbK |
| 2 fdx Fe(III)$^{2+}$Fe(II)$^{1+}$→ 2 fdx 2Fe(III)$^{2+}$ + 2e$^-$ | 380 | YdbK |
| 2 hydroquinone fldA → 2 semiquinone fldA + 2e$^-$ + 2H$^+$ | 433 | YdbK |

The optimal activity of IspG was tested in vitro by using a range of redox dyes. Xiao, et al., *Biochemistry*, 48(44): 10483-10485 (2009). The optimal activity of IspG was tested with externally fed methyl viologen ($\varepsilon^0$=446 mV). The activity of IspG using fed methyl viologen ($\varepsilon^0$=446 mV) was 20× greater than an in vitro fpr-fldA system.

IspH activity was 50× greater with methyl viologen ($\varepsilon^0$=446 mV) and 100× greater with the externally fed dithionite-MDQ ($\varepsilon^0$=490 mV). Xiao, et al., Journal of the American Chemical Society, 131(29): 9931-9933 (2009).

It is hypothesized that the fldA semiquinone/hydroquinone couple that is accessible by YdbK, but not fpr, is the preferable in vivo reduction system for IspG and IspH.

In order to increase a microbial strain's reliance on PFOR (e.g., YdbK) mediated conversion of pyruvate to acetyl-COA, PDH mediated conversion of pyruvate to acetyl-COA was reduced. See FIG. 15.

There are three known reactions in *E. coli* to convert pyruvate (PYR) to acetyl-CoA (AcCoA): pflB, PDH, and PFOR or YdbK.

Out of the three enzymes, PDH predominates and is a multi-enzyme complex (aceE-aceF-lpd), which consists of 24 subunits of pyruvate dehydrogenase (aceE), 24 subunits of lipoate acetyltransferase (aceF), and 12 subunits of dihydrolipoate dehydrogenase (lpd). The net reaction of the PDH system, in addition to reducing NAD+, is the conversion of pyruvate into AcCoA and $CO_2$, a key reaction of central metabolism because it links glycolysis I, which generates pyruvate, to the TCA cycle, into which the AcCoA flows. During aerobic growth, PDH is an essential source of AcCoA to feed the TCA cycle and thereby to satisfy the cellular requirements for the precursor metabolites it forms. Mutant strains defective in the PDH complex require an exogenous source of acetate to meet this requirement.

pflB is only active in anaerobic condition. As such, it is not a primary reaction to convert PYR to AcCoA under microaerobic and aerobic conditions.

In microbial strains with at least YdbK overexpression, PDH (see, e.g., Example 4) is no longer essential since YdbK can be used to supply AcCoA. To ensure the PYR to AcCoA step is mainly catalyzed by YdbK, which in turn supplies electrons to IspG and IspH, PDH activity was reduced or eliminated through gene knockouts or knockdowns (e.g., by mutation).

Elimination of PDH Via Knockout of aceE

Four different *E. coli* strains engineered to produce four different terpenoid products (indicated as Product B, Product C, Product D, and Product E) were further engineered to knockout aceE (ΔaceE), which eliminated PDH activity. Control strains were the same, but without the aceE knockout.

The data shows an increase in titer of each of the four terpenoid products through the deletion of aceE as compared to control. See FIGS. 16A-D. Differences in fold-change improvement can largely be attributed to the biochemical characteristics (e.g., Km and k$_{cat}$) of the different terpenoid synthase enzymes employed for the downstream pathway. Specifically, enzymes with lower synthase activity compared to the Product D synthase (the most catalytically efficient) had slightly lower fold-change improvements, presumably due to the accumulation of the FPP substrate, which can accumulate and lead to either cell toxicity or feedback regulation on upstream components of the MEP pathway.

Figure 16A:
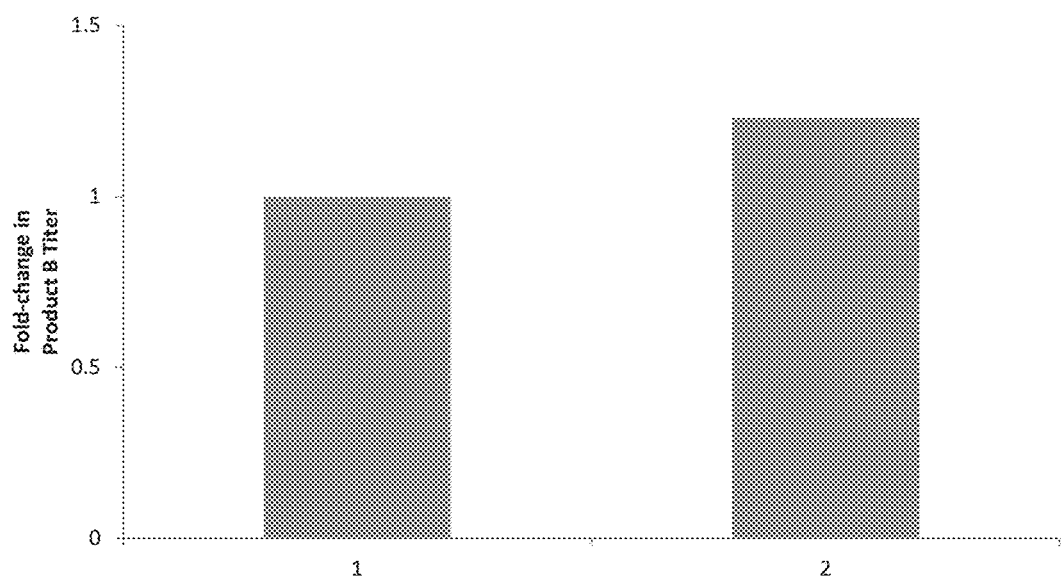
FIGS. 16A-D are graphs showing the fold change in terpenoid product production in bacterial strains having overexpressed YdbK and knockout of aceE (ΔaceE), as compared to control. The control is the same strain without (ΔaceE). ΔaceE prevents PDH-mediated conversion of PYR to AcCoA.
Figure 16B:
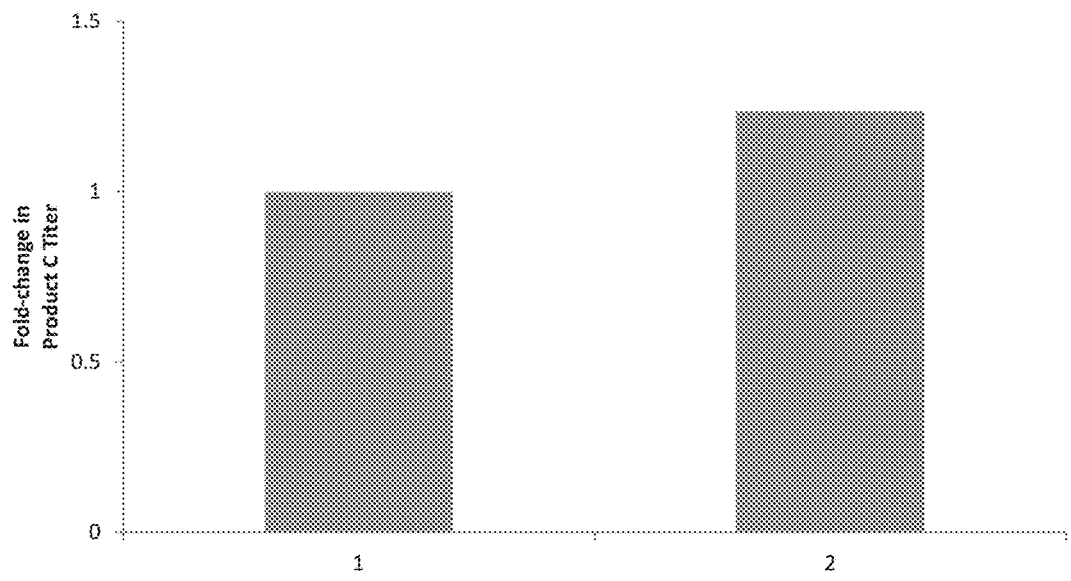
Figure 16C:
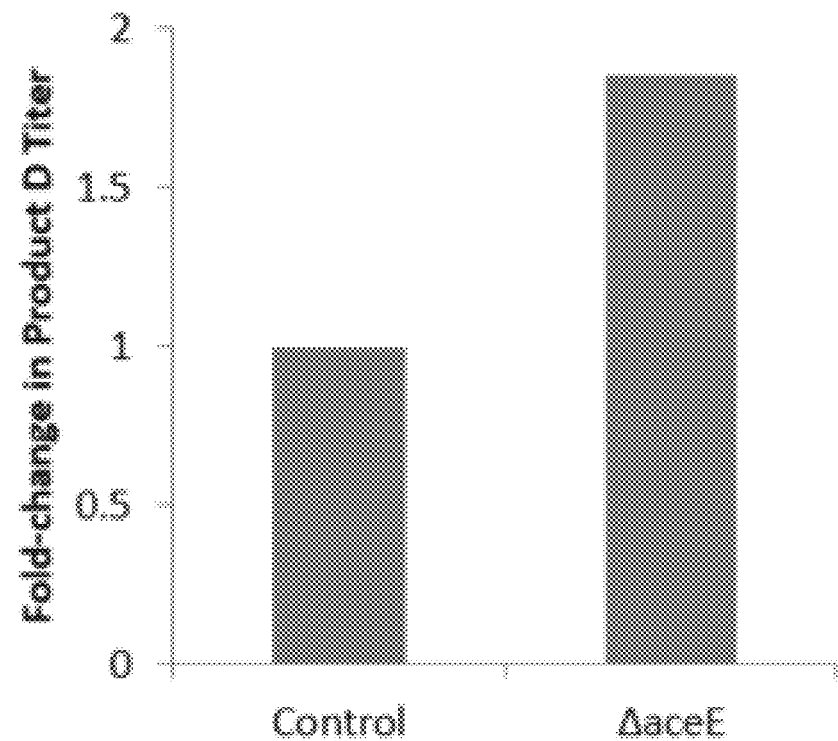
Figure 16D:
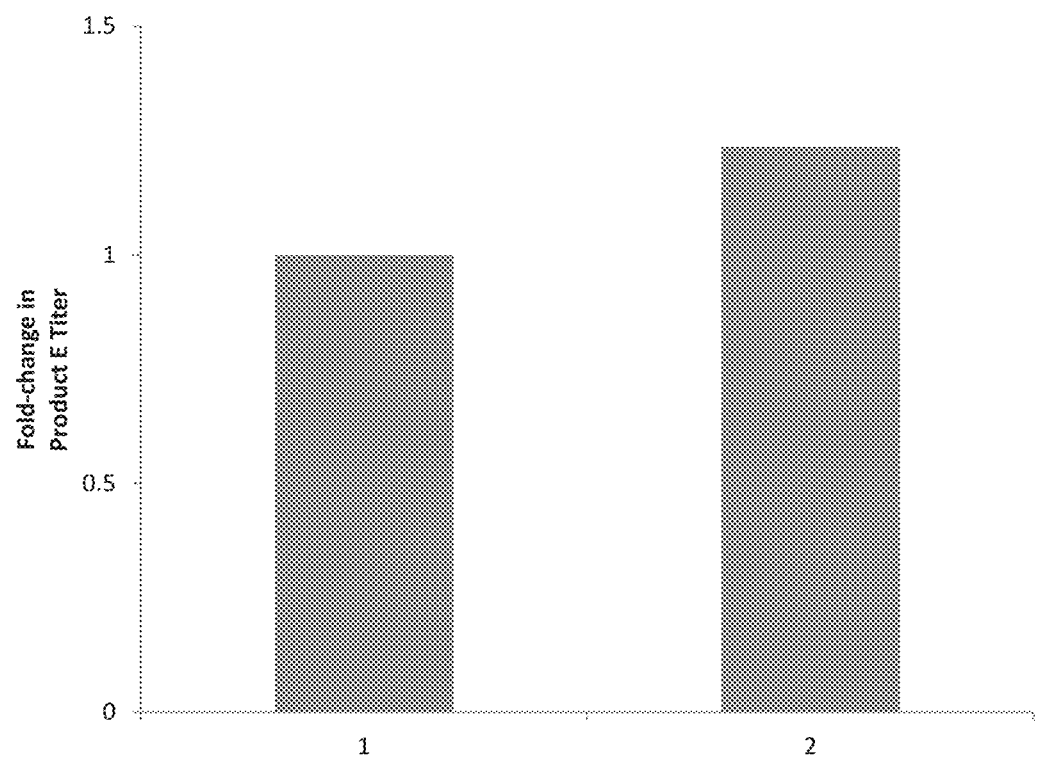
Figure 16E:
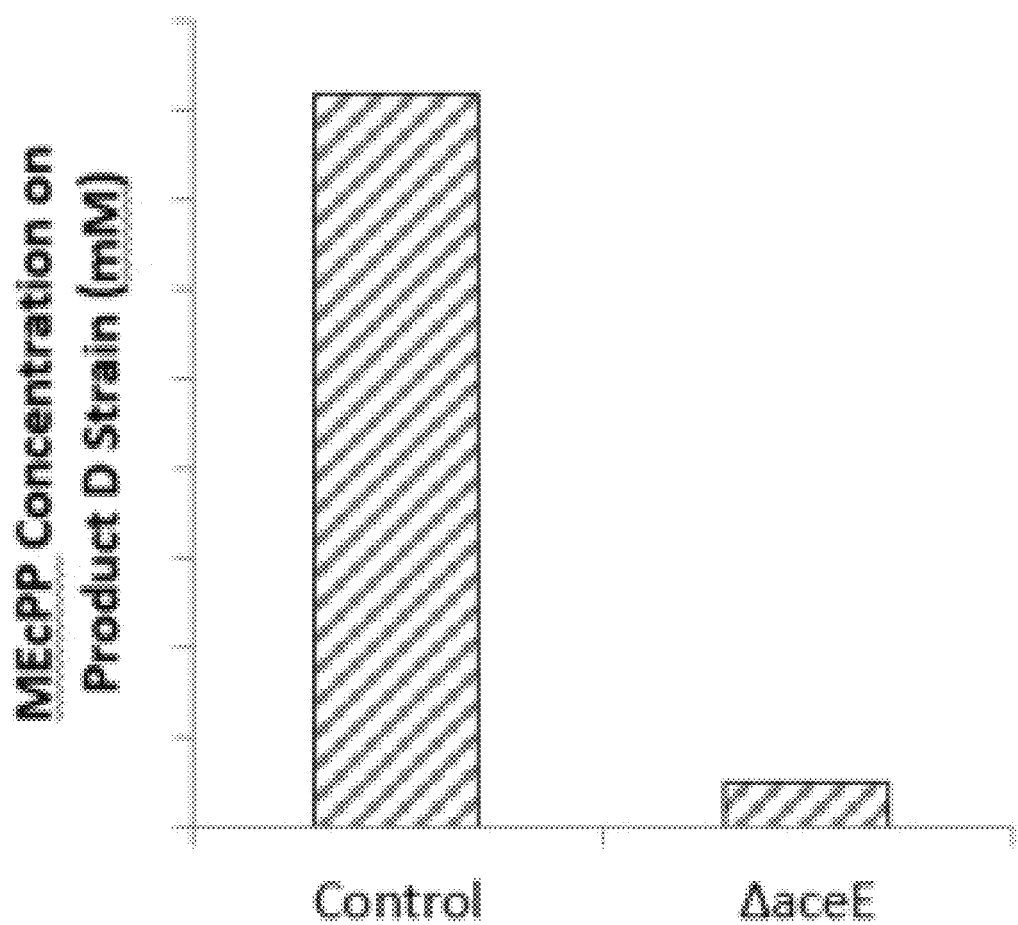
FIG. 16E is a graph showing that bacterial strains that produce terpenoid Product D, overexpress YdbK, and have ΔaceE show a reduction in extracellular MEcPP as compared to control (no ΔaceE).

The data also shows a reduction in MEcPP concentrations in the extracellular broth (FIG. 16E) as compared to control, which confirms that carbon flux has been pushed through the IspG/H steps into product. See FIG. 1.

Knockdown of PDH Via Mutated aceE

Three *E. coli* strains, each of which were engineered to produce three different terpenoid products (shown as Product B, Product C, and Product D) were further engineered to express a mutated aceE (G267C; aceE mut), which resulted in reducing PDH activity. Control strains were the same, but did not have a mutated aceE.

Figure 17A:
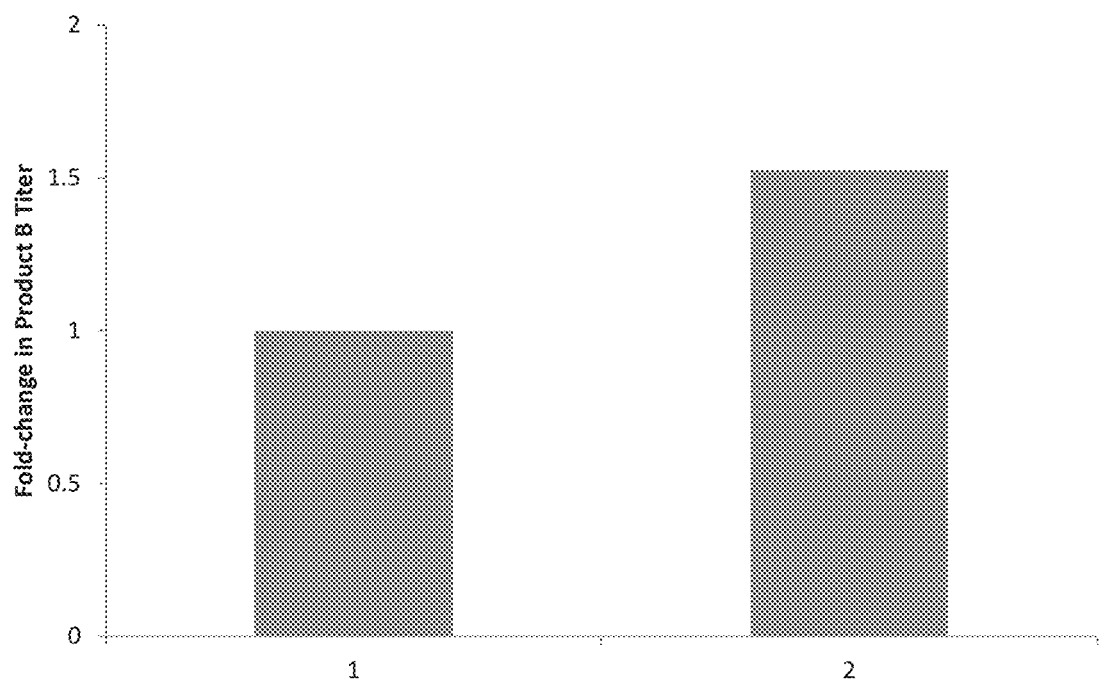
FIGS. 17A-C are graphs showing the fold change in terpenoid product in bacterial strains having overexpressed YdbK and mutated aceE (aceE mut), as compared to control (no aceE mut). aceE mut reduces PDH-mediated conversion of PYR to AcCoA.
Figure 17B:
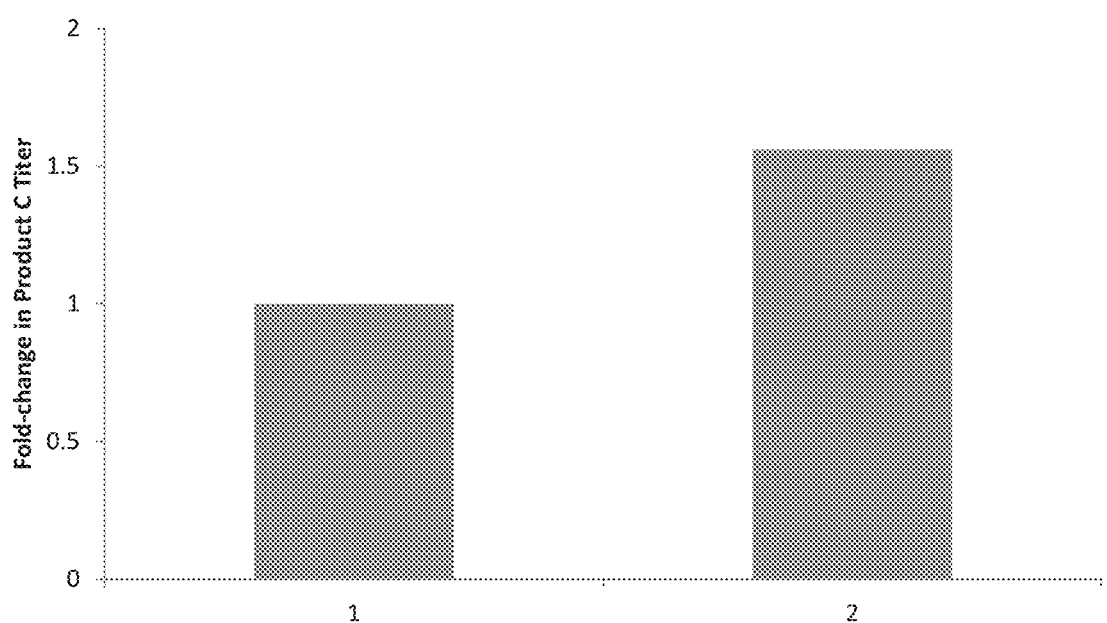
Figure 17C:
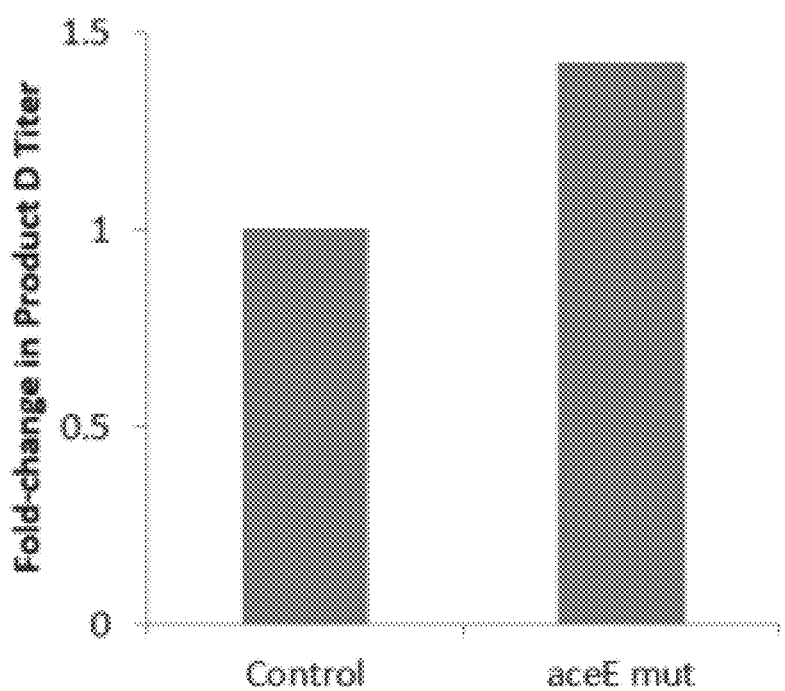

Similar to the aceE knockout results, the data shows an increase in titer of each of the three terpenoid products in the microbial strains expressing mutated aceE as compared to control. See FIGS. 17A-C.

Figure 17D:
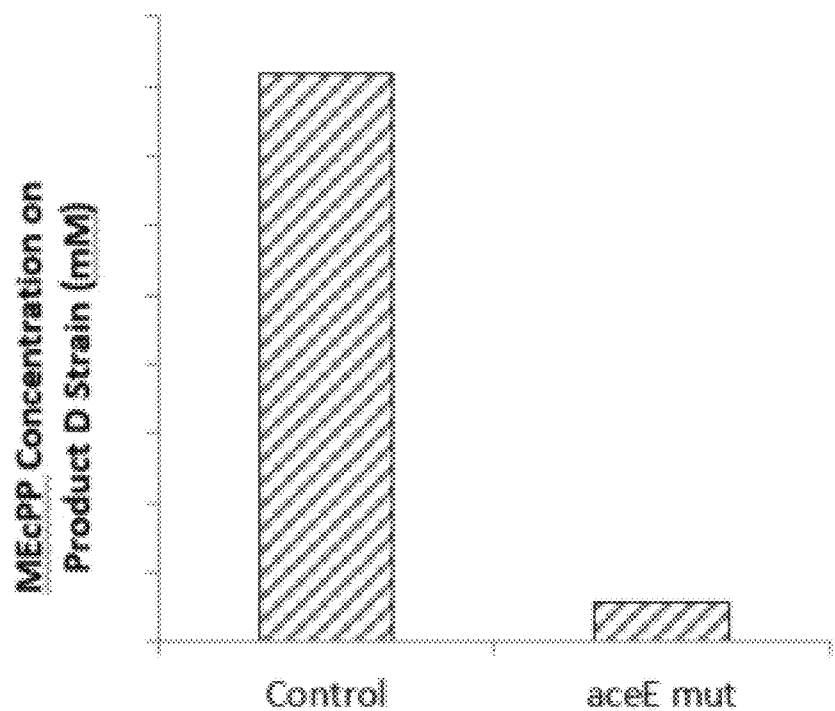
FIG. 17D is a graph showing that a bacterial strain that produces terpenoid Product D, overexpresses YdbK, and expresses an aceE mut has a reduction in extracellular MEcPP as compared to control (no aceE mut).
Figure 18:
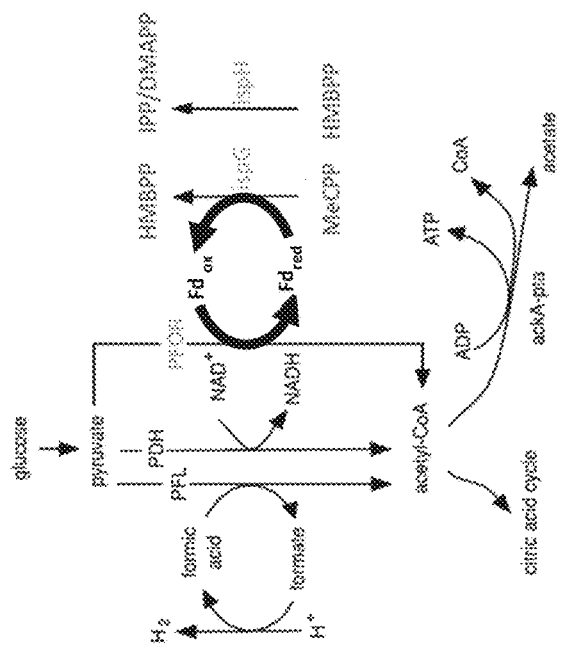
FIG. 18 is a diagram illustrating the three known reactions in *E. coli* to convert pyruvate (PYR) to acetyl-CoA (AcCoA) and illustrates how expressing fdx or fldA homologs can increase the electron supply to IspG and/or IspH through the Fd redox reaction (shown in bold).
Figure 18:
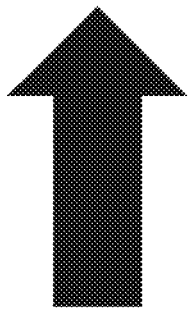
Figure 18:
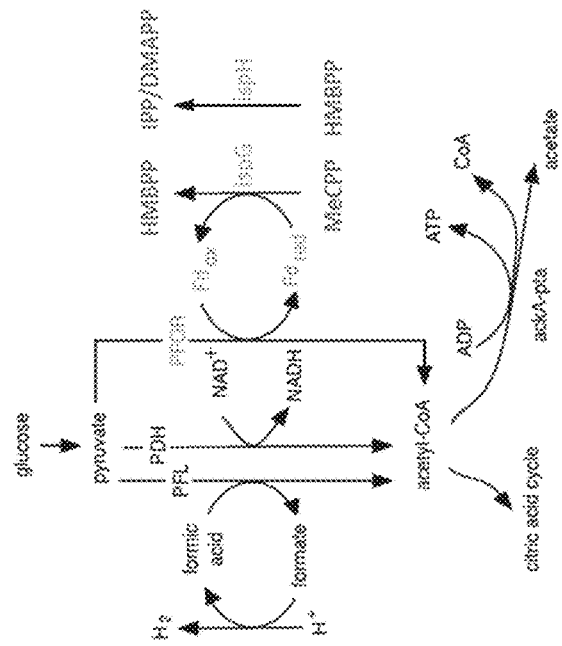

The data also shows a reduction in MEcPP concentrations in the extracellular broth (FIG. 17D) as compared to control, which confirms that carbon flux has been pushed through the IspG/H steps into product. See FIG. 1.

Example 6: Non-Native Electron Acceptors/Donors Increase YdbK-Dependent Isoprenoid Production When YdbK was overexpressed in *E. coli*, native ferredoxin (fdx) or flavodoxin (fldA) shuttled electrons to IspG and IspH (PYR/YdbK/fldA or fdx). *E. coli* engineered to produce Product B and overexpress YdbK was further engineered to overexpress one of the following fdx homologs in Table 5 or fldA homologs in Table 6. The first seven fdx homologs are 2[4Fe-4S] ferredoxins meaning they contain two 4Fe-4S iron-sulfur clusters that can have either the same or different redox potentials. For ferredoxin where the clusters differ in redox potential, given the redox potential of YdbK, we anticipate that in most cases cluster 1 will be the relevant cluster. The remaining fdx homologs are a 2Fe-2S ferredoxin and a high potential 4Fe-4S ferredoxin, both of which contain a single cluster. Control *E. coli* did not express any fdx or fldA homologs.

TABLE 5

Fdx Homologs

| fdx | Cluster 1 (mV) | Cluster 2 (mV) | Organism |
|---|---|---|---|
| Hm.fdx1 | −480 | −524 | *Heliobacterium modesticaldum* |
| Pa.fdx | −475 | −655 | *Pseudomonas aeruginosa* |
| Cv.fdx | −467 | −640 | *Allochromatium vinosum* |
| Cv.fdx_C57A | −451 | −590 | Synthetic |
| Ec.yfhL | −418 | −675 | *E. coli* |
| Ca.fdx | −400 | −400 | *Clostridium acetobutylicum* |
| Cp.fdx | −390 | −390 | *Clostridium pasteurianum* |
| Ev2.fdx | +50 | — | *Ectothiorhodospira shaposhnikovii* |
| Pp1.fdx | — | — | *Pseudomonas putida* |
| Pp2.fdx | — | — | *Pseudomonas putida* |

TABLE 6

FldA Homologs

| fldA | Semi-quinone->oxidized (mV) | Hydro-quinone->semiquinone (mV) | Organism |
|---|---|---|---|
| Ac.fldA2 | −522 | −133 | *Azotobacter chroococcum* |
| Av.fldA2 | −483 | −187 | *Azotobacter vinelandii* |
| Ec.fldA | −433 | −254 | *E. coli* |
| Bs.fldA | −382 | −105 | *B. subtilis* |

Figure 19A:
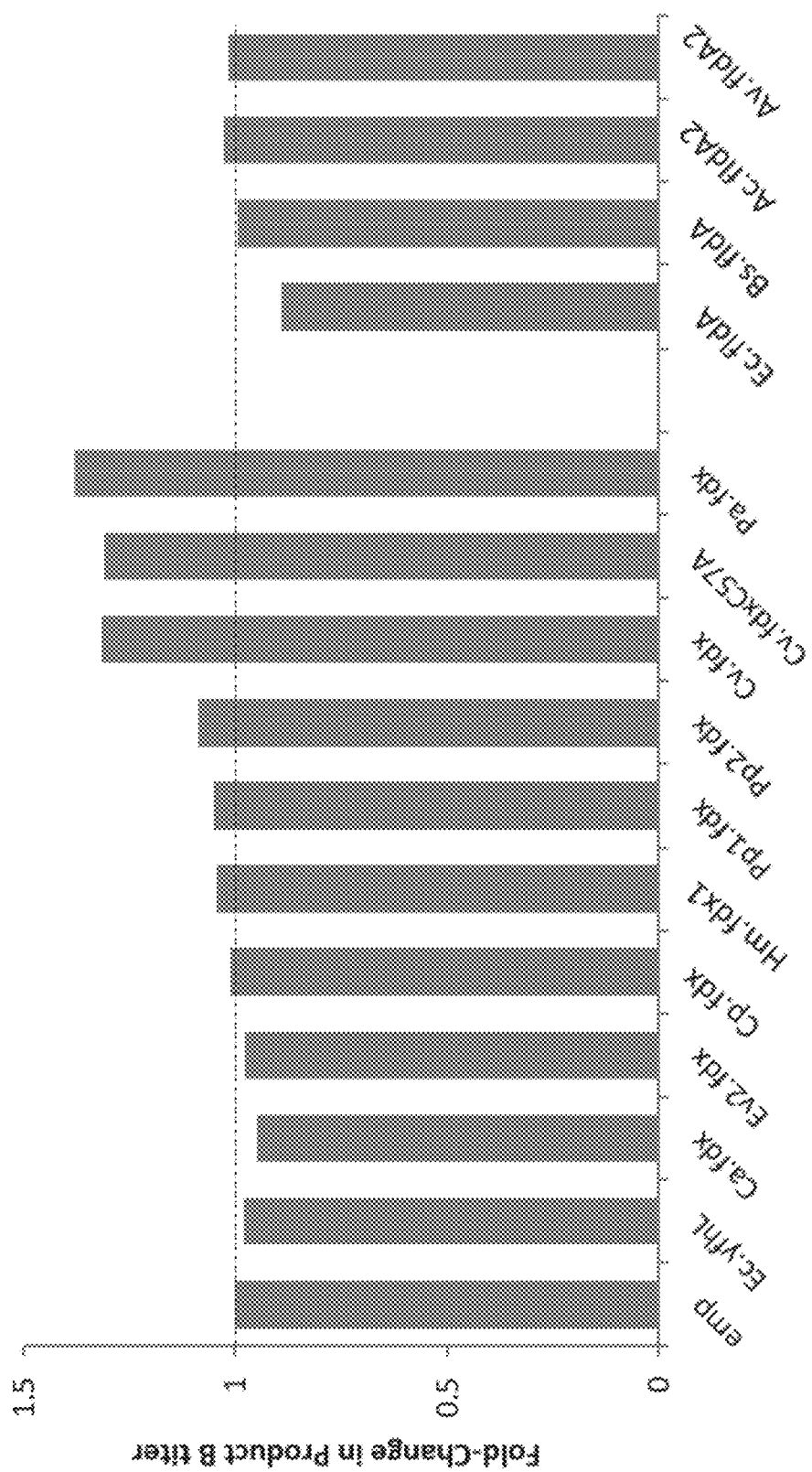
FIG. 19A is a graph showing the fold change (as compared to the empty vector control (emp)) of terpenoid Product B production in a bacterial strain engineered to overexpress YdbK and overexpress an fdx or fldA homolog.

The data shows that overexpression of certain fdx or fldA homologs in *E. coli* and overexpress YdbK had increased titers of terpenoid product (Product B in this example) as compared to the empty vector control (emp) (e.g., H.fdx, Cv.fdx, Cv.fdxC57A, and Pa.fdx). FIG. 19A.

Figure 19B:
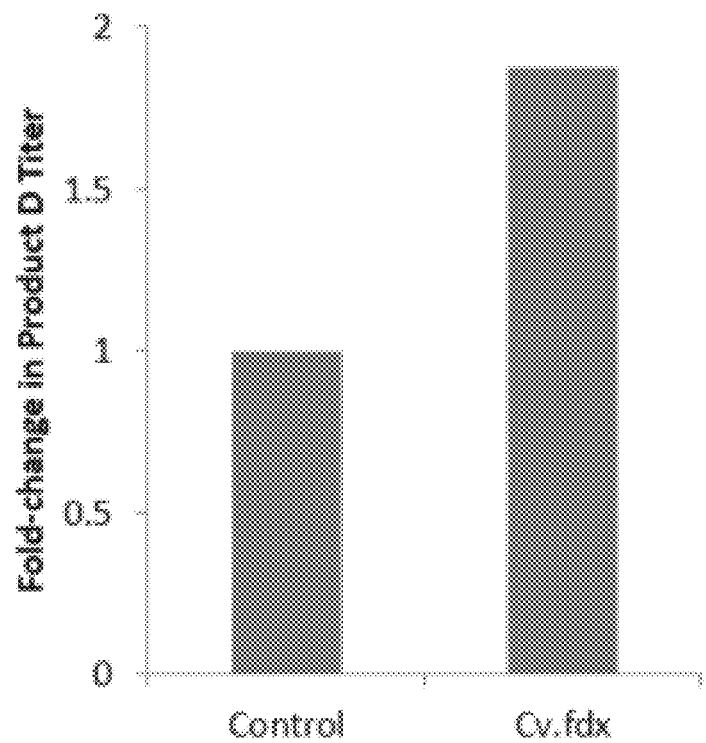
FIG. 19B is a graph showing the fold change (as compared to control) of terpenoid Product D in a bacterial strain engineered to overexpress YdbK and Cv.fdx (an fdx homolog from *Allochromatium vinosum*).
Figure 19C:
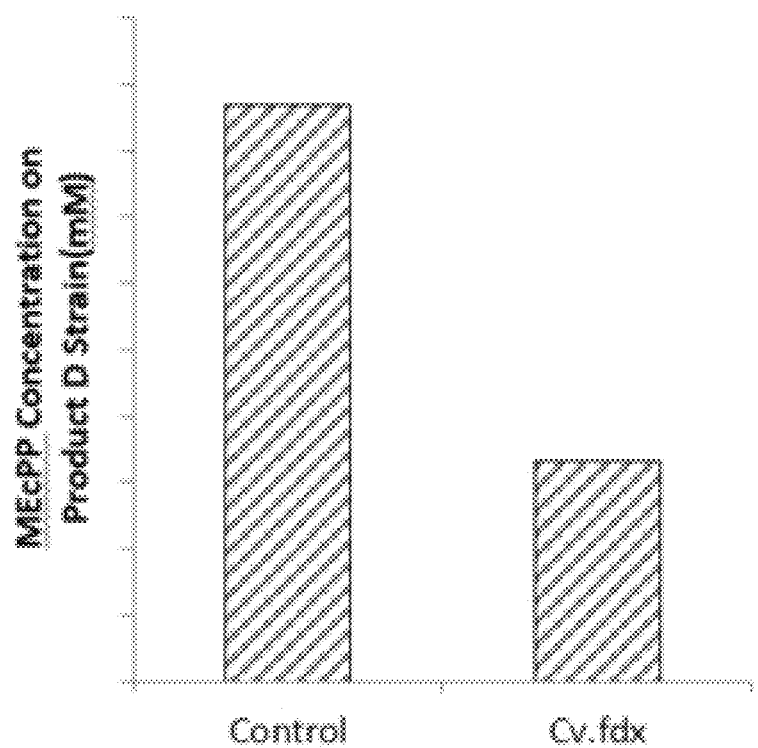
FIG. 19C is a graph showing that a bacterial strain that produces terpenoid Product D and overexpresses YdbK and Cv.fdx has a reduction in extracellular MEcPP as compared to control (without overexpression of Cv.fdx).

*E. coli* engineered to produce Product D and overexpress YdbK were further engineered to overexpress Cv.fdx. Similar to the previous results, the data shows that overexpression of Cv.fdx in *E. coli* engineered to produce a terpenoid product (Product D in this example) and overexpress YdbK had increased titers of terpenoid product as compared to control. FIG. 19B. Additionally, the data shows a reduction in MEcPP concentrations in the extracellular broth (FIG. 19C) as compared to control, which confirms that carbon flux has been pushed through the IspG/H steps into product. See FIG. 1.

Example 7: Overexpression or Complementation with PFOR Homologs, for Homologs, and/or Fdx or fldA Homologs

*E. coli* engineered to produce Product F were further engineered to overexpress at least one PFOR homologs or fpr homologs and, optionally, a fdx or fldA homolog as shown in Table 7.

TABLE 7

| Group | Homolog | SEQ ID NO(s) |
|---|---|---|
| 1 | Scy.pfor (*Synechocystis* sp.) | SEQ ID NO: 29 |
| 2 | Ki.pfor (*Kluyvera intermedia*) | SEQ ID NO: 30 |
| 3 | Da.pfor (*Desulfovibrio africanus*) | SEQ ID NO: 31 |
| 4 | Sco.pfor (*Synechococcus* sp.) | — |
| 5 | Ec.ydhV and Ec.ydhY (*E. Coli*) | SEQ ID NO: 33 and SEQ ID NO: 34 |
| 6 | Ga.pfor (*Gilliamella apicola*) | SEQ ID NO: 35 |
| 7 | Ec.ydbK (*E. Coli*) | SEQ ID NO: 9 |
| 8 | Ec.ydbK and Cp.fdx (*E. Coli* and *C. pasteurianum*) | SEQ ID NO: 9 and 10 |
| 9 | Ns.fpr (*Nostoc* sp.) | SEQ ID NO: 36 |
| 10 | Sco.fpr (*Synechococcus* sp.) | SEQ ID NO: 37 |
| 11 | Ec.fpr and Ec.fdx (*E. Coli*) | SEQ ID NO: 38 and SEQ ID NO: 21 |
| 12 | Ec.fpr and Ec.fldA (*E. Coli*) | SEQ ID NO: 38 and SEQ ID NO: 27 |

Figure 20:
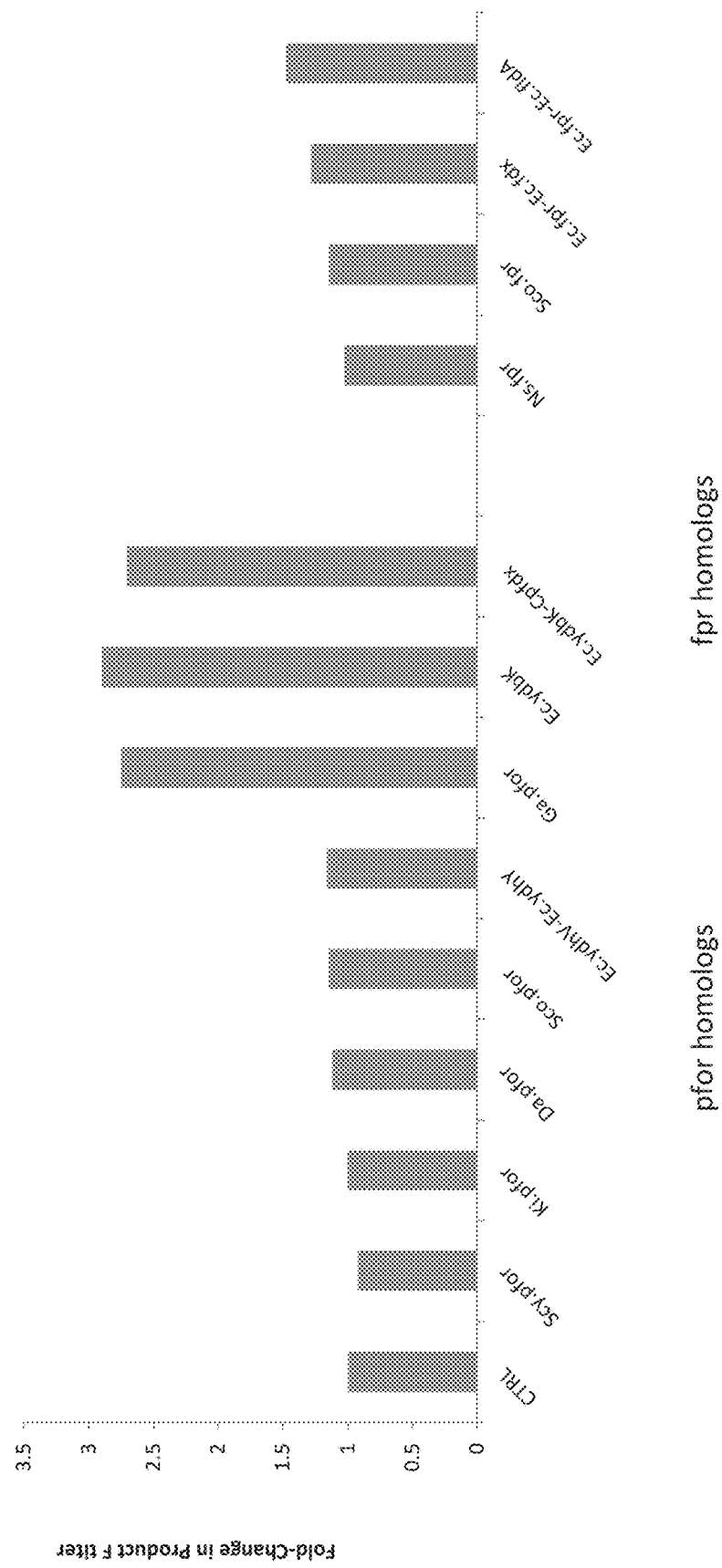
FIG. 20 is a graph showing the fold change in the production of terpenoid product in bacterial strains that produce terpenoid Product F and which overexpress one or more PFOR or fpr homologs and, optionally, a fdx or fldA homolog.

The data shows that some bacterial strains engineered to express PFOR and fpr homologs had increased titers of terpenoid product (Product F in this example) as compared to empty vector control (CTRL) (e.g., Da.pfor (*Desulfovibrio africanus*) (SEQ ID NO: 31); Sco.pfor (*Synechococcus* sp.); Ga.pfor (*Gilliamella apicola*) (SEQ ID NO: 35); Ec.ydbk (*E. Coli*) (SEQ ID NO: 9); and Sco.fpr (*Synechococcus* sp.) (SEQ ID NO: 37). See FIG. 20.

The data also shows that bacterial strains engineered to overexpress at least one PFOR homolog and a fdx had increased titers of terpenoid product (Product F) as compare to empty vector control (CTRL) (e.g., Ec.ydhV/Ec.ydhY; *E. coli* (SEQ ID NO: 33 and SEQ ID NO: 34, respectively) and Ec.ydbKlCp.fdx; *E. coli* (SEQ ID NO: 9 and 10, respectively)). See FIG. 20.

Additionally, the data shows that bacterial strains engineered to overexpress at least one fpr homologs and either fdx or fldA had increased titers of terpenoid product (Product F) as compare to empty vector control (CTRL) (e.g., Ec.fpr/Ec.fdx; *E. coli* (SEQ ID NO: 38 and SEQ ID NO: 21, respectively) and Ec.fpr/Ec.fldA; *E. coli* (SEQ ID NO: 38 and SEQ ID NO: 27, respectively)). See FIG. 20.

SEQUENCES

SEQ ID NO: 1 (*E. coli* IspG)

MHNQAPIQRRKSTRIYVGNVPIGDGAPIAVQSMTNTRTTDVEATVNQIKALERVG
ADIVRVSVPTMDAAEAFKLIKQQVNVPLVADIHFDYRIALKVAEYGVDCLRINPG
NIGNEERIRMVVDCARDKNIPIRIGVNAGSLEKDLQEKYGEPTPQALLESAMRHVD
HLDRLNFDQFKVSVKASDVFLAVESYRLLAKQIDQPLHLGITEAGGARSGAVKSAI
GLGLLLSEGIGDTLRVSLAADPVEEIKVGFDILKSLRIRSRGINFIACPTCSRQEFDVI
GTVNALEQRLEDIITPMDVSIIGCVVNGPGEALVSTLGVTGGNKKSGLYEDGVRK
DRLDNNDMIDQLEARIRAKASQLDEARRIDVQQVEK

| SEQUENCES |
| --- |

SEQ ID NO: 2 (*E. coli* IspH)
MQILLANPRGFCAGVDRAISIVENALAIYGAPIYVRHEVVHNRYVVDSLRERGAIFI
EQISEVPDGAILIFSAHGVSQAVRNEAKSRDLTVFDATCPLVTKVHMEVARASRRG-
EESILIGHAGHPEVEGTMGQYSNPEGGMYLVESPDDVWKLTVKNEEKLSFMTQTT
LSVDDTSDVIDALRKRFPKIVGPRKDDICYATTNRQEAVRALAEQAEVVLVVGSK
NSSSNSNRLAELAQRMGKRAFLIDDAKDIQEEWVKEVKCVGVTAGASAPDILVQN
VVARLQQLGGGEAIPLEGREENIVFEVPKELRVDIREVD SEQ ID NO: 3 (*E. coli* Dxs)
MSFDIAKYPTLALVDSTQELRLLPKESLPKLCDELRRYLLDSVSRSSGHFASGLGT
VELTVALHYVYNTPFDQLIWDVGHQAYPHKILTGRRDKIGTIRQKGGLHPFPWRG
ESEYDVLSVGHSSTSISAGIGIAVAAEKEGKNRRTVCVIGDGAITAGMAFEAMNHA
GDIRPDMLVILNDNEMSISENVGALNNHLAQLLSGKLYSSLREGGKKVFSGVPPIK
ELLKRTEEHIKGMVVPGTLFEELGFNYIGPVDGHDVLGLITTLKNMRDLKGPQFLH
IMTKKGRGYEPAEKDPITFHAVPKFDPSSGCLPKSSGGLPSYSKIFGDWLCETAAK
DNKLMAITPAMREGSGMVEFSRKFPDRYFDVAIAEQHAVTFAAGLAIGGYKPIVAI
YSTFLQRAYDQVLHDVAIQKLPVLFAIDRAGIVGADGQTHQGAFDLSYLRCIPEM
VIMTPSDENECRQMLYTGYHYNDGPSAVRYPRGNAVGVELTPLEKLPIGKGIVKR
RGEKLAILNFGTLMPEAAKVAESLNATLVDMRFVKPLDEALILEMAASHEALVTV
EENAIMGGAGSGVNEVLMAHRKPVPVLNIGLPDFFIPQGTQEEMRAELGLDAAG
MEAKIKAWLA SEQ ID NO: 4 (*E. coli* Dxr)
MKQLTILGSTGSIGCSTLDVVRHNPEHFRVVALVAGKNVTRMVEQCLEFSPRYAV
MDDEASAKLLKTMLQQQGSRTEVLSGQQAACDMAALEDVDQVMAAIVGAAGL
LPTLAAIRAGKTILLANKESLVTCGRLFMDAVKQSKAQLLPVDSEHNAIFQSLPQPI
QHNLGYADLEQNGVVSILLTGSGGPFRETPLRDLATMTPDQACRHPNWSMGRKIS
VDSATMMNKGLEYIEARWLFNASASQMEVLIHPQSVIHSMVRYQDGSVLAQLGE
PDMRTPIAHTMAWPNRVNSGVKPLDFCKLSALTFAAPDYDRYPCLKLAMEAFEQ
GQAATTALNAANEITVAAFLAQQIRIFTDIAALNLSVLEKMDMREPQCVDDVLSVD
ANAREVARKEVMRLAS SEQ ID NO: 5 (*E. coli* IspD)
MATTHLDVCAVVPAAGFGRRMQTECPKQYLSIGNQTILEHSVHALLAHPRVKRV
VIAISPGDSRFAQLPLANHPQITVVDGGDERADSVLAGLKAAGDAQWVLVHDAA
RPCLHQDDLARLLALSETSRTGGILAAPVRDTMKRAEPGKNAIAHTVDRNGLWH
ALTPQFFPRELLHDCLTRALNEGATITDEASALEYCGFHPQLVEGRADNIKVTRPE
DLALAEFYLTRTIHQENT SEQ ID NO: 6 (*E. coli* IspE)
MRTQWPSPAKLNLFLYITGQRADGYHTQTLFQFLDYGDTISIELRDDGDIRLLTP
VEGVEHEDNLIVRAARLLMKTAADSGRLPTGSGANISIDKRLPMGGGLGGGSSNA
ATVLVALNHLWQCGLSMDELAEMGLTLGADVPVFVRGHAAFAEGVGEILTPVDP
PEKWYLVAHPGVSIPTPVIFKDPELPRNTPKRSIETLLKCEFSNDCEVIARKRFREVD
AVLSWLLEYAPSRLTGTGACVFAEFDTESEARQVLEQAPEWLNGFVAKGANLSPL
HRAML SEQ ID NO: 7 (*E. coli* IspF)
MRIGHGFDVAFGGEGPIIIGGVRIPYEKGLLAHSDGDVALHALTDALLGAAALG
DIGKLFPDTDPAFKGADSRELLREAWRRIQAKGYTLGNVDVTIIAQAPKMLPHIPQ
MRVFIAEDLGCHMDDVNVKATTTEKLGFTGRGEGIACEAVALLIKATK SEQ ID NO: 8 (*E. coli* Idi)
MQTEHVILLNAQGVPTGTLEKYAAHTADTRLHLAFSSWLFNAKGQLLVTRRALS
KKAWPGVWTNSVCGHPQLGESNEDAVIRRCRYELGVEITPPESIYPDFRYRATDPS
GIVENEVCPVFAARTTSALQINDDEVMDYQWCDLADVLHGIDATPWAFSPWMV
MQATNREARKRLSAFTQLK SEQ ID NO: 9 (*E. coli* YdbK)
MITIDGNGAVASVAFRTSEVIAIYPITPSSTMAEQADAWAGNGLKNVWGDTPRVV
EMQSEAGAIATVHGALQTGALSTSFTSSQGLLLMIPTLYKLAGELTPFVLVHVAART
VATHALSIFGDHSDVMAVRQTGCAMLCAANVQEAQDFALISQIATLKSRVPFIHFF
DGFRTSHEINKIVPLADDTILDLMPQVEIDAHRARALNPEHPVIRGTSANPDTYFQS
REATNPWYNAVYDHVEQAMNDFSAATGRQYQPFEYYGHPQAERVIILMGSAIGT
CEEVVDELLTRGEKVGNVKVRLYRPFSAKHLLQALPGSVRSVAVLDRTKEPGAQA
EPLYLDVMTALAEAFNNGERETLPRVIGGRYGLSSKEFGPDCVLACFAELNAAKP
KARFTVGIYDDVTNLSLPLPENTLPNSAKLEALFYGLGSDGSVSATKNNIKIIGNST
PWYAQGYFVYDSKKAGGLTVSHLRVSEQPIRSAYLISQADFVGCHQLQFIDKYQM
AERLKPGGIFLLNTPYSADEVWSRLPQEVQAVLNQKKARFYVINAAKIARECGLA
ARINTVMQMAFFHLTQILPGDSALAELQGAIAKSYSSKGQDLVERNWQALALARE
SVEEVPLQPVNPHSANRPPVVSDAAPDFVKTVTAAMLAGLGDALPVSALPPDGT
WPMGTTRWEKRNIAEEIPIWKEELCTQCNHCVAACPHSAIRAKVVPPEAMENAPA
SLHSLDVKSRDMRGQKYVLQVAPEDCTGCNLCVEVCPAKDRQNPEIKAINMMSR
LEHVEEEKINYDFFLNLPEIDRSKLERIDIRTSQLITPLFEYSGACSGCGETPYIKLLT
QLYGDRMLIANATGCSSIYGGNLPSTPYTTDANGRGPAWANSLFEDNAEFGLGFR
LTVDQHRVRVLRLLDQFADKIPAELLTALKSDATPEVRREQVAALRQQLNDVAEA

|     SEQUENCES     |
|---|

HELLRDADALVEKSIWLIGGDGWAYDIGFGGLDHVLSLTENVNILVLDTQCYSNT
GGQASKATPLGAVTKFGEHGKRKARKDLGVSMMMYGHVYVAQISLGAQLNQTV
KAIQEAEAYPGPSLIIAYSPCEEHGYDLALSHDQMRQLTATGFWPLYRFDPRRADE
GKLPLALDSRPPSEAPEETLLHEQRFRRLNSQQPEVAEQLWKDAAADLQKRYDFL
AQMAGKAEKSNTD

SEQ ID NO: 10 (*Clostridium pasteurianum* fdx; Cp.fdx)
MAYKIADSCVSCGACASECPVNAISQGDSIFVIDADTCIDCGNCANVCPVGAPVQE SEQ ID NO: 11 (*E. coli* PgpB)
MRSIARRTAVGAALLLVMPVAVWISGWRWQPGEQSWLLKAAFWVTETVTQPWG
VITHLILFGWFLWCLRFRIKAAFVLFAILAAAILVGQGVKSWIKDKVQEPRPFVIWL
EKTHHIPVDEFYTLKRAERGNLVKEQLAEEKNIPQYLRSHWQKETGFAFPSGHTM
FAASWALLAVGLLWPRRRTLTIAILLVWATGVMGSRLLLGMHWPRDLVVATLIS
WALVAVATWLAQRICGPLTPPAEENREIAQREQES SEQ ID NO: 12 (*E. coli* NudB)
MKDKVYKRPVSILVVIYAQDTKRVLMLQRRDDPDFWQSVTGSVEEGETAPQAAM
REVKEEVTIDVVAEQLTLIDCQRTVEFEIFSHLRHRYAPGVTRNTESWFCLALPHE
RQIVFTEHLAYKWLDAPAAAALTKSWSNRQAIEQFVINAA SEQ ID NO: 13 (*E. coli* Shine Dalgarno sequence)
AGGAGG SEQ ID NO: 14 (*Methanococcus maripaludis* GAPOR)
MNILIDGSRQNYEELEESEFPISFGINLHTKQETWKYDAFDEKNLFCFGKGILPIIGG
HRLIFSFRSPLWDGFHFSAMGGAGYTFKDTGIQNVAITGKCEVPTVIVLNGEEDKL
KIEFMPFTEEITDIYEFNDKIIDLFKEKNYRAFLVGPASKTTNMGGIYSQTIRNGKIV
EGSEDWAARGGGGSVLYQAHNVLGVVFFGKKTPEKNLKEIVEEHYNKPYTKVVL
EHTEKYRYSEEKKTGGTFGNNYHVTMELTPVFNWRMPFIDKNKRMKLHKKIIEYF
VNRFDEEAIETKNWTNCGEPCPVVCKKYRKGLHVDYEPYEANGPCIGVFDIYAAD
KVVHTIDKLGFDAIEFGNLCSWTFELLDNGMLKPEEVGIEKPVFDISNFENDEDILK
NSMHNAEQAVKLAEIIAFQTNEFGKICKSGTRRAGKILNEKYPDRIKDKKFEDFGV
YDSFGERGQISPTMYWAIGNFMPYLIQGKYLTHYQCGVFLEPEELAELSVKNSIEEI
TLENLGICRFHRKWVTPIIEKLVKEMSDVNLNEESMELFKKIAKYDSNIGCPEMES
ERVKELIIAGAFEFENEKWSKEFENGNFDEYIKRVLEKYSELLEIDWKLKE SEQ ID NO: 15 (*Heliobacterium modesticaldum*, Hm.fdx1)
MAYKITDACTACGACMDGCCVGAIVEGKKYSITSDCVDCGVCADKCPVDAIIPG SEQ ID NO: 16 (*Pseudomonas aeruginosa*, Pa.fdx)
MSLKITDDCINCDVCEPECPNGAISQGEEIYVIDPNLCTECVGHYDEPQCQQVCPV
DCIPLDDANVESKDQLMEKYRKITGKA SEQ ID NO: 17 (*Allochromatium vinosum*, Cv.fdx)
MALMITDECINCDVCEPECPNGAISQGDETYVIEPSLCTECVGHYETSQCVEVCPV
DCIIKDPSHEETEDELRAKYERITGEG SEQ ID NO: 18 (Cv.fdx_C57A)
MALMITDECINCDVCEPECPNGAISQGDETYVIEPSLCTECVGHYTTSQCVEVCPV
DAIIKDPSHEETEDELRAKYERITGEG SEQ ID NO; 19 (*E. coli*, Ec.yfhL)
MALLITKKCINCDMCEPECPNEAISMGDHIYEINSDKCTECVGHYETPTCQKVCPIP
NTIVKDPAHVETEEQLWDKFVLMHHADKI SEQ ID NO: 20 (*Clostridium acetobutylicum*, Ca.fdx)
MAYKITDACVSCGSCASECPVSAISQGDTQFVIDADTCIECGNCANVCPVGAPVQE SEQ ID NO: 21 (E. coli, Ec.fdx)
MPKIVILPHQDLCPDGAVLEANSGETILDAALRNGIEIEHACEKSCACTTCHCIVRE
GFDSLPESSEQEDDMLDKAWGLEPESRLSCQARVTDEDLVVEIPRYTINHAREH SEQ ID NO: 22 (*Ectothiorhodospira shaposhnikovii*, Ev2.fdx)
MERLSEDDPAAQALEYRHDASSVQHPAYEEGQTCLNCLLYTDASAQDWGPCSVF
PGKLVSANGWCTAWVAR SEQ ID NO: 23 (*Pseudomonas putida*, Pp1.fdx)
MSLIITDDCINCDVCEPECPNAAISQGEEIYVIDPNLCTQCVGHYDEPQCQQVCPVD
CIPLDEAHPETHDELMEKYKRITGKA SEQ ID NO: 24 (Pseudomonas putida, Pp2.fdx)
MSLIITDDCINCDVCEPECPNEAISQGEEIYVDPNLCTQCVGHYDEPQCQQVCPVD
CIPLDEAHPETEEELMAKYRRIT

SEQUENCES

SEQ ID NO: 25 (*Azotobacter vinelandii* fldA2; Av.fldA2)
MAKIGLFFGSNTGKTRKVAKSIKKIRFDDETMSDALNVNRVSAEDFAQYQFLILGT
PTLGEGELPGLSSDCENESWEEFLPKIEGLDFSGKTVALFGLGDQVGYPENYLDAL
GELYSFFKDRGAKIVGSWSTDGYEFESSEAVVDGKFVGLALDLDNQSGKTDERVA
AWLAQIAPEFGLSL SEQ ID NO: 26 (*Azotobacter chroococcum* fldA2; Ac.fldA2)
MAKIGLFFGSNTGKTRKVAKSIKKRFDDETMSDAVNVNRVSAEDFAQYQFLILGT
PTLGEGELPGLSSDCENESWEEFLPKIEGLDFSGKTVALFGLGDQVGYPENFLDAM
GELHSFFTERGAKVVGAWSTDGYEFEGSTAVVDGKFVGLALDLDNQSGKTDERV
AAWLAQIAPEFGLSL SEQ ID NO: 27 (*E. coli*, Ec.fldA)
MAITGIFFGSDTGNTENIAKMIQKQLGKDVADVHDIAKSSKEDLEAYDILLLGIPT
WYYGEAQCDWDDFFPTLEEIDFNGKLVALFGCGDQEDYAEYFCDALGTIRDIIEPR
GATIVGHWPTAGYHFEASKGLADDDHFVGLAIDEDRQPELTAERVEKWVKQISEE
LHLDEILNA SEQ ID NO: 28 (*B. subtilis*, Bs.fldA)
MAKALITYASMSGNTEDIAFIIKDTLQEYELDIDCVEINDMDASCLTSYDYVLIGTY
TWGDGDLPYEAEDFFEEVKQIQLNGLKTACFGSGDYSYPKFCEAVNLFNVMLQE
AGAAVYQETLKIELAPETDEDVESCRAFARGFLAWADYMNKEKIHVS SEQ ID NO: 29 (*Synechocystis* sp., Scy.pfor)
MSLPTYATLDGNEAVARVAYLLSEVIAIYPITPSSPMGEWSDAWAAEHRPNLWGT
VPLVVEMQSEGGAAGTVHGALQSGALTTTFTASQGLMLMLPNMHKIAGELTAM
VLHVAARSLAAQGLSIFGDHSDVMAARNTGFAMLSSNSVQEAHDFALIATATSFA
TRIPGLHFFDGFRTSHEEQKIELLPQEVLRGLIKDEDVLAHRGRALTPDRPKLRGTA
QNPDVYFQARETVNPFYASYPNVLEQVMEQFGQLTGRHYRPYEYCGHPEAERVI
VLMGSGAETAQEVTDFLTAQGEKVGLLKVRLYRPFAGDRLVNALPKTVQKIAVL
DRCKEPGSIGEPLYQDVLTAFFEAGMMPKIIGGRYGLSSKEFTPAMVKGVLDHLN
QTNPKNHFTVGINDDLSHTSIDYDPSFSTEADSVVRAIFYGLGSDGTVGANKNSIKI
IGEDTDNYAQGYFVYDSKKSGSVTVSHLRFGPNPILSTYLISQANFVACHQWEFLE
QFEVLEPAVDGGVFLVNSPYGPEEIWREFPRKVQQEIIDKNLKVYTINANDVARDA
GMGRRTNTVMQTCFFALAGVLPREEAIAKIKQSVQKTYGKKGQEIVEMNIKAVDS
TLAHLYEVSVPETVSDDAPAMRPVVPDNAPVFVREVLGKIMARQGDDLPVSALPC
DGTYPTATTQWEKRNVGHEIPVWDPDVCVQCGKCKCVIVCPHAVIRGKVYEEAELA
NAPVSFKFTNAKDHDWQGSKFTIQVAPEDCTGCGICVDVCPAKNKSQPRLRAINM
APQLPLREQERENWDFFLDLPNPDRLSLNLNKISHQQMQEPLFEFSGACAGCGETP
YLKLVSQLFGDRMLVANATGCSSIYGGNLPTTPWAQNAEGRGPAWSNSLFEDNA
EFGLGFRVAIDKQTEFAGELLKTFAGELGDSLVSEILNNAQTTEADIFEQRQLVEQ
VKQRLQNLETPQAQMFLSVADYLVKKSVWIIGGDGWAYDIGYGGLDHVLASGR
NVNILVMDTEVYSNTGGQASKATPRAAVAKFAAGGKPSPKKDLGLMAMTYGNV
YVASIAMGAKNEQSIKAFMEAEAYPGVSLIIAYSHCIAHGINMTTAMNHQKELVD
SGRWLLYRYNPLLADEGKNPLQLDMGSPKVAIDKTVYSENRFAMLTRSQPEEAK
RLMKLAQGDVNTRWAMYEYLAKRSLGGEINGNNHGVSPSPEVIAKSV SEQ ID NO: 30 (*Kluyvera intermedia*, Ki.pfor)
MSGKMKTMDGNAAAAWISYAFTDVAAIYPITPSTPMAENVDEWTAQGKKNLFG
QPVRLMEMQSEAGAAGAVHGALQAGALTTTYTASQGLLLMIPNLYKIAGELLPG
VFHVSARALATNSLNIFGDHQDVMAVRQTGCAMLAENNVQQVMDLSAVAHLSA
IKGRVPFINFFDGFRTSHEIQKIEVLEHEALAPLLDQEALNLFRRNALNPDHPVIRGT
AQNPDIYFQEREASNRFYQALPDIVEGYMAEIYRITGREYHLFDYYGSPDAEQIIIA
MGSVCDTIQEVVDAMIDSGEKVGLVSVHLFRPFSLAHFMAKIPASVKRIAVLDRT
KEPGAQAEPLCLDVKNAFYHHDNPPLIVGGRYALGGKDVLPGHIVSVNFENLKKPL
PMDGFTVGIFDDVTHTSLPVPAYDIHVSREGITACKFWGLGSDGTVSANKNAIKIIG
DNTSMFAQAYFAYDSKKSGGITMSHLRFGKRPITSPYLIHNADFIACSQQSYVDKY
DLLDGINPGGIFLLNCTWFGEEVERHLPNKMKRIIARQGVRFYTLNAVDIARKLGL
GGRFNMLMQAAFFKLTDIIDAKTASEHLKKAVAKSYGSKGQNVVDMNNAAIDLG
MDALQEIIVPDHWAYVEEEANNDGKLMPDFIRNILEPMNRQNGDKLPVSAFLGME
DGTFPPGTAAWEKRGIAMQVPVWQPEGCTQCNQCAFICPHAAIRPALLSSEEREA
APVALLSKVAQGAKHYEYHLAVSPLDCSGCGNCVDICPSKGKALAMKPLDSQRH
MVPVWDHALALAPKENPFSKATVKGCQFEPPLLEFSGACAGCGETPYARLITQLF
GDRMMIANATGCSSIWGASAPSIPWTTNHKGQGPAWANSLFEDNAEFGLGMMLG
GRAIREQLASDAASVLERPLHPDLQQALRDWLEHKDLGEGTRARAEKLSALLAAE
KGDDDLLNRLYQNQDYFTKRSQWIFGGDGWAYDIGFGGLDHVLASGEDVNILVF
DTEVYSNTGGQSSKSTPVAAIAKFAAEGKRTRKKDLGMMAVSYGNVYVAQVAM
GADKAQTLRAIAEAEAWPGPSLVIAYAACINHGLKAGMGRSISEAKRAVEAGYW
HLWRYNPQLLAKGKNPFILDSEEPEESFRDFLMGEVRYASLGRTSPEVADSLFAQT
EQDAKDRYAQYRRLAGE SEQ ID NO: 31 (*Desulfovibrio africanus*, Da.pfor)
MGKKMMTTDGNTATAHVAYAMSEVAAIYPITPSSTMGEEADDWAAQGRKNIFG
QTLTIREMQSEAGAAGAVHGALAAGALTTTFTASQGLLLMIPNMYKISGELLPGV
FHVTARAIAAHALSIFGDHQDIYAARQTGFAMLASSSVQEAHDMALVAHLAAIES
NVPFMHFFDGFRTSHEIQKIEVLDYADMASLVNQKALAEFRAKSMNPEHPHVRGT

| SEQUENCES |
| --- |
| AQNPDIYFQGREAANPYYLKVPGIVAEYMQKVAALTGRSYKLFDYVGAPDAERV<br>IVSMGSSCETIEEVINHLAAKGDKIGLIKVRLYRPFVSEAFFAALPASAKVITVLDRT<br>KEPGAPGDPLYLDVCSAFVERGEAMPKILAGRYGLGSKEFSPAMVKSVYDNMSG<br>AKKNHFTVGIEDDVTGTSLPVDNAFADTTPKGTIQCQFWGLGADGTVGANKQAI<br>KIIGDNTDLFAQGYFSYDSKKSGGITISHLRFGEKPIQSTYLYNRADYVACHNPAY<br>VGIYDILEGIKDGGTFVLNSPWSSLEDMDKHLPSGIKRTIANKKLKFYNIDAVKIAT<br>DVGLGGRINMIMQTAFFKLAGVLPFEKAVDLLKKSIHKAYGKKGEKIVKMNTDA<br>VDQAVTSLQEFKYPASWKDAPAETKAEPKTNEFFKNVVKPILTQQGDKLPVSAFE<br>ADGRFPLGTSQFEKRGVAINVPQWVPENCIQCNQCAFVCPHSAILPVLAKEEELVG<br>APANFTALEAKGKELKGYKFRIQINTLDCMGCGNCADICPPKEKALVMQPLDTQR<br>DAQVPNLEYAARIPVKSEVLPRDSLKGSQFQEPLMEFSGACSGCGETPYVRVITQL<br>FGERMFIANATGCSSIWGASAPSMPYKTNSLGQGPAWGNSLFEDAAEYGFGMNM<br>SMFARRTHLADLAAKALESDASGDVKEALQGWLAGKNDPIKSKEYGDKLKKLLA<br>GQKDGLLGQIAAMSDLYTKKSVWIFGGDGWAYDIGYGGLDHVLASGEDVNVFV<br>MDTEVYSNTGGQSSKATPTGAVAKFAAAGKRTGKKDLARMVMTYGYVVVATV<br>SMGYSKQQFLKVLKEAESFPGPSLVIAYATCINQGLRKGMGKSQDVMNTAVKSG<br>YWPLFRYDPRLAAQGKNPFQLDSKAPDGSVEEFLMAQNRFAVLDRSFPEDAKRL<br>RAQVAHELDVRFKELERMAATNIFESFAPAGGKADGSVDFGEGAEFCTRDDTPM<br>MARPDSGEACDQNRAGTSEQQGDLSKRTKK<br><br>SEQ ID NO. 32 (*Nostoc* sp., Ns.pfor)<br>MSQTFATIDGNEAVARVAYKLNEVIAIYPITPSSAMGEWADAWMAEGRPNLWGT<br>VPSVVQMQSEGGAAGAVHGALQTGSLSTTFTASQGLLLMIPNLYKIGGELTSMVV<br>HVAARSLATHALSIFGDHSDVMAARGTGFAMLCSASVQESHDFALIAHAATLDTR<br>VSFLHFFDGFRTSHEVQKVELLADDDVRSLINEDKIFAHRARALTPDSPLLRGTAQ<br>NPDVFFQAREGANPYYNACPAIVQGIMDKFGERTGRYYQIYEYHGASDADRLIILM<br>GSGCETVHETVDYLNARGEKVGVLKVRLFRPWDVERFVQALPHSVQAIAVLDRT<br>KEPGSAGEPLYQDVVTAIHEGWVNKNNSPVPSPQSPVPKIIGGRYGLSSKEFTPAM<br>VKAVFDNLAQATPKNHFTIGINDDVTHTSLEYDPSFSTEPDNVVRAMFYGLGSDG<br>TVGANKNSIKIIGEGGTDNYAQGYFVYDSKKSGSMTVSHLRFGSQPIRSTYLIDQAN<br>FIGCHHWGFLERIEVLNAAAHGATILLNSPYNAATVWENLPLKVRLQILDKQLKL<br>YVINANQVARDSGMGGRIMTIMQVCFFALAGVLPEVQAIAKIKQAIEKTYGKKGV<br>EVVRMNLQAVDQTLENLHEVKIPIEEKGKWIDEEALLSNQSPFSTSAPKFVRDVLG<br>KIMVWQGDDLPVSTLPPDGTFPTGTAKWEKRNVAQEIPVWDTDICVQCSKCVMV<br>CPHAAIRAKVYQPSELENAPPTFKSVDAKDRDFANQKFTIQVAPEDCTGCAICVNV<br>CPAKNKSEPSLKAINMANQLPLREQERDNWDFFLNLPNPDRRNLKLNQIRQQQLQ<br>EPLFEFSGACAGCGETPYVKLLTQLFGDRSVIANATGCSSIYYGGNLPTTPWTKNND<br>GRGPAWSNSLFEDNAEFGFGYRLSLDKQAEFAAELLQQFSTEVGDNLVDSILKAP<br>QKTEADIWEQRQRIELLKQQLDKIPTFDPNLKSKIQNLKSLADYLVKKSVWIIGGD<br>GWAYDIDFGGIDHVIASGRNVNILVMDTEVTYSNTGGQSSKATPKAAVAKFAASG<br>KPAQKKDMGLMAMNYGNVYVASVALGAKDDQTLKAFLEAEAFDGPSIIIAYSHC<br>IAHGINMTTGMNQQKALVESGRWLLYRYNPLLQEQGKNPLQLDMRSPTQSVEQS<br>MYQENRFKMLTKSKPEVAKQLLEQAQAEVDARWQMYQYLASR<br><br>SEQ ID NO: 33 (*E. coli*, Ec.ydhV)<br>MANGWTGNILRVNLTTGNITLEDSSKFKSFVGGMGFGYKIMYDEVPPGTKPFDEA<br>NKLVFATGPLTGSSGAPCSSRVNITSLSTFTKGNLVVDAHMGGFFAAQMKFAGYDV<br>IIIEGKAKSPVWLKIKDDKVSLEKADFLWGKGTRATTEEICRLTSPETCVAAIGQAG<br>ENLVPLSGMLNSRNHSGGAGTGAIMGSKNLKAIAVEGTKGVNIADRQEMKRLND<br>YMMTELIGANNNHVVPSTPQSWAEYSDPKSRWTARKGLFWGAAEGGPIETGEIPP<br>GNQNTVGFRTYKSVFDLGPAAEKYTVKMSGCHSCPIRCMTQMNIPRVKEFGVPST<br>GGNTCVANFVHTTIFPNGPKDFEDKDDGRVIGNLVGLNLFDDYGLWCNYGQLHR<br>DFTYCYSKGVFKRVLPAEETAEIRWDQLEAGDVNFIKDFYYRLAHRVGELSHLAD<br>GSYAIAERWNLGEEYWGYAKNKLWSPFGYPVHHANEASAQVGSIVNCMFNRDC<br>MTHTHINFIGSGLPLKLQREVAKELFGSEDAYDETKNYTPINDAKIKYAKWSLLRV<br>CLHNAVTLCNWVWPMTVSPLKSRNYRGDLALEAKFFKAITGEEMTQEKLDLAAE<br>RIFTLHRAYTVKLMQTKDMRNEHDLICSWVFDKDPQIPVFTEGTDKMDRDDMHA<br>SLTMFYKEMGWDPQLGCPTRETLQRLGLEDIAADLAAHNLLPA<br><br>SEQ ID NO: 34 (*E. coli*, Ec.ydhY)<br>MNPVDRPLLDIGLTRLEFLRISGKGLAGLTIAPALLSLLGCKQEDIDSGTVGLINTPK<br>GVLVTQRARCTGCHRCEISCTNFNDGSVGTFFSRIKIHRNYFFGDNGVGSGGGLYG<br>DLNYTADTCRQCKEPQCMNVCPIGAITWQQKEGCITVDHKRCIGCSACTTACPW<br>MMATVNTESKKSSKCVLCGECANACPTGALKIIEWKDITV<br><br>SEQ ID NO: 35 (*Gilliamella apicola*, Ga.pfor)<br>MIISDANSAVSSVAYRANEVIAIYPITPSSSMAEQASTWAEFDKPNVFGDIPRVVEM<br>QSEAGAIATVHGALMTGALATSFTSSQGLLLMIPSLYKIAGELTPFVLHVAARTVA<br>THALSIFGDHSDVMSVRQTGFAMLCSSSVQEAQDLALISQIASFKSRIPFVHFFDGF<br>RTSHEVNKIYPLSDEDIHDLLPHEAIKAYRSALTPDKPMIRGTSANPDTYFQCREA<br>INSYYDNAYQHVVDAMTDFEKQTGRKYQPFEYYGASDAERIIVIMGSGASTSKEV<br>IDYLLKENQKVGVVIVRLFRPFSAQHLLAVIPDSVKKIAVLDRTKEPGAQAEPLYL<br>DIMTAFAESLSRGERNTIPQTVGGRYGLSSKEFDPRSVLGIFNELSLEKPRPRFTVGI<br>YDDITGLSLPLPDKTIPQKSALEALFYGLGSDGTVSATKNNIKIIGDSSPFYVQGYFV<br>YDSKKAGGLTTSHLRVNLDPIDSPYLITSAHFIGCHQDQFIDKYQIVDKLKNDGIFL<br>LNTPYNKDEIWHRLPKEVQVQLIKKRAHFYIINAAKIARECNLGARINTVMQAAFF<br>HLSDIFKNDFSISQLKEVIAKSYSSKGQELVENNWKALDLAITSLEQIPLNCVDQSS |

| SEQUENCES |
|---|
| PSMPPIVPNNAPDFVKTVTATMLAGLGDSLPVSAFPPDGAWPTGTTKWEKRNIAE
EIPWKSELCTQCNHCAVACPHAAIRAKVVEPDAMLNAPDTLESLEVKARDMKGQ
RYVLQVAPEDCTGCNLCVEVCPSRDRNNFDIKAINMQPRIDNLDTQRVNEEFFSAL
PDRDIKSLDRIDIRTSQLITPLFEYSGACAGCGETPYIKLLTQLYGDHLAIANATGCS
SIYGGNLPSTPYTTDRSGRGPAWANSLFEDNAEFALGYRITYNQHRKRALRLLDH
LAGEISPEIVITLQSSDATIAEKRTQVDLLREQLKHIDSAEAKELLEDTNYLIDKSVW
AIGGDGWAYDIGFGGLDHVMSLTDNVNILVLDTQCYSNTGGQQSKATPMGAVSK
FADLGKHKARKDLGVSIMMYGHVYVAQVALGSQLNQTLKALQEAEAYDGPSLVI
AYSPCEEHGYDLAKSHEQMKDLVKSGFWPLYRYDPRRSAEGKPGLVLDSKSPNS
EALSSILLKEQRFRRLETLEPTVANILHERSTKMVESKYRFLQMLSSYSDIETPPDS

SEQ ID NO: 36 (*Nostoc* sp., Ns.fpr)
MSNQGAFDGAANVESGSRVFVYEVVGMRQNEETDQTNYPIRKSGSVFIRVPYNR
MNQEMQRITRLGGKIVTIQTVSALQQLNGRTTIATVTDASSEIAKSEGNGKATPVK
TDSGAKAFAKPPAEEQLKKKDNKGNTMTQAKAKHADVPVNLYRPNAPFIGKVIS
NEPLVKEGGIGIVQHIKFDLTGGNLKYIEGQSIGIIPPGVDKNGKPEKLRLYSIASTR
HGDDVDDKTISLCVRQLEYKHPESGETVYGVCSTYLTHIEPGSEVKITGPVGKEML
LPDDPEANVIMLATGTGIAPMRTYLWRMFKDAERAANPEYQFKGFSWLVFGVPT
TPNILYKEELEEIQQKYPDNFRLTYAISREQKNPQGGRMYIQDRVAEHADELWQLI
KNQKTHTYICGLRGMEEGIDAALSAAAAKEGVTWSDYQKDLKKAGRWHVETY SEQ ID NO: 37 (*Synechococcus* sp., Sco.fpr)
MYGITSTANSTGNQSYANRLFIYEVVGLGGDGRNENSLVRKSGTTFITVPYARMN
QEMQRITKLGGKIVSIRPAEDAAQIVSEGQSSAQASAQSPMASSTKIVHPKTTDTSV
PVNIYRPKTPFLGKCIENYELVDEGGSGTVRHVTFDISEGDLRYLEGQSIGIIPPGED
KNGKPHKLRLYSIASTRHGDMEDNKTVSLCVRQLEYQDPESGETVYGVCSTYLCN
LPVGTDDVKITGPVGKEMLLPDDEDATVVMLATGTGIAPFRAFLWRMFKEQHED
YKFKGKAWLIFGVPYTANILYKDDFEKMAAENPDNFRLTYAISREQKTADGGKV
YVQSRVSEYADELFEMIQKPNTHVYMCGLKGMQPPIDETFTAEAEKRGLNWEEM
RRSMKKEHRWHVEVY SEQ ID NO: 38 (*E. coli*, Ec.fpr)
MADWVTGKVTKVQNWTDALFSLTVHAPVLPFTAGQFTKLGLEIDGERVQRAYSY
VNSPDNPDLEFYLVTVPDGKLSPRLAALKPGDEVQVVSEAAGFFVLDEVPHCETL
WMLATGTAIGPYLSILQLGKDLDRFKNLVLVHAARYAADLSYLPLMQELEKRYE
GKLRIQTVVSRETAAGSLTGRIPALIESGELESTIGLPMNKETSHVMLCGNPQMVR
DTQQLLKETRQMTKHLRRPGHMTAEHYW |

---

The invention claimed is:

1. A bacterial strain having one or more genetic modifications that increase production of products from isopentenyl diphosphate (IPP) and dimethylallyl diphosphate (DMAPP) precursors; the bacterial strain producing isopentenyl diphosphate (IPP) and dimethylallyl diphosphate (DMAPP) through an methylerythritol phosphate pathway (MEP pathway), and the MEP pathway comprising one or more overexpressed genes; the strain converting the IPP and DMAPP to a terpene or terpenoid product through a downstream synthesis pathway; wherein said genetic modifications comprise:
- (a) recombinant or modified IspG and IspH enzymes, the IspG and IspH enzymes having balanced expression or activity to prevent accumulation of (1-hydroxy-2-methyl-2(E)-butenyl 4-diphosphate (HMBPP) intermediate,
- (b) a recombinant or modified gene encoding an enzyme that enhances supply and/or transfer of electrons through the MEP pathway and/or to terpene or terpenoid products, and
- (c) an inactivation or deletion, or reduced expression or activity, of aceE or aceE enzyme complex.

2. The bacterial strain of claim 1, wherein the bacterial strain is a bacteria selected from *Escherichia* spp., *Bacillus* spp., *Corynebacterium* spp., *Rhodobacter* spp., *Zymomonas* spp., *Vibrio* spp., and *Pseudomonas* spp.

3. The bacterial strain of claim 2, wherein the bacterial strain is a species selected from *Escherichia coli, Bacillus subtillus, Corynebacterium glutamicum, Rhodobacter capsulatus, Rhodobacter sphaeroides, Zymomonas mobilis, Vibrio natriegens,* or *Pseudomonas putida.*

4. The bacterial strain of claim 3, wherein the bacterial strain is *E. coli.*

5. The bacterial strain of claim 1, wherein the bacterial strain expresses dxs, ispD, ispF, and idi as recombinant genes.

6. The bacterial strain of claim 5, wherein the bacterial strain expresses dxs, dxr, ispD, ispE, ispF, and idi as recombinant genes.

7. The bacterial strain of claim 1, wherein HMBPP does not accumulate at greater than 10 mg/g of dry cell weight.

8. The bacterial strain of claim 1, wherein the expression of recombinant IspH is higher than the expression of the recombinant IspG.

9. The bacterial strain of claim 8, wherein the recombinant ispH and ispG are expressed as an operon, with ispH positioned before ispG in the operon.

10. The bacterial strain of claim 9, wherein the operon is expressed under control of a strong promoter.

11. The bacterial strain of claim 1, wherein the expression or activity of a recombinant idi gene is tuned to increase terpene or terpenoid production by modifying the promoter strength, gene copy number, position in an operon, or ribosome binding site.

12. The bacterial strain of claim 1, wherein the bacterial strain contains an overexpression of an oxidoreductase.

13. The bacterial strain of claim 12, wherein the oxidoreductase is a pyruvate:flavodoxin oxidoreductase (PFOR).

14. The bacterial strain of claim 13, wherein the PFOR is YdbK.

15. The bacterial strain of claim 1, wherein the strain comprises one or more P450 enzymes for the production of a terpenoid compound.

16. The bacterial strain of 15, further comprising an overexpression of one or more of a flavodoxin, flavodoxin reductase, ferredoxin, and ferredoxin reductase.

17. The bacterial strain of claim 1, wherein the bacterial strain expresses recombinant pgpB and/or nudB and the expression of the recombinant pgpB and/or nudB is tuned to provide higher terpene or terpenoid product titer by varying the promoter strength, gene copy number, position in an operon, and/or ribosome binding site.

18. The bacterial strain of claim 1, wherein the strain has one or more additional modifications selected from: recombinant expression of a glyceraldehyde-3-phosphate ferredoxin oxidoreductase (GAPOR); overexpression of ydhV and/or ydhY; downregulation, inactivation, or deletion of gshA; and recombinant expression of CHAC1 and/or CHAC2.

19. The bacterial strain of claim 18, wherein the recombinant pgpB and/or nudB is expressed under control of a weak or intermediate strength promoter.

20. The bacterial strain of claim 1, wherein the bacterial strain has reduced or eliminated pyruvate dehydrogenase (PDH)-mediated conversion of pyruvate to acetyl-CoA.

21. The bacterial strain of claim 20, wherein the bacterial strain expresses a mutant aceE.

22. The bacterial strain of claim 21, wherein the bacterial strain has a deletion or inactivation of aceE.

23. The bacterial strain of claim 1, wherein the bacterial strain overexpresses one or more non-native ferredoxin (fdx) and/or flavodoxin (fldA) homolog.

24. The bacterial strain of claim 23, wherein the non-native fdx homolog is selected from Hm.fdx1 (*Heliobacterium modesticaldum*), Pa.fdx (*Pseudomonas aeruginosa*), Cv.fdx (*Allochromatium vinosum*), Ca.fdx (*Clostridium acetobutylicum*), Cp.fdx (*Clostridium pasteurianum*), and Ev2.fdx (*Ectothiorhodospira shaposhnikovii*), Pp1.fdx (*Pseudomonas putida*) and Pp2.fdx (*Pseudomonas putida*), or derivative of any of the foregoing.

25. The bacterial strain of claim 24, wherein the fldA homolog is selected from Ac.fldA2 (*Azotobacter chroococcum*), Av.fldA2 (*Azotobacter vinelandii*), and Bs.fldA (*B. subtilis*), or a derivative thereof.

26. The bacterial strain of claim 1, wherein the terpene or terpenoid product comprises at least one compound selected from: Farnesene, Amorphadiene, Artemisinic acid, Artemisinin, Bisabolol, Bisabolene, alpha-Sinensal, beta-Thujone, Camphor, Carveol, Carvone, Cineole, Citral, Citronellal, Cubebol, Geraniol, Limonene, Menthol, Menthone, Myrcene, Nootkatone, Nootkatol, Patchouli, Piperitone, Rose oxide, Sabinene, Steviol, Steviol glycoside (including Rebaudioside D or Rebaudioside M), Taxadiene, Thymol, and Valencene.

27. The bacterial strain of claim 1, wherein the bacterial strain overexpresses one or more of geranyl diphosphate synthase (GPPS), farnesyl diphosphate synthase (FPPS), and geranylgeranyl diphosphate synthase (GGPPS).

* * * * *